United States Patent
Canedo

(10) Patent No.: US 10,795,976 B2
(45) Date of Patent: Oct. 6, 2020

(54) PROGRAM RANDOMIZATION FOR CYBER-ATTACK RESILIENT CONTROL IN PROGRAMMABLE LOGIC CONTROLLERS

(71) Applicant: Siemens Aktiengesellschaft, Munich (DE)

(72) Inventor: Arquimedes Martinez Canedo, Plainsboro, NJ (US)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 16/067,058

(22) PCT Filed: Dec. 13, 2016

(86) PCT No.: PCT/US2016/066295
§ 371 (c)(1),
(2) Date: Jun. 28, 2018

(87) PCT Pub. No.: WO2017/123367
PCT Pub. Date: Jul. 20, 2017

(65) Prior Publication Data
US 2019/0008845 A1 Jan. 10, 2019

Related U.S. Application Data

(60) Provisional application No. 62/277,014, filed on Jan. 11, 2016.

(51) Int. Cl.
G06F 21/14 (2013.01)
G05B 19/05 (2006.01)
G06F 21/76 (2013.01)

(52) U.S. Cl.
CPC ............ *G06F 21/14* (2013.01); *G05B 19/056* (2013.01); *G06F 21/76* (2013.01); *G05B 2219/13019* (2013.01); *G05B 2219/13022* (2013.01)

(58) Field of Classification Search
CPC .... G06F 8/40–52; G06F 21/12; G06F 21/125; G06F 21/126; G06F 21/128;
(Continued)

(56) References Cited

U.S. PATENT DOCUMENTS 6,754,862 B1* 6/2004 Hoyer ................... G06F 30/331
714/725
7,426,724 B2* 9/2008 Kilgard ................... G06F 8/443
717/151

(Continued)

FOREIGN PATENT DOCUMENTS

CN 102156840 A 8/2011
CN 105094937 A 11/2015
(Continued)

OTHER PUBLICATIONS

Chavez, A., et al., Network Randomization and Dynamic Defense for Critical Infrastructure Systems, Sandia Report SAND2015-3324, Apr. 2015, 41 pages, [retrieved on Mar. 9, 2020], Retrieved from the Internet.*

(Continued)

*Primary Examiner* — Geoffrey R St Leger

(57) ABSTRACT

A method for programmable logic controller (PLC) program randomization, the method comprising an engineering system computer receiving source code corresponding to a PLC program and compiling the source code into a plurality of functionally equivalent intermediate representations of the PLC program. Program structure of the PLC program is randomized during compilation such that each intermediate representation is unique among the plurality of intermediate representations. The engineering system computer transmits the plurality of intermediate representations to one or more PLCs.

20 Claims, 9 Drawing Sheets

(58) Field of Classification Search
CPC ......... G06F 21/14; G06F 21/76; G05B 19/05; G05B 19/056; G05B 2219/13019; G05B 2219/13022
USPC .................................................. 717/131–161
See application file for complete search history.

(56) References Cited

U.S. PATENT DOCUMENTS

| | | | | |
|---|---|---|---|---|
| 7,512,936 | B2* | 3/2009 | Schneider | G06F 21/14 717/136 |
| 8,056,138 | B2* | 11/2011 | Jin | G06F 21/125 726/26 |
| 8,255,065 | B2* | 8/2012 | Lu | G05B 19/056 700/21 |
| 8,806,187 | B1* | 8/2014 | Vemula | H04L 67/34 713/150 |
| 10,579,036 | B2 | 3/2020 | Lee | |
| 2005/0071825 | A1* | 3/2005 | Nagaraj | G06F 8/447 717/142 |
| 2005/0262347 | A1* | 11/2005 | Sato | G06F 21/125 713/176 |
| 2006/0005178 | A1* | 1/2006 | Kilgard | G06F 8/443 717/153 |
| 2006/0136867 | A1* | 6/2006 | Schneider | G06F 21/14 717/106 |
| 2006/0185906 | A1 | 8/2006 | Vail | |
| 2006/0195906 | A1* | 8/2006 | Jin | G06F 21/125 726/26 |
| 2007/0234070 | A1* | 10/2007 | Horning | G06F 21/14 713/190 |
| 2009/0276060 | A1* | 11/2009 | Lu | G05B 19/056 700/21 |
| 2010/0281459 | A1* | 11/2010 | Betouin | G06F 21/14 717/106 |
| 2012/0030758 | A1* | 2/2012 | van den Berg | G06F 21/54 726/22 |
| 2015/0227448 | A1* | 8/2015 | Goel | G06F 11/3466 717/131 |
| 2015/0294114 | A1* | 10/2015 | Monahan | G06F 21/14 726/26 |
| 2018/0137280 | A1* | 5/2018 | Guri | G06F 21/51 |

FOREIGN PATENT DOCUMENTS

| | | | |
|---|---|---|---|
| EP | 2169547 | A1 | 3/2010 |
| WO | WO-2012033478 | A1 * | 3/2012 |

OTHER PUBLICATIONS

PCT Search Report dated May 16, 2017, for PCT Application No. PCT/US2017/066295, 28 pages.

Schwartz Moses et al: "Emerging Techniques for Field Device Security" Nov. 1, 2014 (Nov. 1, 2014) Security & Privacy, IEEE, IEEE Service Center, Los Alamitos, CA, US, pp. 24-31, XP011570172 / Nov. 1, 2014, 8 pages.

Michael Franz: "E unibus pluram", New Security Paradigms, ACM, 2 Penn Plaza, Suite 701 New York NY 10121-0701 USA, Sep. 21, 2010 (Sep. 21, 2010), pp. 7-16, XP058312861, DOI: 10.1145/1900546.1900550 ISBN: 978-1-4503-0415-3 page 8 figure 3 / Sep. 21, 2010, 10 pages.

Dimitrios Hristu-Varsakelis et al: "Handbook of Networked and Embedded Control Systems" In: "Handbook of Networked and Embedded Control Systems", Jan. 1, 2005 (Jan. 1, 2005), Birkhauser Boston, Boston, MA, XP055363099, ISBN: 978-0-8176-4404-8 pp. 259-278, p. 268 / Jan. 1, 2005, 28 pages.

Forrest S et al: "Building diverse computer systems", Operating Systems, 1997., The Sixth Workshop on Hot Topics in Cape Cod, MA, USA May 5-6, 1997, Los Alamitos, CA, USA,IEEE Comput. Soc, US, May 5, 1997 (May 5, 1997), pp. 67-72, XP010226847, DOI: 10.1109/HOTOS.1997.595185 ISBN: 978-0-8186-7834-9 / May 5, 1997, 6 pages.

Siemens Ag Siemens Ag: "Programming Guideline for S7-1200/1500", Mar. 1, 2014 (Mar. 1, 2014), XP055362727, Retrieved from the Internet: URL:https://www.industry.siemens.nl/automa tion/nl/nl/industriele-automatisering/industrial-automation/simatic-controller/modul aire-controllers/simatic-s7-1500/Documents/81318674 Programmingguideline DOKU v12 e n.pdf [retrieved on Apr. 6, 2017] p. 10 / Mar. 1, 2014, 74 pages.

Anonymous: "Address space layout randomization—Wikipedia" Dec. 2, 2015 (Dec. 2, 2015), XP055363110, Retrieved from the Internet: URL:https://en.wikipedia.org/w/index.php?t itle=Address space layout randomization&oldid=693416768, 7 pages.

Höller Andrea et al: "Patterns for automated software diversity to support security and reliability" Pattern Languages of Programs, ACM, 2 Penn Plaza, Suite 701 New York NY 10121-0701, USA, pp. 1-13, XP058079545, DOI: 10.1145/2855321.2855360, ISBN: 978-1-4503-3847-9, abstract, figure 3, 5, Section 2.1, 4, table II, III / Jul. 8, 2015, 13 pages.

Search Report dated Jun. 17, 2020; Chinese Patent Application No. 2016800783757; 6 pages.

\* cited by examiner

PROGRAM RANDOMIZATION FOR CYBER-ATTACK RESILIENT CONTROL IN PROGRAMMABLE LOGIC CONTROLLERS

CROSS REFERENCE TO RELATED APPLICATIONS

This application claims priority to U.S. Provisional Patent Application Ser. No. 62/434,769, filed on Dec. 15, 2016, the entire content of which is hereby incorporated by reference in its entirety.

FIELD OF THE INVENTION

The present invention is in the field of mental, movement and behavioral disorders and specifically in treating, preventing and/or ameliorating behavior disorders characterized by repetitive phenotype, by treatment with a pharmaceutical composition comprising at least one active agent selected from a group of active agents comprising CB2 receptor inverse agonists, mixed CB2/SERM ligands and combinations thereof.

BACKGROUND OF THE INVENTION

Some Tourette syndrome (TS) patients have reported that the cannabinoid $\Delta^9$-tetrahydrocannabinol ($\Delta^9$THC) (Muller-Vahl et al., Pharmacopsychiatry 35: 57-61, 2002) and Sativex, a mixture of cannabidiol (CBD) and $\Delta^9$-tetrahydrocannabinol ($\Delta^9$-THC), ameliorate tic frequency (Trainor, Evans & Bird, Australasian psychiatry: bulletin of Royal Australian and New Zealand College of Psychiatrists, 2016). However, $\Delta^9$-THC is a psychoactive compound that affects memory and increases the risk for psychosis. Therefore, the treatment with $\Delta^9$-THC is not a preferred treatment, especially not for young patients, children and teenagers.

There is an unmet need for improved methods of treatment for disorders exhibiting repetitive behaviors, which would provide higher cure rates and fewer or no side effects. Some of the cannabinoids are CB2 receptor inverse agonists. It was surprisingly found that these molecules can modulate brain function while being devoid of psychoactive effects.

Cannabinoids are compounds found mainly in *Cannabis sativa* (also known as marijuana) with cannabidiol (CBD) and $\Delta^9$-tetrahydrocannabinol ($\Delta^9$-THC) being the most representative molecules. The therapeutic usage of *Cannabis* can be dated back to ancient dynasties of China and includes applications for various illnesses ranging from lack of appetite, emesis, cramps, menstrual pain, spasticity to rheumatism. The long history of *Cannabis* use has led to the development of several pharmaceutical drugs. For example, Marinol and Cesamet which are based on $\Delta^9$-THC and nabilone (a synthetic cannabinoid mimicking $\Delta^9$-THC) respectively, are used as anti-emetic and appetite stimulant. Another example is cannabidiol which has been found effective in the treatment of epilepsy. Despite the clinical benefits, the therapeutic usage of *Cannabis* is limited by its negative psychoactive effects including hallucination, addiction and dependence.

The effects of $\Delta^9$-THC are mediated by at least two G-protein coupled receptors, CB1 and CB2 receptors. CB1 receptors are expressed primarily in the central nervous system, specifically in the cerebral cortex, hippocampus, basal ganglia and cerebellum. These receptors are also found in the reproductive system and in other peripheral tissues including that of the immune system, but to a lesser degree. CB1 receptors regulate the release of neurotransmitters from the pre-synaptic neurons and are believed to mediate most of the euphoric and other central nervous system effects of $\Delta^9$-THC.

SUMMARY OF THE INVENTION

Aspects of the present invention provide compositions and methods of treatment of disorders, comprising selected mental, movement or behavioral disorders exhibiting an increased or repetitive vocalization, a motor repetitive movement, a repetitive behavior or an involuntary movement.

In some embodiments, there is provided a pharmaceutical composition and a method of treatment of a disorder selected from the group consisting of developmental coordination disorder, stereotypic movement disorder, autism spectrum disorders, obsessive-compulsive disorder (OCD), bacterial-induced repetitive behavior, NMDA antibody-related encephalitis, autoimmune antibody-mediated mental disorder, autoimmune antibody-mediated psychosis, pediatric autoimmune neuropsychiatric disorders associated with streptococcal infections (PANDAS), chorea (Sydenham's chorea (SC), chorea minor, chorea gravidarum, drug-induced chorea), drug-induced repetitive behaviors, akathisia, dyskinesias, dystonias, cramps and spasms, tremors, restless leg syndrome, moving toes/fingers syndrome, involuntary movement, extrapyramidal movement disorders, Wernicke-Korsakoff syndrome and combinations thereof, wherein acute, transient or chronic, the method comprising administering to a subject in need thereof a therapeutically effective dose of a pharmaceutical composition comprising at least one active agent selected from the group of CB2 receptor inverse agonists and mixed CB2/SERM ligands consisting of (i), (ii), (iii), (iv) or (v) in a pharmaceutically acceptable carrier, wherein (i) a CB2 receptor inverse agonist of formula I or pharmaceutical salt thereof:

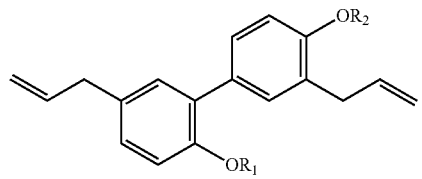

wherein R1 and R2 are each independently selected from the group consisting of hydrogen, C1-C8 alkyl, C3-C8 cycloalkyl, C1-C8 haloalkyl, or C3-C8 cyclohaloalkyl, wherein R1 and R2 are not both hydrogen;

(ii) a mixed CB2/SERM ligand of formula II or pharmaceutical salt thereof:

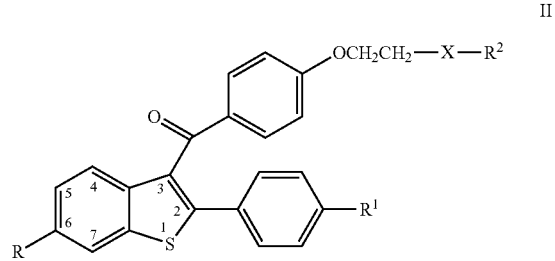

wherein:

X is a bond, $CH_2$, or $CH_2CH_2$;

R and $R^1$, independently, are selected from the group consisting of hydrogen, hydroxyl, $C_1$-$C_6$ alkoxy, $C_1$-$C_6$-acyloxy, $C_1$-$C_6$-alkoxy-$C_2$-$C_6$-acyloxy, $R_3$-substituted aryloxy, $R_3$-substituted aroyloxy, $R^4$-substituted carbonyloxy, chloro, or bromo;

$R_2$ is a heterocyclic ring selected from the group consisting of pyrrolidino, piperidino, or hexamethyleneimino;

$R^3$ is $C_1$-$C_3$-alkyl, C1-C3-alkoxy, hydrogen, or halo; and $R^4$ is $C_1$-$C_6$-alkoxy or aryloxy;

(iii) the CB2 receptor inverse agonist N-(benzo[1,3]dioxol-5-ylmethyl)-7-methoxy-2-oxo-8-pentyloxy-1,2-dihydroquinoline-3-carboxamide (JTE 907), (iv) the CB2 receptor inverse agonist 5-(4-Chloro-3-methylphenyl)-1-[(4-methylphenyl)methyl]-N-[(1S,2S,4R)-1,3,3-trimethylbicyclo[2.2.1]heptan-2-yl]-1H-pyrazole-3-carboxamide (SR 144528); or (v) combinations of (i)-(iv), and wherein the active agents (i)-(v) are formulated in a pharmaceutically effective carrier.

In some embodiments, the active agent is a CB2 receptor inverse agonist of formula I, wherein R1 is hydrogen and R2 is methyl, and wherein the CB2 receptor inverse agonist is 4'-O-Methylhonokiol.

In some embodiments, there is provided the above method of treatment of a disorder, wherein the disorder is selected from pediatric autoimmune neuropsychiatric disorders associated with streptococcal infections (PANDAS), NMDA antibody-related encephalitis, autoimmune antibody-mediated mental disorder, autoimmune antibody-mediated psychosis, chorea and combinations thereof.

In some embodiments, the disorder is an autism spectrum disorder.

In some embodiments, the disorder is selected from akathisia, dyskinesias and combinations thereof.

In some embodiments, there is provided a pharmaceutical composition and a method of treatment of a disorder selected from the group consisting of Tourette syndrome, developmental coordination disorder, stereotypic movement disorder, autism spectrum disorders, bacterial-induced repetitive behavior, NMDA antibody-related encephalitis, autoimmune antibody-mediated mental disorder, autoimmune antibody-mediated psychosis, pediatric autoimmune neuropsychiatric disorders-associated with streptococcal infections (PANDAS), chorea (Sydenham's chorea (SC), chorea minor, chorea gravidarum, drug-induced chorea), drug-induced repetitive behaviors, akathisia, dyskinesias, dystonias, cramps and spasms, tremors, restless leg syndrome, moving toes/fingers syndrome, involuntary movement, stereotypic movement disorder, extrapyramidal movement disorders, Wernicke-Korsakoff syndrome and a combination thereof wherein acute, transient or chronic, comprising administering to a subject in need thereof a pharmaceutical composition comprising a therapeutically effective amount of a mixed CB2/SERM ligand in a pharmaceutically acceptable carrier, wherein the mixed CB2/SERM ligand has formula II or a pharmaceutically acceptable salt thereof:

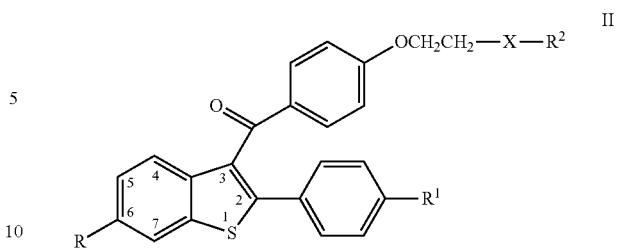

wherein

X is a bond, $CH_2$, or $CH_2CH_2$;

R and $R^1$, independently, are hydrogen, hydroxyl, $C_1$-$C_6$ alkoxy, $C_1$-$C_6$-acyloxy, $C_1$-$C_6$-alkoxy-$C_2$-$C_6$-acyloxy, $R_3$-substituted aryloxy, $R_3$-substituted aroyloxy, $R^4$-substituted carbonyloxy, chloro, or bromo;

$R^2$ is a heterocyclic ring selected from the group consisting of pyrrolidino, piperidino, or hexamethyleneimino;

$R^3$ is $C_1$-$C_3$-alkyl, C1-C3-alkoxy, hydrogen, or halo; and $R^4$ is $C_1$-$C_6$-alkoxy or aryloxy.

In some embodiments, there is provided the above method of treatment of a disorder and pharmaceutical composition, wherein the mixed CB2/SERM ligand is selected from the group consisting of raloxifene, bazedoxifene, lasofoxifene, tamoxifen, afimoxifene, arzoxifene, ormeloxifene, toremifene, ospemifene, and a combination thereof.

In some alternative embodiments, there is provided the above method of treatment of a disorder and pharmaceutical composition, wherein the mixed CB2/SERM ligand is raloxifene.

In some embodiments, there is provided a method of treatment of a disorder, wherein the disorder is selected from the group consisting of ADHD (Attention-deficit hyperactivity disorder), Tourette syndrome (TS), tic disorder, vocal disorder, developmental coordination disorder, stereotypic movement disorder, autism spectrum disorders, obsessive-compulsive disorder (OCD), bacterial-induced repetitive behavior, NMDA antibody-related encephalitis, autoimmune antibody-mediated mental disorder, autoimmune antibody-mediated psychosis, pediatric autoimmune neuropsychiatric disorders associated with streptococcal infections (PANDAS), chorea (Sydenham's chorea (SC), chorea minor, chorea gravidarum, drug-induced chorea), drug-induced repetitive behaviors, akathisia, dyskinesias, dystonias, cramps and spasms, tremors, restless leg syndrome, moving toes/fingers syndrome, involuntary movement, stereotypic movement disorder, extrapyramidal movement disorders, Wernicke-Korsakoff syndrome and combinations thereof, wherein acute, transient or chronic, comprising administering a fixed drug combination composition comprising therapeutically effective amounts of at least two therapeutic agents selected from the group consisting of: an agent according to formula I, an agent according to formula II, phytocannabinoids, cannabidiol (CBD) and its analogues cannabidivarin (CBDV), cannabiodiolic acid (CBDA), cannabigerol (CBG) and its analogues CBGA and CBGV, Δ9-tetrahydrocannabinol (Δ9-THC) and its analogue THCV, cannabinol (CBN), N-acylethanolamines, palmitoylethanolamide (PEA), omega-3 fatty acids, phosphatidylserine, rosmarinic acid, guanfacine, a noradrenaline agonist, clonidine, antipsychotic drugs, HU-308, BCP, pimozide, haloperidol, aripiprazole, a dopamine-depleting agent tetrabenazine, an acetylcholine release blocker, botulinum toxin, a benzodiazepine, a stimulant and a dopamine/norepinephrine reuptake inhibitor, methylphenidate, amphetamine and its analogues, lisdexamfetamine, atomoxetine, an SSRI, wherein the SSRI is selected from the group consisting of fluoxetine, sertraline, citalopram, escitalopram, fluvoxamine and paroxetine and combinations thereof, and any combination of the foregoing.

In some embodiments, the fixed drug combination composition comprises a therapeutically effective amount of an agent according to formula I, combined with a therapeutically effective amount of at least one additional active agent according to formula II or combinations thereof.

In some embodiments, there is provided the above method of treatment of a disorder and composition, wherein, in the fixed drug combination composition, the agent of formula I is 4'-O-methylhonokiol and the agent of formula II is raloxifene.

In some embodiments, there is provided the above method of treatment of a disorder and composition, wherein, in the fixed drug combination composition, the agent of formula I is 4'-O-methylhonokiol and the at least one additional active agent is rosmarinic acid.

In some embodiments, there is provided the above method of treatment of a disorder, wherein, in said fixed drug combination, the agent of formula II is raloxifene and the at least one additional active agent is rosmarinic acid.

In some embodiments, there is provided the above method of treatment of a disorder, and composition wherein, in the fixed drug combination composition, the active agent of formula I is 4'-O-methylhonokiol and the at least one additional active agent is an omega-3 fatty acid.

In some embodiments, there is provided the above method of treatment of a disorder and composition, wherein, in the fixed drug combination composition, the active agent of formula II is raloxifene and the at least one additional active agent is an omega-3 fatty acid.

In some embodiments, there is provided the above method of treatment of a disorder and composition, wherein, in the fixed drug combination composition, the agent of formula I is 4'-O-methylhonokiol and the at least one additional active agent is a stimulant drug.

In some embodiments, the stimulant drug is selected from the group consisting of dopamine/norepinephrine reuptake inhibitor, methylphenidate, amphetamine and its analogues, lisdexamfetamine, atomoxetine and combinations thereof.

In some embodiments, there is provided the above method of treatment of a disorder and composition, wherein the active agent of formula I in the fixed drug combination is 4'-O-methylhonokiol and the at least one additional active agent is selected from Δ9-tetrahydrocannabinol (Δ9-THC) and its analogue THCV.

In some embodiments, there is provided the above method of treatment of a disorder and composition, wherein, in the fixed drug combination, the agent of formula I is 4'-O-methylhonokiol and the at least one additional active agent is a combination of Δ9-tetrahydrocannabinol (Δ9-THC) and palmitoylethanolamide (PEA).

In some embodiments, there is provided the above method of treatment of a disorder, wherein, in the fixed drug combination, the agent of formula I is 4'-O-methylhonokiol and the at least one additional agent is cannabidiol (CBD) or its analogue CBDV.

In some embodiments, there is provided the above method of treatment of a disorder and composition, wherein the agent of formula I is 4'-O-methylhonokiol and the at least one additional active agent is selected from CBD and Δ9-tetrahydrocannabinol (Δ9-THC) or mixtures thereof.

In some embodiments, there is provided a method of treatment of any one of the above disorders, wherein acute, transient or chronic, according to any one of the methods detailed above, the method comprising administering to a subject in need thereof a therapeutically effective dose of a pharmaceutical composition comprising at least one active agent selected from the group of CB2 receptor selective agonists, such as HU-308, BCP and mixtures thereof, and wherein the CB2 receptor in a subject is absolutely dysfunctional.

In some embodiments, the subject in need thereof is a human or a non-human animals including but not limited to mammals.

In some embodiments, there is provided a method of treatment, comprising administering a composition, wherein the composition comprises two or more active agents, wherein administration of the two or more active agents to a subject in need thereof exhibits at least one improved therapeutic effect as compared to the effect obtained by a single active agent administered at the same concentration, wherein the improved effect is selected from an enhanced therapeutic effect, a reduced psychoactive effect, an enhanced therapeutic effect and a reduced psychoactive effect in the subject.

In some embodiments, there is provided a method of treatment according to any one of the methods detailed above, wherein the therapeutically effective dose of the least one active agent is formulated in a pharmaceutically acceptable carrier.

In some embodiments, there is provided a composition comprising at least one active agent selected from formula I, formula II, 4'-O-methylhonokiol, raloxifene, JTE 907, SR 144528, HU-308, BCP and combinations thereof, and wherein the composition is formulated in a self-emulsifying carrier.

In some embodiments, there is provided a composition comprising at least one active agent selected from formula I, formula II, 4'-O-methylhonokiol, raloxifene, JTE 907, SR 144528, HU-308, BCP and combinations thereof, wherein the composition is formulated in a self-emulsifying carrier and wherein the self-emulsifying carrier is selected from Table I.

In some embodiments, there is provided a composition comprising at least one active agent selected from formula I, formula II, 4'-O-methylhonokiol, raloxifene, JTE 907, SR 144528, HU-308, BCP and combinations thereof, wherein the composition is formulated as a stable self-emulsifying drug delivery system and wherein the composition comprises at least one oil, at least one surfactant HLB<9, at least one surfactant HLB>13, at least one co-surfactant, at least one antioxidant or free-radical scavenger.

In some embodiments, there is provided the above composition wherein the composition is formulated as a stable self-emulsifying drug delivery system and wherein the composition comprises: from 10% w/w to 50% w/w of an oil selected from the group consisting of medium chain triglycerides, propylene glycol dicaprilate/dicaprate, medium chain mono- and diglycerides, acetylated mono- and diglycerides, sesame oil and olive oil and combinations thereof, from 20% w/w to 50% w/w of a surfactant HLB<9 selected from the group consisting of oleoyl polyoxyl-6 glycerides, linoleyl polyoxyl-6 glycerides (20-40%), Polysorbate 85 (Tween-85) polyoxyethylene (20-40% w/w), sorbitan trioleate (5-15% w/w), Span-80 (sorbitan monooleate) (5-25% w/w), polyglyceryl-3 dioleate (15-35% w/w) and glycerin monolinoleate (10-35% w/w), Polysorbate 80 (Tween-80) polyoxyethylene (20-40% w/w), Polysorbate 60 (Tween-60) polyoxyethylene (20-40% w/w), and combinations thereof, from 5% w/w to 50 w/w of a surfactant HLB>13 selected from the group consisting of polyoxylated castor oil (5-40% w/w), PEG 40 hydrogenated castor oil, PEG-15 hydroxystearate (5-25% w/w), caprylocaproyl polyoxyl-8 glycerides (10-20% w/w) and combinations thereof, from 5% w/w to 25% w/w of a surfactant HLB>13 selected from the group consisting of PEG-20 sorbitan monostearate, PEG-20 sorbitan monooleate (5-25%), PEG 40 stearate (5-25% w/w) and combinations thereof, from 0.5% w/w to 15 w/w of a co-surfactant selected from the group consisting of any lecithin (2-15% w/w), soy lecithin (>75% w/w phosphatidylcholine in oil, 1-10% w/w), soy lecithin PC content >50% (2-15% w/w), egg lecithin E-60 (1-5% w/w), egg lecithin E-80 (1-5% w/w), distearoylphosphatidylcholine (0.5-3% w/w) and combinations thereof, from 0.1% w/w to 5 w/w of an antioxidant or free radical scavenger selected from the group consisting of d-alpha-tocopherol (1-10% w/w), dl-alphatocopherol (2-15% w/w), dl-alpha-tocopheryl acetate (2-15% w/w), mixed tocopherols (alpha, beta, gamma—1-10% w/w), d-alpha-tocopheryl acetate (2-15% w/w), butylated hydroxyanisole (BHA, 0.01-0.5% w/w), tocophersolan (TPGS, tocopherol PEG ester succinate) (2-10% w/w) and combinations thereof, from about 1% w/w to about 10% w/w of ethyl alcohol, and from 1% w/w to 20% w/w of at least one active agent.

In some embodiments, there is provided the above composition, wherein the composition is formulated as a stable self-emulsifying drug delivery system and wherein the composition comprises:

from 30% w/w to 50% w/w capric/caprylic triglycerides,
from 30% w/w to 50% w/w oleoyl polyoxyl-6 glycerides,
from 5% w/w to 35 w/w polyoxylated castor oil,
from 7% w/w to 15% w/w PEG-20 sorbitan monostearate,
from 2% w/w to 10% w/w soy lecithin (75% phosphatidylcholine in oil),
from 1% w/w to 15 w/w d-alpha tocopherol and/or tocopherol acetate,
from 1% w/w to 20% w/w of at least one active agent.

In some embodiments, the pharmaceutical composition is formulated in a dosage form selected from the group consisting of a solution, suspension, emulsion, powder, tablet, caplet, capsule, dragee, depot, granules, syrup, transdermal patch, spray, gastroresistant oral dosage, gastroresistant softgel capsule, cream, nasal dosage, sublingual dosage and suppository.

In some embodiments, the pharmaceutical composition is formulated for oral, inhalation, transdermal, vaginal and/or rectal administration routes.

In some embodiments, there is provided pharmaceutical compositions and methods of treatment of a disease or a disorder selected from ADHD (Attention-deficit hyperactivity disorder), Tourette syndrome (TS), a tic disorder, a vocal disorder, obsessive-compulsive disorder (OCD), developmental coordination disorder, stereotypic movement disorder, autism spectrum disorders, bacterial-induced repetitive behavior, NMDA antibody-related encephalitis, autoimmune antibody-mediated mental disorder, autoimmune antibody-mediated psychosis, pediatric autoimmune neuropsychiatric disorders associated with streptococcal infections (PANDAS), chorea (Sydenham's chorea (SC), chorea minor, chorea gravidarum, drug-induced chorea), drug-induced repetitive behaviors, akathisia, dyskinesias, dystonias, cramps and spasms, tremors, restless leg syndrome, moving toes/fingers syndrome, involuntary movement, stereotypic movement disorder, extrapyramidal movement disorders, Wernicke-Korsakoff syndrome, Parkinson's disease, amyotrophic lateral sclerosis, Alzheimer's disease, Huntington's disease, multiple sclerosis, epilepsy, seizures, diabetes, insulin resistance, hypertension, pain, anesthesia, inflammation, convulsions, infertility, aging, schizophrenia, schizoaffective disorder, bipolar disorder I and II, unipolar disorder, multiple personality disorder, psychotic disorders, depression, psychotic depression, depressive disorders, major depressive disorder, epilepsy, anxiety disorders, autistic spectrum disorder, enuresis, addiction, withdrawal symptoms associated with addiction, Asperger syndrome, oppositional defiant disorder, behavioral disturbance, agitation, psychosis/agitation associated with Alzheimer's disease, psychosis associated with Parkinson's disease, psychosis associated with drug of abuse, psychosis associated with psychedelic drug abuse, LSD-induced psychosis, steroid-induced schizophrenia, steroid-induced psychosis, Capgras syndrome, Fregoli syndrome, Cotard, personality disorders, borderline personality disorder, avoidant personality disorder, mania, dementia, anorexia, anorexia nervosa, eating disorders, narcolepsy, anxiety, generalized anxiety disorder, social anxiety disorder, body dismographic disorder, paranoid disorder, nightmares, agitation, post-traumatic stress disorder (PTSD), severe mood dysregulation, developmental coordination disorder, neuroinflammatory diseases, neurodegenerative diseases, liver associated-diseases, hepatitis, alcohol-related liver disease, fibromyalgia, gastrointestinal diseases, inflammatory bowel disease, Crohn's disease, ulcerative colitis, cancer, depression or anxiety that leads to metabolic diseases, metabolic diseases, infertility, cardiovascular diseases, osteoporosis, traumatic brain injury, cerebral ischemia, depression associated with any of the above clinical conditions, anxiety associated with any of the above clinical conditions, hyperactivity associated with any of the above clinical conditions, inattention associated with any of the above clinical conditions, involuntary movements associated with any of the above clinical conditions, cognitive deficits associated with any of the above clinical conditions, and combinations thereof, wherein the disorder is acute, transient or chronic disease, wherein comprising administering a therapeutically effective amount of the above self-emulsifying composition to a subject in need thereof, comprising at least one active agent selected from formula I, formula II and combinations thereof.

In some embodiments, there is provided a composition comprising at least one active agent selected from formula I, formula II and combinations thereof, for the treatment of a disease or a disorder selected from ADHD (Attention-deficit hyperactivity disorder), Tourette syndrome (TS), a tic disorder, a vocal disorder, obsessive-compulsive disorder (OCD), developmental coordination disorder, stereotypic movement disorder, autism spectrum disorders, bacterial-induced repetitive behavior, NMDA antibody-related encephalitis, autoimmune antibody-mediated mental disorder, autoimmune antibody-mediated psychosis, pediatric autoimmune neuropsychiatric disorders associated with streptococcal infections (PANDAS), chorea (Sydenham's chorea (SC), chorea minor, chorea gravidarum, drug-induced chorea), drug-induced repetitive behaviors, akathisia, dyskinesias, dystonias, cramps and spasms, tremors, restless leg syndrome, moving toes/fingers syndrome, involuntary movement, stereotypic movement disorder, extrapyramidal movement disorders, Wernicke-Korsakoff syndrome, Parkinson's disease, amyotrophic lateral sclerosis, Alzheimer's disease, Huntington's disease, multiple sclerosis and combinations thereof, wherein acute, transient or chronic, epilepsy, seizures, diabetes, insulin resistance, hypertension, pain, anesthesia, inflammation, convulsions, infertility, aging, schizophrenia, schizoaffective disorder, bipolar disorder I and II, unipolar disorder, multiple personality disorder, psychotic disorders, depression, psychotic depression, depressive disorders, major depressive disorder, epilepsy, anxiety disorders, autistic spectrum disorder, enuresis, addiction, withdrawal symptoms associated with addiction, Asperger syndrome, oppositional defiant disorder, behavioral disturbance, agitation, psychosis/agitation associated with Alzheimer's disease, psychosis associated with Parkinson's disease, psychosis associated with drug of abuse, psychosis associated with psychedelic drug abuse, LSD-induced psychosis, steroid-induced schizophrenia, steroid-induced psychosis, Capgras syndrome, Fregoli syndrome, Cotard, personality disorders, borderline personality disorder, avoidant personality disorder, mania, dementia, anorexia, anorexia nervosa, eating disorders, narcolepsy, anxiety, generalized anxiety disorder, social anxiety disorder, body dismographic disorder, paranoid disorder, nightmares, agitation, post-traumatic stress disorder (PTSD), severe mood dysregulation, developmental coordination disorder, neuroinflammatory diseases, neurodegenerative diseases, liver associated-diseases, hepatitis, alcohol-related liver disease, fibromyalgia, gastrointestinal diseases, inflammatory bowel disease, Crohn's disease, ulcerative colitis, cancer, depression or anxiety that leads to metabolic diseases, metabolic diseases, infertility, cardiovascular diseases, osteoporosis, traumatic brain injury, cerebral ischemia, depression associated with any of the above clinical conditions, anxiety associated with any of the above clinical conditions, hyperactivity associated with any of the above clinical conditions, inattention associated with any of the above clinical conditions, involuntary movements associated with any of the above clinical conditions, cognitive deficits associated with any of the above clinical conditions, and combinations thereof, wherein the disorder is acute, transient or chronic disease, with the proviso that when the at least one active agent has formula I and is the sole active agent, the disorder is not Tourette syndrome or tic disorder, or when the at least one active agent has formula II and is the sole active agent, the disorder is not OCD.

In some embodiments, there is provided a method of treatment of the above diseases or disorders, wherein the at least one active agent is selected from the group consisting of, HU-308, BCP and combinations thereof.

In some embodiments, the composition comprises a self-emulsifying carrier.

In some embodiments, the composition is formulated in a dosage form selected from the group consisting of a solution, suspension, emulsion, powder, tablet, caplet, capsule, dragee, depot, granules, syrup, transdermal patch, spray, gastroresistant oral dosage, gastroresistant softgel capsule, cream, nasal dosage, sublingual dosage and suppository.

In some embodiments, the composition is formulated for oral, inhalation, transdermal, vaginal and/or rectal administration routes.

In some embodiments, there is provided the above method of treatment of the above diseases or disorders, wherein the composition is formulated as an injectable solution and wherein the composition is administered as intravenous injection, intra-arterial injection, intramuscular injection, intradermal injection, intraperitoneal injection, intrathecal injection, depot injection or subcutaneous injection.

In some embodiments, there is provided a method of treatment of the above diseases or disorders, wherein the therapeutically effective amount of the at least one active agent in the composition administered to a human or non-human subject in need thereof is in a range selected from about 0.0001-0.005 mg/kg, 0.005-0.01 mg/kg, about 0.01-0.1 mg/kg, 0.1-2 mg/kg, about 2-5 mg/kg, about 5-10 mg/kg, about 10-30 mg/kg, about 30-100 mg/kg, about 100-1000 mg/kg and about 1000-6000 mg/kg according to the patient's age, subject's age, subject's species, composition's effectiveness, active agent and the mode of administration.

In some embodiments, there is provided a method of treatment of a human or non-human subject in need thereof, wherein the subject has a mental, movement or behavioral disorder with a composition formulated as a capsule or an injection, for example but not limited to intramuscular injection, wherein the composition comprises an active agent in a range selected from the group consisting of 0.0001-0.01 mg, 0.01-0.1 mg, 0.1-10 mg, 10-100 mg, 100-200 mg, 200-300 mg, 300-400 mg, 500-600 mg, 600-700 mg, 700-800 mg or 800-1000 mg, 1000-1500 mg, 1000-2000 mg, 2000-5000 mg, 5000-10000 mg according to the patient's age, subject's age, subject's species, composition's effectiveness, active agent and the mode of administration.

In some embodiments, there is provided a method of treatment of a human or non-human subject in need thereof having a mental, movement or behavioral disorder with a delayed-release composition (such as compositions for a slow-release, slow-acting form of medication prepared as a capsule or a depot injection given for example but not limited by intramuscular injection, which are administrated every 1 week or once a month to up to every six months) of the present disclosure wherein the average amount of a single administration of an active agent administered is in a range selected from the group consisting of 0.0001-0.01 mg, 0.01-0.1 mg, 0.1-10 mg, 10-100 mg, 100-200 mg, 200-300 mg, 300-400 mg, 500-600 mg, 600-700 mg, 700-800 mg or 800-1000 mg, 1000-1500 mg, 1000-2000 mg, 2000-5000 mg, 5000-10000 mg according to the patient's age, subject's age, subject's species, composition's effectiveness, active agent and the mode of administration.

In some embodiments, there is provided a method of treatment of a patient or a subject in need thereof, wherein the patient has a mental, movement or behavioral disorder with a composition formulated as a capsule or an injection, for example but not limited to intramuscular injection, wherein the composition comprises 4-0-methylhonokiol (MH) or raloxifene or HU-308 or BCP in a range selected from the group consisting of 0.0001-0.01 mg, 0.01-0.1 mg, 0.1-10 mg, 10-100 mg, 100-200 mg, 200-300 mg, 300-400 mg, 500-600 mg, 600-700 mg, 700-800 mg or 800-1000 mg, 1000-1500 mg, 1000-2000 mg, 2000-5000 mg, 5000-10000 mg according to the patient's age, subject's age, subject's species, composition's effectiveness, active agent and the mode of administration.

In some embodiments, there is provided a method of treatment of a patient or a subject in need thereof having a mental, movement or behavioral disorder with a delayed-release composition (such as compositions for a slow-release, slow-acting form of medication prepared as a capsule or a depot injection given for example but not limited by intramuscular injection, which are administrated every 1 week or once a month to up to every six months) 5 of the present disclosure wherein the average amount of a single administration of 4-O-methylhonokiol (MH) or raloxifene or HU-308 or BCP administered is in a range selected from the group consisting of 0.0001-0.01 mg, 0.01-0.1 mg, 0.1-10 mg, 10-100 mg, 100-200 mg, 200-300 mg, 300-400 mg, 500-600 mg, 600-700 mg, 700-800 mg or 800-1000 mg, 1000-1500 mg, 1000-2000 mg, 2000-5000 mg, 5000-10000 mg according to the patient's age, subject's age, subject's species, composition's effectiveness, active agent and the mode of administration.

According to an embodiment, there is provided a method of treatment of a mental, movement or behavioral disorder in a patient in need thereof with a composition of the present disclosure.

In some embodiments, the subject in need thereof is a human subject or a non-human animal or mammal. In some embodiments, the composition comprising the therapeutically effective dose of at least one active agent in a pharmaceutically effective carrier is administered to a human or non-human subject in need thereof once every 6 months, once every 3 months to about once a month, once a week, about 3 times per day, once per week, twice per week, 3 times per week, 4 times per week, 5 times per week, 6 times per week, once per day, twice per day or 3 times per day or 4 times per day.

In some embodiments, the subject in need thereof is an adult patient, a teenage patient or pediatric patient.

Some aspects of the invention relate to a method of screening for a candidate active agent for the treatment of a mental disease, comprising operatively linking a reporter gene which expresses a detectable protein to a regulatory sequence for a gene selected from the group consisting of genes encoding CB1 receptor, CB2 receptor, GPR55, GPR18, GPR119, GABAA receptors, GABAB receptors, cyclooxygenase (COX) enzyme, COX-1, COX-2, COX-3 enzymes and combinations thereof, to produce a reporter construct; transfecting a cell with the reporter construct; exposing the transfected cell to a candidate active agent; and comparing the level of expression or function of the receptor before vs. after exposure to the candidate active agent, wherein an alteration in the level of expression after exposure is indicative of the candidate active agent being useful for the treatment of a mental disease.

Some aspects of the invention relate to a kit comprising a custom array selected from a gene array, a probe array, a protein array, an array comprising a therapeutic agent, an array comprising a nucleic acid molecule which selectively hybridizes to a nucleic acid molecule, an array comprising a radioligand agent, an array comprising a cell or a kit component which expresses a patient's mutation, to at least one of the genes selected from genes encoding CB1 receptor, CB2 receptor, GPR55, GPR18, GPR119, GABAA receptors, GABAB receptors, COX-1, COX-2, COX-3 enzymes and combination thereof, and instructions for use it in a combination with other genes, proteins or combination thereof.

In some embodiments, there is provided a kit comprising a pharmaceutical composition of this invention and instructions for use and optionally comprising a subject sample harvested from a body fluid selected from cerebrospinal fluid (CSF), blood, saliva, lymphatic fluid, urine or feces, or from a body organ selected from epithelial cells, spleen, skin, hair, spinal cord and brain.

BRIEF DESCRIPTION OF THE FIGURES

FIG. 4A) and showing that MH alone had no effect on head twitches in mice vs. control group which received vehicle and saline (n=3 in each group) (FIG. 4B).

FIG. 7A) and reduced compulsive behavior, JTE 907 reduced the number of buried marble (n=6 in each group; FIG. 7B).

DETAILED DESCRIPTION OF THE INVENTION

Definitions

Figure 1:
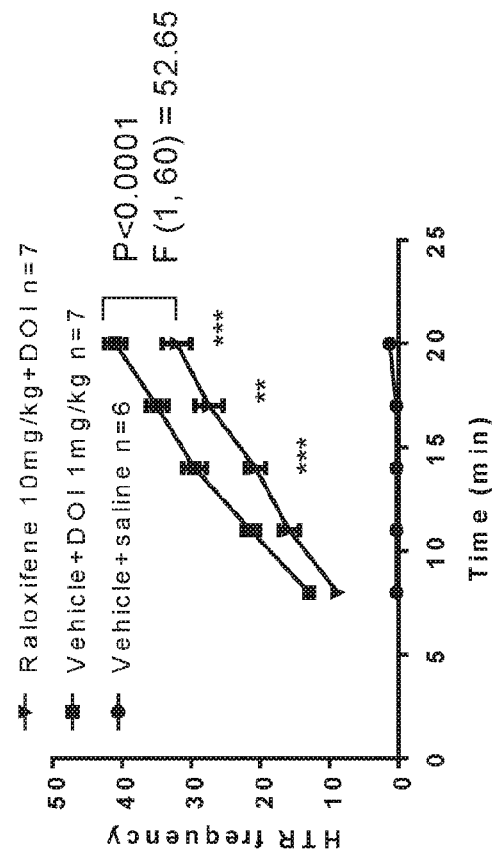
FIG. 1 is a line graph showing that raloxifene reversed the effect of DOI on head twitch frequency.

The term "CB2 receptor inverse agonist" refers to a ligand which binds to CB2 receptors in cells expressing CB2 receptors and increases cAMP production in these cells in the absence of any known CB2 receptor agonist. A typical assay for determining CB2 receptor inverse agonist utilizes CHO cells transfected with CB2 receptors and measuring cAMP production in the absence or presence of a test compound or in the presence of forskolin (activated) (see, for example, Schuehly et al., 2011). It is to be understood that a CB2 receptor agonist inhibits cAMP production in cells expressing CB2 receptors. In the presence of a CB2 receptor agonist, the CB2 receptor inverse agonist reduces CB2 receptor agonistic activity, i.e., inhibition of cAMP production, and as such the CB2 receptor inverse agonist behaves as a CB2 receptor antagonist. Additionally, or alternatively, the CB2 receptor inverse agonist may modulate or shift one or more activities mediated by the CB2 receptor, for example, intracellular $Ca^{2+}$ concentration. Thus, a CB2 receptor inverse agonist which 30 increases cAMP production can exhibit full or partial agonistic effect including, but not limited to, intracellular Ca2+ concentration, and as such it is referred to as a CB2 receptor mixed-type agonist. MH, for example, is known to be a CB2 receptor inverse agonist/mixed-type agonist due to its dual effects: increasing cAMP production and increasing intracellular Ca2+ concentration.

The term "inverse agonistic effect" means a partial or full inhibitory effect on CB2 receptor agonistic activity including, but not limited to, cAMP production, which effect reduces or inhibits the efficacy of any known CB2 receptor agonist and/or reduces the potency of any known CB2 receptor agonist. Typically, an inverse agonistic effect of a CB2 receptor ligand can be measured at a concentration of about 0.1 nM to about 10 µM.

The term "CB2 receptor partial agonist" means a ligand which binds to and activates the CB2 receptor but, relative to a full agonist, has only partial efficacy at the receptor. The partial agonist can be considered a ligand which displays both agonistic and antagonistic effects when both ligands, a full agonist and a partial agonist are present, the partial agonist can act as an antagonist, competing with the full agonist for receptor occupancy and producing a net decrease in receptor activation observed with the full agonist alone.

The term "omega-3 fatty acid" means any polyunsaturated fatty acid (PUFA) with a double bond (C=C) at the third carbon atom from the end of the carbon chain. The term includes, but not limited to, α-linolenic acid (ALA), eicosapentaenoic acid (EPA) and docosahexaenoic acid (DHA). In "omega-3 fatty acid" the ratio of EPA to DHA can be between 1:1 to 10:1, about 1:1, about 2:1, about 3:1, about 4:1, 5:1 about, about 6:1, about 7:1 about 8:1, about 9:1, about 10:1. Each possibility is a separate embodiment of the invention.

The term "negative allosteric modulator" means a ligand which binds to a putative allosteric site/s of the CB2 receptor, distinct from the orthosteric sites (binding sites of the endogenous agonists), and increases cAMP production compared to cAMP production in its absence, thus reducing CB2 receptor agonistic activity.

The term "alkyl" is intended to include linear, branched, or cyclic hydrocarbon structures and combinations thereof. Examples of lower alkyl groups include, but are not limited to, methyl, ethyl, propyl, isopropyl, butyl, s- and t-butyl and the like. Cycloalkyl is a subset of alkyl and includes cyclic hydrocarbon groups of from 3 to 8 carbon atoms. Examples of cycloalkyl groups include cyclopropyl, cyclobutyl, cyclopentyl, cyclohexyl and the like.

The terms "substituted alkyl" and "substituted cycloalkyl" are intended to include substitution of a hydrogen with a halogen atom. The "halogen atom" means a fluorine atom, a chlorine atom, a bromine atom, or an iodine atom.

The terms "comprising", "including", "having" and grammatical variants thereof are to be taken as specifying the stated features, steps or components but do not preclude the addition of one or more additional features, steps, or components thereof.

As used herein, the indefinite articles "a" and "an" mean "at least one" or "one or more" unless the context clearly dictates otherwise.

As used herein, when a numerical value is preceded by the term "about", the term "about" is intended to indicate +/−10%.

The term "treating" includes curing and/or preventing a condition, curing and/or ameliorating symptoms of a condition.

The term "pharmaceutically acceptable" means approved by a regulatory agency of the U.S. Federal or a U.S. state government or listed in the U.S. Pharmacopeia or other generally recognized pharmacopeia for use in animals, and more particularly in humans. Herein, the phrase "pharmaceutically acceptable carrier" refers to an approved carrier or a diluent that does not cause significant irritation to a subject and does not abrogate the biological activity and properties of the active agent.

The term "therapeutically effective amount" means that amount of the compound being CB2 receptor inverse agonist and/or CB2 receptor mixed-type agonist and/or negative allosteric modulator which is sufficient to provide a beneficial effect to the subject to which the inverse agonist and/or mixed-type agonist and/or negative allosteric modulator is administered.

The term "carrier" refers to a diluent, adjuvant, excipient, or vehicle with which the active agent is administered. Herein the term "excipient" refers to an inert substance added to a pharmaceutical composition to further facilitate processes and administration of the active agent. The terms "carrier" and "vehicle" are used interchangeably.

Aspects of the present invention provide methods of treatment of disorders, comprising a mental, movement or behavioral disorder. Some of the above disorders exhibit a repetitive phenotype.

In some embodiments, there is provided a method of treatment of a disorder selected from the group consisting of developmental coordination disorder, stereotypic movement disorder, autism spectrum disorders, obsessive-compulsive disorder (OCD), bacterial-induced repetitive behavior, pediatric autoimmune neuropsychiatric disorders associated with streptococcal infections (PANDAS), chorea (Sydenham's chorea (SC), chorea minor, chorea gravidarum, drug-induced chorea), drug-induced repetitive behaviors, akathisia, dyskinesias, dystonias, cramps and spasms, tremors, restless leg syndrome, moving toes/fingers syndrome, involuntary movement, extrapyramidal movement disorders, Wernicke-Korsakoff syndrome and combinations thereof, wherein acute, transient or chronic, the method comprising administering to a human or non-human subject in need thereof a therapeutically effective dose of a pharmaceutical composition comprising at least one active agent selected from the group of CB2 receptor inverse agonists and mixed CB2/SERM ligands consisting of (i) a CB2 receptor inverse agonist of formula I:

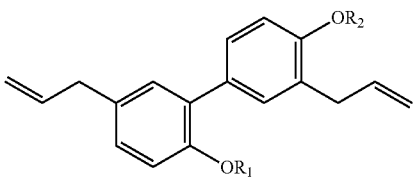

or a salt thereof and a pharmaceutically acceptable carrier, wherein R1 and R2 are each independently selected from the group consisting of hydrogen, C1-C8 alkyl, C3-C8 cycloalkyl, C1-C8 haloalkyl, or C3-C8 cyclohaloalkyl, wherein R1 and R2 are not both hydrogen (ii) a mixed CB2/SERM ligand of formula II

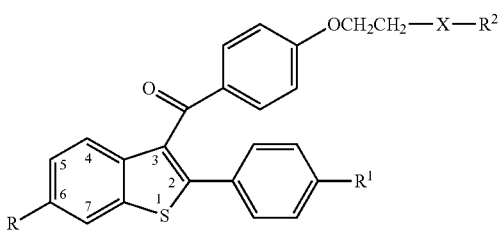

wherein

X is a bond, CH$_2$, or CH$_2$CH$_2$;

R and R$^1$, independently, are hydrogen, hydroxyl, C$_1$-C$_6$ alkoxy, C$_1$-C$_6$-acyloxy, C$_1$-C$_6$-alkoxy-C$_2$-C$_6$-acyloxy, R$_3$-substituted aryloxy, R$_3$-substituted aroyloxy, R$^4$-substituted carbonyloxy, chloro, or bromo;

R$^2$ is a heterocyclic ring selected from the group consisting of pyrrolidino, piperidino, or hexamethyleneimino;

R$^3$ is C$_1$-C$_3$-alkyl, C1-C3-alkoxy, hydrogen, or halo; and

R$^4$ is C$_1$-C$_6$-alkoxy or aryloxy; or a pharmaceutically acceptable salt thereof;

(iii) the CB2 receptor inverse agonist N-(benzo[1,3]dioxol-5-ylmethyl)-7-methoxy-2-oxo-8-pentyloxy-1,2-dihydroquinoline-3-carboxamide (JTE 907), (iv) the CB2 receptor inverse agonist 5-(4-Chloro-3-methylphenyl)-1-[(4-methylphenyl)methyl]-N-[(1S, 2S,4R)-1,3,3-trimethylbicyclo[2.2.1]heptan-2-yl]-1H-pyrazole-3-carboxamide (SR 144528) or (v) any combination of (i)-(iv);

wherein active agents (i)-(v) are formulated in a pharmaceutically effective carrier. In some embodiments, when the active agent has formula II and is the sole active agent, the disorder is not OCD.

Aspects of the present invention provide pharmaceutical compositions comprising a CB2 receptor inverse agonist of formula I, a mixed CB2/SERM ligand of formula II, a combination of a CB2 receptor inverse agonist of formula I and a mixed CB2/SERM ligand of formula II for the treatment of a disorder selected of ADHD (Attention-deficit hyperactivity disorder), Tourette syndrome (TS), a tic disorder, a vocal disorder, developmental coordination disorder, stereotypic movement disorder, autism spectrum disorders, bacterial-induced repetitive behavior, NMDA antibody-related encephalitis, autoimmune antibody-mediated mental disorder, autoimmune antibody-mediated psychosis, pediatric autoimmune neuropsychiatric disorders associated with streptococcal infections (PANDAS), chorea (Sydenham's chorea (SC), chorea minor, chorea gravidarum, drug-induced chorea), drug-induced repetitive behaviors, akathisia, dyskinesias, dystonias, cramps and spasms, tremors, restless leg syndrome, moving toes/fingers syndrome, involuntary movement, stereotypic movement disorder, extrapyramidal movement disorders, Wernicke-Korsakoff syndrome, Parkinson's disease, amyotrophic lateral sclerosis, Alzheimer's disease, Huntington's disease, multiple sclerosis and combinations thereof, wherein acute, transient or chronic, epilepsy, seizures, diabetes, insulin resistance, hypertension, pain, anesthesia, inflammation, convulsions, infertility, aging, schizophrenia, schizoaffective disorder, bipolar disorder I and II, unipolar disorder, multiple personality disorder, psychotic disorders, depression, psychotic depression, depressive disorders, major depressive disorder, epilepsy, anxiety disorders, autistic spectrum disorder, enuresis, addiction, withdrawal symptoms associated with addiction, Asperger syndrome, oppositional defiant disorder, behavioral disturbance, agitation, psychosis/agitation associated with Alzheimer's disease, psychosis associated with Parkinson's disease, psychosis associated with drug of abuse, psychosis associated with psychedelic drug abuse, LSD-induced psychosis, steroid-induced schizophrenia, steroid-induced psychosis, Capgras syndrome; Fregoli syndrome, Cotard, personality disorders, borderline personality disorder, avoidant personality disorder, mania, dementia, anorexia, anorexia nervosa, eating disorders, narcolepsy, anxiety, generalized anxiety disorder, social anxiety disorder, body dismographic disorder, paranoid disorder, nightmares, agitation, post-traumatic stress disorder (PTSD), severe mood dysregulation, developmental coordination disorder, neuroinflammatory diseases, neurodegenerative diseases, liver associated-diseases, hepatitis, alcohol-related liver disease, fibromyalgia, gastrointestinal diseases, inflammatory bowel disease, Crohn's disease, ulcerative colitis, cancer, depression or anxiety that leads to metabolic diseases, metabolic diseases, infertility, cardiovascular diseases, osteoporosis, traumatic brain injury, cerebral ischemia, depression associated with any of the above clinical conditions, anxiety associated with any of the above clinical conditions, hyperactivity associated with any of the above clinical conditions, inattention associated with any of the above clinical conditions, involuntary movements associated with any of the above clinical conditions, cognitive deficits associated with any of the above clinical conditions, and combinations thereof, wherein the disorder is acute, transient or chronic disease, wherein comprising administering a therapeutically effective amount of the pharmaceutical compositions in a self-emulsifying carrier to a human or non-human subject in need thereof, comprising at least one active agent selected from formula I, formula II and combinations thereof.

The present invention further provides pharmaceutical compositions comprising a CB2 receptor inverse agonist of formula I, a mixed CB2/SERM ligand of formula II, a combination of a CB2 receptor inverse agonist of formula I and a mixed CB2/SERM ligand of formula II in a self-emulsifying carrier for the treatment of the above disorders.

The present invention further provides pharmaceutical compositions in a self-emulsifying carrier comprising 4'-O-methylhonokiol and/or raloxifene and its derivatives for the treatment of the above disorders.

The present invention further provides pharmaceutical compositions in a self-emulsifying carrier comprising HU-308 and/or beta-caryophyllene (BCP) for the treatment of the above disorders.

Also provided are cannabinoid type 2 (CB2) receptor inverse agonists and their combinations with phytocannabinoids, cannabidiol (CBD), Δ$^9$-tetrahydrocannabinol (Δ$^9$-THC), cannabinol (CBN), cannabigerol (CBG), N-acylethanolamines and their analogues and derivatives, omega-3 fatty acids, phosphatidylserine, rosmarinic acid, guanfacine, noradrenaline agonists, antipsychotic drugs, dopamine-depleting agent, acetylcholine release blockers, benzodiazepines, stimulants, dopamine/norepinephrine reuptake inhibitors and selective serotonin reuptake inhibitors (SSRIs) for treating or ameliorating behaviors that are comorbid with ADHD (Attention-deficit hyperactivity disorder), Tourette syndrome (TS), tic disorder, vocal disorder, developmental coordination disorder, stereotypic movement disorder, autism spectrum disorders, obsessive-compulsive disorder (OCD), bacterial-induced repetitive behavior, pediatric autoimmune neuropsychiatric disorders associated with streptococcal infections (PANDAS), chorea (Sydenham's chorea (SC), chorea minor, chorea gravidarum, drug-induced chorea), drug-induced repetitive behaviors, akathisia, dyskinesias, dystonias, cramps and spasms, tremors, restless leg syndrome, moving toes/fingers syndrome, involuntary movement, stereotypic movement disorder, extrapyramidal movement disorders, Wernicke-Korsakoff syndrome and combinations thereof, wherein acute, transient or chronic.

Also provided are cannabinoid type 2 (CB2) receptor selective agonists selected of HU-308 and BCP and their combinations with phytocannabinoids, cannabidiol (CBD), $\Delta^9$-tetrahydrocannabinol ($\Delta^9$-THC), cannabinol (CBN), cannabigerol (CBG), N-acylethanolamines and their analogues and derivatives, omega-3 fatty acids, phosphatidylserine, rosmarinic acid, guanfacine, noradrenaline agonists, antipsychotic drugs, dopamine-depleting agent, acetylcholine release blockers, benzodiazepines, stimulants, dopamine/norepinephrine reuptake inhibitors and SSRIs for treating a disorder selected of or ameliorating behaviors associated with ADHD (Attention-deficit hyperactivity disorder), Tourette syndrome (TS), tic disorder, vocal disorder, developmental coordination disorder, stereotypic movement disorder, autism spectrum disorders, obsessive-compulsive disorder (OCD), bacterial-induced repetitive behavior, pediatric autoimmune neuropsychiatric disorders associated with streptococcal infections (PANDAS), chorea (Sydenham's chorea (SC), chorea minor, chorea gravidarum, drug-induced chorea), drug-induced repetitive behaviors, akathisia, dyskinesias, dystonias, cramps and spasms, tremors, restless leg syndrome, moving toes/fingers syndrome, involuntary movement, stereotypic movement disorder, extrapyramidal movement disorders, Wernicke-Korsakoff syndrome and combinations thereof, wherein acute, transient or chronic, any combination thereof, in a selected population with absolutely dysfunctional CB2 receptor.

CB2 receptors are widely expressed in different tissues, primarily in the immune system, with the greatest density in the spleen. The expression level of CB2 in the immune cells is about 10 to 100 times higher than CB1. Within the immune system, CB2 is found in various cell types, including B cells, NK cells, monocytes, microglial cells, neutrophils, T cells, dendritic cells and mast cells. CB2 selective ligands have been developed and tested for their effects in various inflammatory settings. The results have indicated that CB2 receptor modulators can be employed for the treatment of medical conditions having an inflammatory component.

CB2 receptors are largely absent in the central nervous system (CNS) of adult mammals under normal conditions. The expression of CB2 receptors in the fully matured brain is about 1.5% of the level in the spleen, and these receptors are present on neuronal cells, mainly in the cerebellum and in the brain stem. However, CB2 receptors appear to be upregulated in microglial cells and astrocytes under selected neuroinflammatory stimulation or dysregulated under other selected disorders such as schizophrenia.

Modulation of CB2 receptor activity has been shown to be involved in the pathophysiology of different diseases, including osteoporosis, atherosclerosis, chronic pain and cancer.

4'-O-methylhonokiol

Honokiol, magnolol and 4'-O-methylhonokiol belong to a class of neolignan biphenols. These compounds are isolated from the barks, seed cones, and leaves of trees belonging to the genus *Magnolia*. In China, Korea, and Japan extracts from the bark or seed cones of the *Magnolia* tree have been widely used in traditional medicine as analgesic and to treat anxiety and mood disorders. During the last decades, honokiol has been shown to be a pleotropic compound exhibiting not only analgesic, anxiolytic, and antidepressant effects, but also antiemetic, anti-inflammatory, antibacterial, anti-tumorigenic, antithrombotic, neuroprotective, neurotrophic, and serotonergic effects.

The biphenyl neolignan 4'-O-methylhonokiol (MH) isolated from *Magnolia Grandiflora* L. seeds is a potent CB2 receptor ligand (Ki=50 nM), showing a unique inverse agonism and partial agonism via different pathways (cAMP and Ca2+, respectively) and potently inhibits osteoclastogenesis, but not GPR55 activity (Schuehly et al., Chem. & Biol. 18: 1053-1064, 2011). MH further attenuates memory impairment in presenilin 2 mutant mice through reduction of oxidative damage and inactivation of astrocytes and the ERK pathway. In a mouse model of Alzheimer's disease (AD), the orally administered MH has been shown to prevent amyloidogenesis and progression of AD by inhibiting neuroinflammation (Lee et al., J. Neuroinflamm. 9:35, 2012). It was postulated that MH may exert its beneficial effects in the AD mouse model via modulation of CB2 receptors expressed in microglial cells and astrocytes (Gertsch and Anavi-Goffer et al., J. Neuroinflamm. 9:135, 2012). However, MH also inhibits cyclooxygenase 2 (COX-2) enzymatic activity (Schuehly et al., Chem. & Biol. 18: 1053-1064, 2011). It has been shown that 4'-O-methylhonokiol (MH) and its analogues and derivatives are useful analgesic compounds to reduce pain, via selective mechanisms involving COX-2 and/or CB2 receptor. In addition, it has been shown that MH reduces anxiety, and it was postulated that MH may enhance GABAA receptor activity (Han H, et al., "Anxiolytic-like effects of 4-O-methylhonokiol isolated from *Magnolia officinalis* through enhancement of GABAergic transmission and chloride influx." J Med Food 14: 724-731, 2011).

Disorders Characterized by Repetitive Behavior:

Some disorders are characterized by repetitive vocals or movements, or involuntary movements or behaviors. These behaviors are in part classified according to the ICD-10 or DSM-IV classification and can be acute, transient or chronic in their appearance. Selected conditions which feature repetitive behaviors include developmental coordination disorder or stereotypic movement disorder, autism spectrum disorders, obsessive compulsive disorder (OCD), a bacterial-induced repetitive behavior disorder, pediatric autoimmune neuropsychiatric disorders associated with streptococcal infections (PANDAS), chorea (Sydenham's chorea (SC), chorea minor, chorea gravidarum, drug-induced chorea), drug-induced repetitive behaviors, akathisia, dyskinesias, dystonias, cramps and spasms, tremors, restless leg syndrome, moving toes/fingers syndrome, involuntary movement, stereotypic movement disorder, extrapyramidal movement disorders and Wernicke-Korsakoff syndrome. In some cases, the repetitive behavior can appear as tics that characterizes tic disorders, Tourette syndrome, vocal tics, motor tics. In some cases, the repetitive behavior can appear as altered, increased or repetitive vocalization or as part of another vocal disorder.

Some of these disorders are inherited neuropsychiatric disorder with onset in childhood, characterized by multiple physical (motor movements) and vocal (altered, increased or repetitive phonics) repetitive behavior. In other conditions, these disorders are acquired disorders due to bacterial infection, exposure to drugs and other environmental causes. The motor and vocal repetitive behaviors are often preceded by premonitory sensations or urges which are described by patients as a build-up of tension and compare the urges to the need to sneeze or scratch. Extreme repetitive behaviors in adulthood are a rarity, and does not necessarily affect intelligence or life expectancy.

The medication with the most proven efficacy in treating repetitive movements includes typical and atypical neuroleptics like pimozide (Orap®), which may have long-term and short-term adverse effects. The antihypertensive agents clonidine and guanfacine are also used to treat repetitive movements, showing variable efficacy, but a lower side effect profile than the neuroleptics. Stimulants and other medications may be useful in treating ADHD when it co-occurs with repetitive movement disorders. Drugs from several other classes of medications can be used when stimulant trials fail, including atomoxetine and tricyclic antidepressants. Selective serotonin reuptake inhibitors (SSRIs) may be prescribed when a patient also has OCD symptoms.

Obsessive Compulsive Disorder (OCD), a type of anxiety disorder, is a potentially disabling illness that traps sufferers in endless cycles of repetitive thoughts and behaviors. Subjects suffering from OCD are plagued by recurring, distressing and uncontrollable thoughts, fears, or images (obsessions). The resulting anxiety leads to an urgent need to perform certain rituals, routines or movements (compulsions). The compulsions are performed in an attempt to prevent or get rid of the obsessive thoughts. Although the compulsions may temporarily alleviate anxiety, the person must perform the compulsions again when the obsessive thoughts return. This OCD cycle can progress to the point of taking up hours of the person's day and significantly interfering with normal activities.

OCD has been linked to abnormalities with the neurotransmitter serotonin as patients benefit from the use of SSRIs, a class of antidepressant medications that allow for more serotonin to be readily available to other nerve cells.

Chorea belongs to the group of disorders called dyskinesias. Sydenham's chorea, a pediatric disorder, is thought to outburst at age 5-15 years as a result of streptococcus infections. The prevalence of Sydenham's chorea is higher in girls more than in boys. The disorder can be accompanied with the development of tics. PANDAS (Pediatric Autoimmune Neuropsychiatric Disorders Associated with Streptococcal Infections) is a pediatric disorder which typically appears in children age 3 to 12 years. The disorder is also thought to outburst as a result of streptococcus infections but other strains than these involved in Sydenham's chorea appear to be involved.

Akathisia is a disorder characterized by restlessness and a compelling need to be in constant motion. It is characterized by actions such as rocking while standing or sitting, lifting the feet as if marching, crossing/uncrossing the legs while sifting. Akathisia may result from anxiety or can be induced by drugs (e.g. antipsychotics, SSRIs, antidepressants).

The new results disclosed here support the therapeutic effects of CB2 receptor inverse agonists and/or CB2 receptor negative allosteric modulators which possibly, but not necessarily, act as mixed-type agonists or mixed-type CB2 receptor inverse agonists/selective estrogen receptor modulators (mixed CB2/SERM ligands) for the treatment of the selected disorders.

In some aspects, the composition of this invention is intended for use in the treatment of a human subject. In some other aspects, the composition is intended for use in the treatment of a non-human subject, an animal or a mammal.

The present invention is based on the findings that exposure to selective CB2 receptor inverse agonists reverses the effects of DOI ((−)-1-(2,5-dimethoxy-4-iodophenyl)-2-aminopropane hydrochloride or (−)-2,5-dimethoxy-4-iodo-amphetamine hydrochloride) on behavioral symptoms and repetitive movements in a murine model. It is disclosed that administration of DOI to mice at postnatal age of three weeks, adolescent age of 3 to 6 weeks and adult age up to 21 weeks increased head twitch response, ear scratch response and grooming behavior immediately after injection of DOI. These increased activities are characteristic of repetitive behaviors (head twitch response, ear scratch response and grooming behavior) and urge-like responses (ear scratch response and grooming behavior).

It is further disclosed that the therapeutic effect of selective CB2 receptor inverse agonists at age 3 weeks in the DOI mouse model is higher than at age 6 weeks (FIG. 2A-B). Age 3 weeks of mice corresponds to childhood (pediatric) to young teenage of a human subject. Age 6 weeks of mice is equivalent to late teenage to young adult of a human subject.

Figure 3:
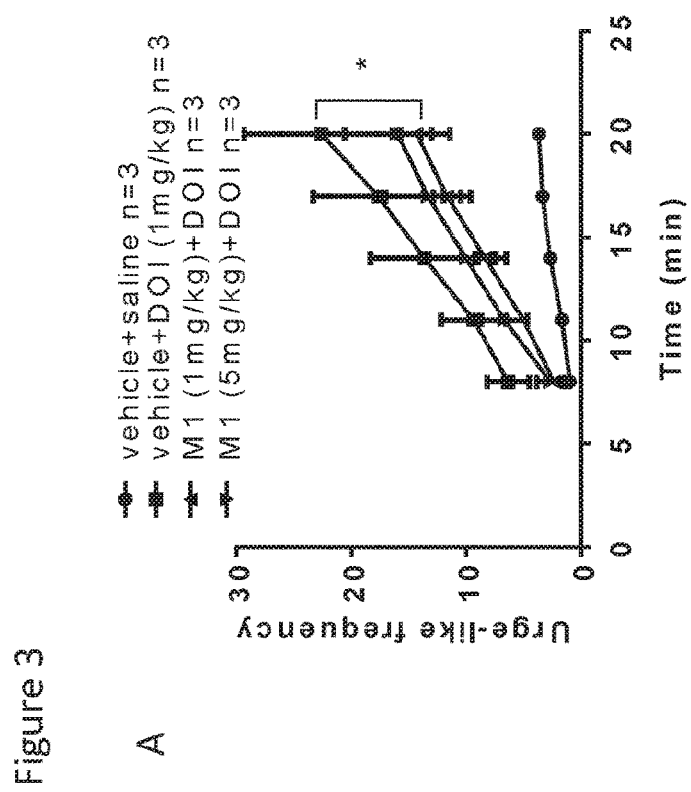
FIG. 3A-B are line graphs showing that MH reversed the effect of DOI on the frequency of grooming in mice that resemble urge-like response in human (FIG. 3A) and showing that MH alone had no effect on grooming frequency (FIG. 3B).

It is further disclosed that MH reversed the effect of DOI on the frequency of grooming in mice that resemble urge-like response in human (FIG. 3A) and that MH alone had no effect on grooming frequency (FIG. 3B).

It is further disclosed that administration of the selective CB1 receptor antagonist SR141716A to mice pups at the age of one to two days resulted in higher level of vocalization and/or higher number of vocals compared with their control litter mates which resemble behavior of repetitive vocalization.

The results disclosed herein support the therapeutic effects of 4'-O-methylhonokiol and its derivatives (formula I), raloxifene and its derivatives (formula II) and their fixed dose combinations through the CB2 receptor for the treatment of disorders characterized with repetitive behavior.

A fixed-dose combination (FDC), also known as combination drug, is a drug that includes two or more active pharmaceutical ingredients (APIs), combined in a single dosage form, which is formulated, manufactured and distributed in fixed doses.

4'-0-Methylhonokiol (2-(4-Methoxy-3-prop-2-enylphenyl)-4-prop-2-enylphenol; CAS number 68592-15-4, referred to herein as MH or M1, is a CB2 receptor mixed-type agonist/inverse agonist, naturally found in the flowers of *Magnolia grandiflora* and *Magnolia virginiana*.

In some aspects, methods and self-emulsifying compositions having selective CB2 receptor inverse agonists, and specifically 4'-O-methylhonokiol (also designated herein below M1 or MH) are disclosed, that are able to reduce the DOI-induced repetitive head twitches and DOI-induced grooming, characteristic of motor-like, OCD-like, urge-like and/or Tourette syndrome/tic-like behavior. This is surprising, because the results disclosed here indicate that the mechanism of action of MH is through the CB2 receptor (FIG. 4A) and through acting on CB2 receptors in the brain as the inhibition of DOI-induced repetitive head twitch is evident already after about one hour (FIG. 2B). This time line suggests that CB2 receptors in the periphery are not involved in this inhibition. This is surprising, because U.S. Pat. No. 9,486,419, incorporated herein by reference in its entirety, describes sub-chronic models, i.e. longer time line of days and weeks which can involve peripheral mechanisms as well as central mechanisms.

Another surprising result is that these findings are in contrast to those of Darmani et al, 2001 showing that non-selective mixed CB1/CB2 receptor agonists are able to reverse the DOI-induced head twitches and ear scratch responses (Darmani, 2001, "Cannabinoids of diverse structure inhibit two DOI-induced 5-HT(2A) receptor-mediated behaviors in mice." Pharmacol Biochem Behav 68: 311-317).

Figure 8:
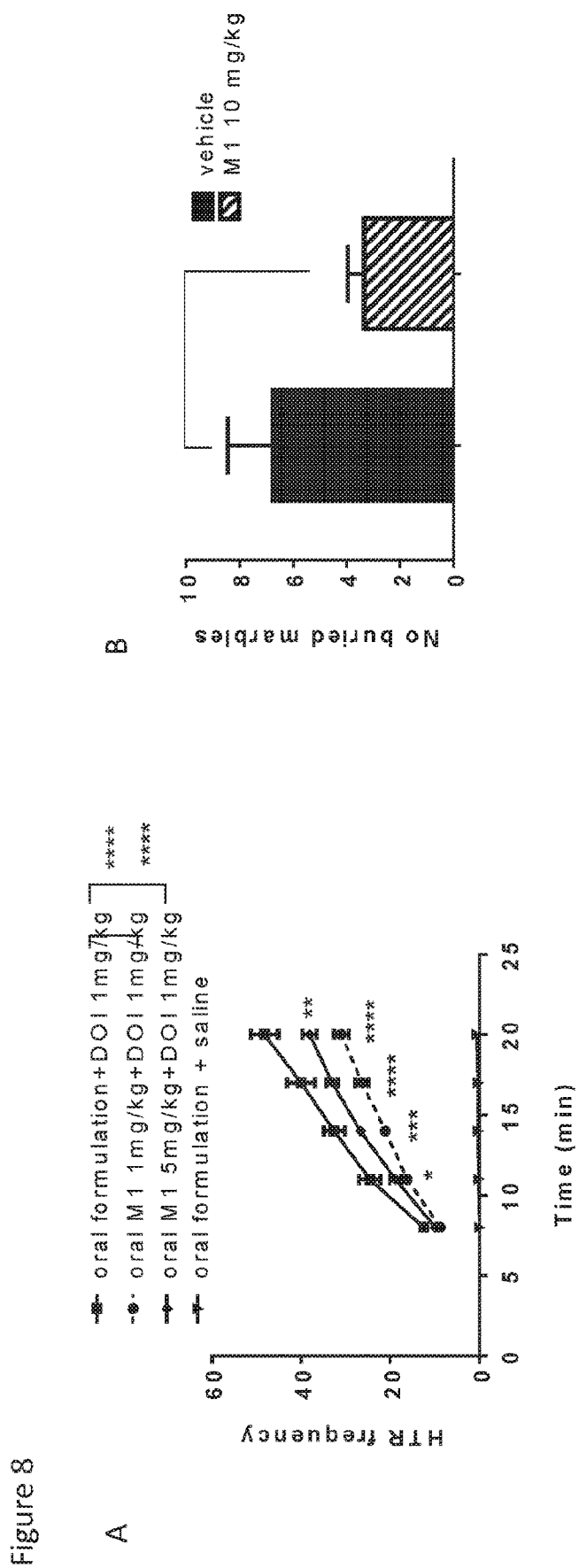
FIG. 8A shows that oral administration of MH in formulation reversed the effect of DOI on head twitch frequency (n=8 in each group). Compared with the effect of 5 intraperitoneal administration of MH at a dose of 1 mg/kg in mice (FIG. 2B), oral administration of MH at a dose of 1 mg/kg significantly reduce head twitch frequency in mice (FIG. 8A).
FIG. 8B shows that MH reduced compulsive behavior, MH reduced the number of buried marble (n=6 in each group).

It is disclosed in this invention that administration of MH in self-emulsifying oral composition (see for example Table 1) reverses the effect of DOI on head twitch frequency. Surprisingly, compared with the effect of intraperitoneal administration of MH at a dose of 1 mg/kg in mice (FIG. 2B), oral administration of MH in a self-emulsifying oral composition at a dose of 1 mg/kg significantly reduce head twitch frequency in mice (FIG. 8A). This dose is equivalent to about 0.08 mg/kg in a human. Thus, lower doses of 0.01-1 mg/kg in a human subject are expected to provide the therapeutic effects of MH in self-emulsifying oral compositions. Reducing the oral therapeutic dose is expected to result in reduced side-effects of MH in patients. It is also disclosed that MH reduces compulsive behavior, MH reduced the number of marble burring test (FIG. 8B), further supporting that therapeutic effect MH in ameliorating repetitive behaviors in a variety of clinical indications.

It is further disclosed in this invention that administration of the CB2 receptor inverse agonist, when the CB2 receptor inverse agonist is N-(benzo[1,3]dioxol-5-ylmethyl)-7-methoxy-2-oxo-8-pentyloxy-1,2-dihydroquinoline-3-carboxamide (JTE 907), at a dose of 0.2 mg/kg reversed the effect of DOI on head twitch frequency (FIG. 7A) and reduced compulsive behavior in mice (FIG. 7B). These results suggest that the therapeutic dose of highly potent selective CB2 receptor inverse agonist in a human subject can, for example, be reduced to about 0.016 mg/kg in a human. Thus, lower doses of 0.0001-0.02 mg/kg in a human subject are expected to provide the same therapeutic effects as those of potent CB2 receptor selective agents in self-emulsifying oral compositions. In some embodiments, effective therapeutic doses can comprise 0.0001 to 0.001 mg/kg, 0.0001 to 0.0005 mg/kg, 0.0005 to 0.001 mg/kg, 0.001 to 0.005 mg/kg, 0.005 to 0.01 mg/kg, 0.01 to 0.015 mg/kg, 0.01 to 0.02 mg/kg, 0.015 to 0.02 mg/kg of JTE 907.

Surprisingly, raloxifene, a mixed selective CB2 receptor inverse agonist/SERM ligand, was able to reduce DOI-induced repetitive head twitches (FIG. 1) which makes it an interesting new candidate for the treatment of disorders that are characterized with repetitive behaviors. This is unexpected, as the current use of raloxifene is as anti-cancer drug for the treatment of breast cancer. The diseases or disorders are selected of Tourette syndrome, developmental coordination disorder, stereotypic movement disorder, autism spectrum disorders, bacterial-induced repetitive behavior, NMDA antibody-related encephalitis, autoimmune antibody-mediated mental disorder, autoimmune antibody-mediated psychosis, pediatric autoimmune neuropsychiatric disorders-associated with streptococcal infections (PANDAS), chorea (Sydenham's chorea (SC), chorea minor, chorea gravidarum, drug-induced chorea), drug-induced repetitive behaviors, akathisia, dyskinesias, dystonias, cramps and spasms, tremors, restless leg syndrome, moving toes/fingers syndrome, involuntary movement, stereotypic movement disorder, extrapyramidal movement disorders, Wernicke-Korsakoff syndrome and a combination thereof wherein acute, transient or chronic.

Raloxifene was singled out based on the positive identification of this drug as a CB2 receptor inverse agonist (Kumar & Song, "Identification of raloxifene as a novel CB2 inverse agonist." Biochem Biophys Res Commun 435: 76-81 2013) together with the fact that it produces fewer side effects than other actives of this drug family.

Bazedoxifene and lasofoxifene are also mixed selective CB2 inverse agonist/SERM ligands (Kumar & Song, "CB2 cannabinoid receptor is a novel target for third-generation selective estrogen receptor modulators bazedoxifene and lasofoxifene." Biochem Biophys Res Commun 443: 144-149, 2014).

Figure 6:
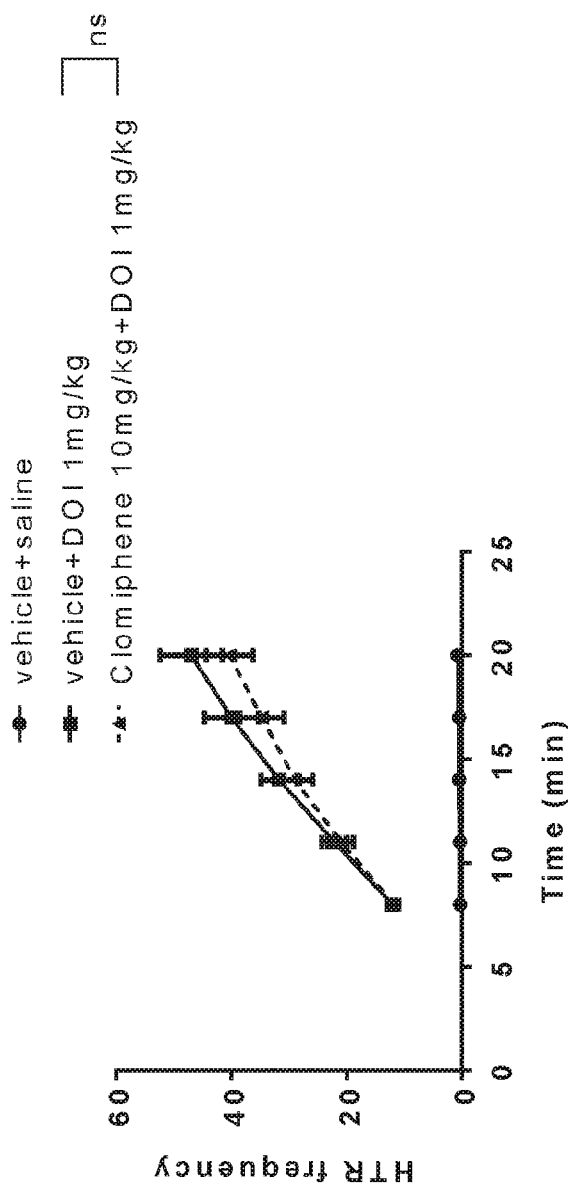
FIG. 6 Compared with 10 mg/kg raloxifene, a SERM/CB2 receptor drug (in FIG. 1), another SERM drug, clomiphene citrate at 10 mg/kg did not reverse the effect of DOI on head twitch frequency (FIG. 6, n=5 in each group).

Another drug of SERM family is clomiphene citrate, has been used to treat a patient with Tourette syndrome (Sandyk, Bamford & Laguna, 1987, "Clomiphene citrate in Tourette's syndrome." Postgrad Med J 63: 5100-511). However, the mechanism for the clomiphene action is different from that of raloxifene. While clomiphene citrate modulates the release of luteinizing hormone and reduces the level of estrogen in the hypothalamus (Sandyk, Bamford & Laguna, 1987), raloxifene acts differently, as an estrogen modulator to reduce breast and uterus cancers and on CB2 receptors (Kumar & Song, "Identification of raloxifene as a novel CB2 inverse agonist." Biochemical and Biophysical Research Communications 435: 76-81, 2013.) In support of this view, clomiphene citrate, a SERM ligand which has not been identified as a CB2 receptor ligand, and did not significantly affect DOI-induced repetitive head twitches at 10 mg/kg (FIG. 6), a dose which significantly reversed DOI-induced repetitive head twitches by raloxifene a SERM/CB2 receptor drug (FIG. 1). Importantly, clomiphene citrate is not used for treatment of Tourette syndrome in practice (McNaught & Mink, "Advances in understanding and treatment of Tourette syndrome." Nature Reviews Neurology 7: 667-676, 2011) although the anecdotal report one patient with Tourette syndrome (Sandyk, Bamford & Laguna, 1987).

In addition, raloxifene is way more effective than clomiphene citrate, as it reduces motor tics after a single dose of 10 mg/kg in a mouse (equivalent to 0.8 mg/kg a single dose a patient), while clomiphene citrate needs a 25 mg dose twice per day given to a patient for a week (about 50 mg/70 kg is about 0.7 mg/kg times 7 is about 5-7 mg/kg; (Sandyk, Bamford & Laguna, 1987)), which is a 7.5 times higher dose than raloxifene.

Figure 9:
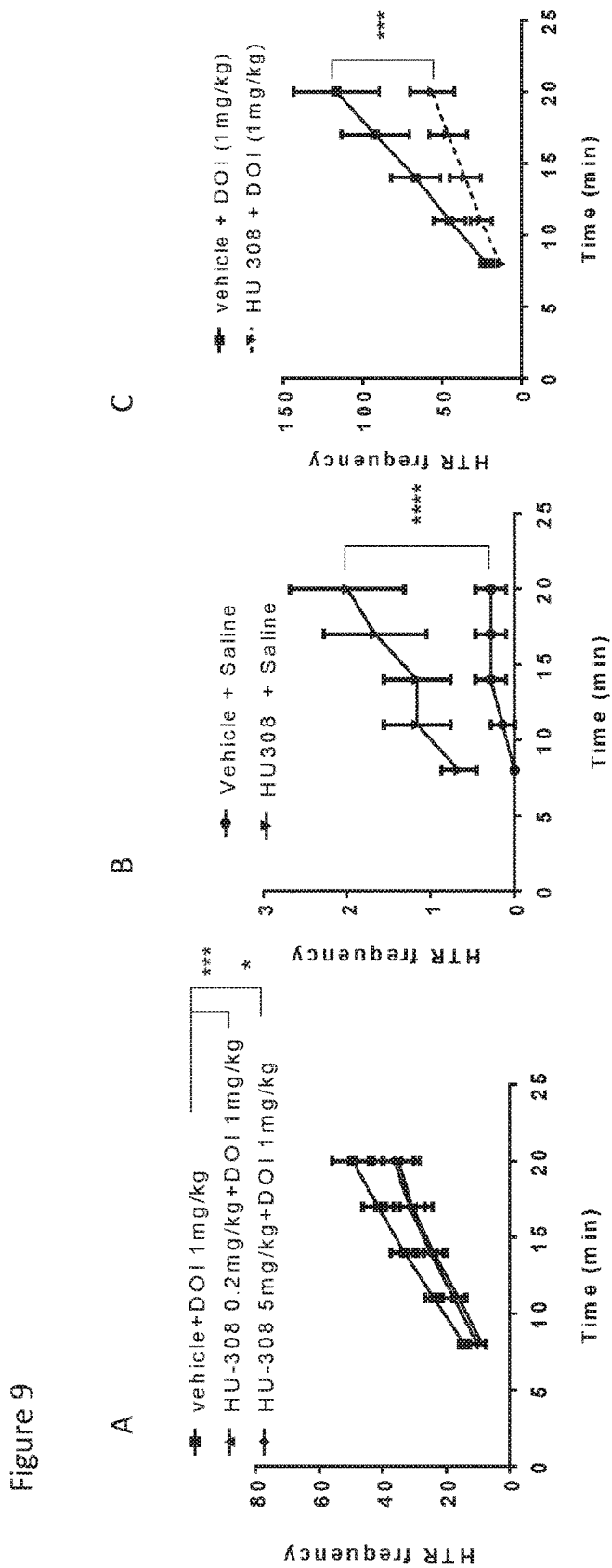
FIG. 9A is a line graph showing that HU-308 reversed the effect of DOI on head twitch frequency of wild mice (n=8 in each group).
FIG. 9B is a line graph showing that HU-308 alone increases head twitch frequency of wild healthy mice (n=6-7 in each group).
FIG. 9C is a line graph showing that HU-308 significantly reversed the effect of DOI on head twitch frequency of CB2 receptor knockout mice (n=3-4 in each group).

Another surprising results are that [(1R,2R,5R)-2-[2,6-dimethoxy-4-(2-methyloctan-2-yl)phenyl]-7,7-dimethyl-4-bicyclo[3.1.1]hept-3-enyl] methanol (HU-308), and beta-caryophyllene (BCP), CB2 receptor selective agonists, that act as antipsychotic drugs (see co-pending U.S. patent application Ser. No. 14/385,739, published as US2015/051299) were able to reduce DOI-induced repetitive head twitches (see FIG. 9A for HU-308). These results are surprising, as it was expected that these ligands will act in opposite way to MH (M1). Thus, it was expected that HU-308 and BCP will either have no effect on DOI-induced head twitches or exacerbate them. This is because, postnatal administration of HU-308 (5 mg/kg) during postnatal days 5-13 was shown to induce abnormal motor tics/head twitches at the age of 12 weeks as measured in the open field test (see U.S. Pat. No. 9,486,419, incorporated herein by reference in its entirety). Indeed, when HU-308 is given alone it significantly increases head twitches (FIG. 9B). Thus, together, these results further show that CB2 receptor selective agonists are indeed not ideal candidates for the treatment of Tourette syndrome. However, another surprising result was that HU-308 was able to significantly reduce DOI-induced repetitive head twitches in the CB2 receptor knockout mice (FIG. 9C). This is in contrast to MH (M1) which had no effect on head twitch in the CB2 receptor knockout mice FIG. 4A).

Noteworthy, HU-308 or BCP-induced tic-like inhibition is evident already after about one hour. This time line suggests that CB2 receptors in the periphery are not involved in the tic-like inhibition. This is also in contrast to the recitals of Darmani et al, 2001 showing that non-selective mixed CB1/CB2 receptor agonists are able to reverse the DOI-induced head twitches and ear scratch responses (see Darmani, 2001 in References below).

Collectively, these results suggest that patients with tic disorders and other repetitive behavior disorders who have functional CB2 receptors should not be treated with a CB2 receptor selective agonist such as HU-308 or BCP.

According to some embodiments, HU-308 and BCP, CB2 receptor selective agonists, can be used for the treatment of tic disorders and other repetitive behavior disorders in a selected population with absolutely dysfunctional CB2 receptors.

According to some aspects of the invention, the BCP used for implementing the teachings herein is at least about 65%, at least about 75%, at least about 85% and even at least about 95% by weight E-BCP. In some embodiments, the BCP is substantially pure (at least about 98% or at least about 99% by weight) E-BCP.

In other aspects, the BCP used for implementing the teachings herein is at least about 65%, at least about 75%, at least about 85% and even at least about 95% by weight Z-BCP. In some embodiments, the BCP is substantially pure (at least about 98% or at least about 99% by weight) Z-BCP.

In some aspects, the BCP used for implementing the teachings herein is at least about 65%, at least about 75%, at least about 85% and even at least about 95% or about 98% by weight E-BCP and/or Z-BCP. In some embodiments, the BCP is substantially pure (at least about 97-99% by weight) E-BCP and/or Z-BCP.

For example, in some aspects, the BCP used for implementing the teachings herein comprises at least about 49% E-BCP, about 1-49% Z-BCP, about 1-5% BCP oxide and about 1-15% alpha humulene.

For example, in some aspects, the BCP used for implementing the teachings herein comprises about 45-49% E-BCP, about 45-49% Z-BCP, about 1-5% BCP oxide and about 1-5% alpha humulene.

For example, in some aspects BCP used for implementing the teachings herein comprises about 45-90% E-BCP, about 5-30% Z-BCP, about 1-5% BCP oxide and traces alpha humulene.

According to additional embodiments, the pharmaceutical compositions of this invention are administered by a route selected from the group consisting of oral, intravenous, intra-arterial, intramuscular, intraperitoneal, subcutaneous, inhalation, transdermal, vaginal, and rectal administration route. Each possibility is a separate embodiment of the invention.

According to other embodiments, the average daily therapeutically effective amount of the active agent in the pharmaceutical composition of this invention administered to a human subject is in a range selected from the group consisting of 0.001-1000 mg/kg, from about 0.001-0.01 mg/kg, about 0.01-1 mg/kg, about 1-10, about 10-100 mg/kg or about 100-1000 mg/kg according to patient's age, the active agent and the mode of administration.

According to other embodiments, the average daily therapeutically effective amount of the active agent in the pharmaceutical composition of this invention administered to a non-human subject is in a range selected from the group consisting of 0.002-6000 mg/kg, from about 0.002-0.01 mg/kg, about 0.01-1 mg/kg, about 1-100 mg/kg, about 100-1000 mg/kg or about 1000-6000 mg/kg according to subject's age, subject's species, composition's effectiveness, the active agent and the mode of administration. Each possibility is a separate embodiment of the invention.

According to other embodiments, the average daily therapeutically effective amount of the active agent in the self-emulsifying pharmaceutical composition of this invention administered to a human subject is in a range selected from the group consisting of 0.0001-500 mg/kg, about 0.0001-0.001 mg/kg, about 0.001-0.01 mg/kg, about 0.01-1 mg/kg, about 1-100 mg/kg or about 100-500 mg/kg according to patient's age, composition's effectiveness, the active agent and the mode of administration. Each possibility is a separate embodiment of the invention.

According to other embodiments, the average daily therapeutically effective amount of the active agent in the self-emulsifying pharmaceutical composition of this invention administered to a non-human subject is in a range selected from the group consisting of 0.0002-3000 mg/kg, from about 0.002-0.01 mg/kg, about 0.01-1 mg/kg, about 1-10 mg/kg, about 10-100 mg/kg, about 100-1000 mg/kg or about 1000-3000 mg/kg according to subject's age, subject's species, composition's effectiveness, the active agent and the mode of administration. Each possibility is a separate embodiment of the invention.

In some embodiments, there is provided a method of treatment of ADHD (Attention-deficit hyperactivity disorder), Tourette syndrome (TS), a tic disorder, a vocal disorder, obsessive compulsive disorder (OCD), developmental coordination disorder, stereotypic movement disorder, autism spectrum disorders, bacterial-induced repetitive behavior, pediatric autoimmune neuropsychiatric disorders associated with streptococcal infections (PANDAS), chorea (Sydenham's chorea (SC), chorea minor, chorea gravidarum, drug-induced chorea), drug-induced repetitive behaviors, akathisia, dyskinesias, dystonias, cramps and spasms, tremors, restless leg syndrome, moving toes/fingers syndrome, involuntary movement, stereotypic movement disorder, extrapyramidal movement disorders, Wernicke-Korsakoff syndrome, Parkinson's disease, amyotrophic lateral sclerosis, Alzheimer's disease, Huntington's disease, multiple sclerosis and combinations thereof, wherein acute, transient or chronic, epilepsy, seizures, diabetes, insulin resistance, hypertension, pain, anesthesia, inflammation, convulsions, infertility, aging, schizophrenia, schizoaffective disorder, bipolar disorder I and II, unipolar disorder, multiple personality disorder, psychotic disorders, depression, psychotic depression, depressive disorders, major depressive disorder, epilepsy, anxiety disorders, autistic spectrum disorder, enuresis, addiction, withdrawal symptoms associated with addiction, Asperger syndrome, oppositional defiant disorder, behavioral disturbance, agitation, psychosis/agitation associated with Alzheimer's disease, psychosis associated with Parkinson's disease, psychosis associated with drug of abuse, psychosis associated with psychedelic drug abuse, LSD-induced psychosis, steroid-induced schizophrenia, steroid-induced psychosis, Capgras syndrome; Fregoli syndrome; Cotard, personality disorders, borderline personality disorder, avoidant personality disorder, mania, dementia, anorexia, anorexia nervosa, eating disorders, narcolepsy, anxiety, generalized anxiety disorder, social anxiety disorder, body dismographic disorder, paranoid disorder, nightmares, agitation, post-traumatic stress disorder (PTSD), severe mood dysregulation, developmental coordination disorder, neuroinflammatory diseases, neurodegenerative diseases, liver associated-diseases, hepatitis, alcohol-related liver disease, fibromyalgia, gastrointestinal diseases, inflammatory bowel disease, Crohn's disease, ulcerative colitis, cancer, depression or anxiety that leads to metabolic diseases, metabolic diseases, infertility, cardiovascular diseases, osteoporosis, traumatic brain injury, cerebral ischemia, depression associated with any of the above clinical conditions, anxiety associated with any of the above clinical conditions, hyperactivity associated with any of the above clinical conditions, inattention associated with any of the above clinical conditions, involuntary movements associated with any of the above clinical conditions, cognitive deficits associated with any of the above clinical conditions, and combinations thereof, wherein the disorder is acute, transient or chronic disease, in a patient in need thereof with a composition, in any mode of administration, including but not limited to administration in a slow-release/long-active formulations formulated in a dosage form selected from the group consisting of a solution, suspension, emulsion, powder, tablet, caplet, capsule, dragee, depot, granules, syrup, transdermal patch, spray, gastroresistant oral dosage, gastroresistant softgel capsule, cream, nasal dosage, sublingual dosage and suppository or formulated as an injectable solution and administered as intravenous injection, intra-arterial injection, intramuscular injection, intradermal injection, intraperitoneal injection, intrathecal injection, depot injection or subcutaneous injection, given on a daily basis, of the present disclosure wherein the average daily amount of said 4-0-methylhonokiol (MH) or raloxifene or HU-308 or BCP administered is in a range selected from the group consisting of 0.0001-0.1 mg, 0.1-1 mg, 1-10 mg, 10-20 mg, 20-50 mg, 50-100 mg, 100-200 mg or 200-1000 mg, 1000-10000 mg according to the patient's age, subject's age, subject's species, composition's effectiveness, the active agent and the mode of administration. Each possibility is a separate embodiment of the invention.

According to other embodiments, the average daily therapeutically effective amount of the active agent in the pharmaceutical composition of this invention administered to a human subject is in a range selected from the group consisting of 0.001-1000 mg/kg, from about 0.001-0.01 mg/kg, about 0.01-1 mg/kg, about 1-10, about 10-100 mg/kg or about 100-1000 mg/kg according to patient's age, the active agent and the mode of administration.

According to other embodiments, the average daily therapeutically effective amount of the active agent in the pharmaceutical composition of this invention administered to a non-human subject is in a range selected from the group consisting of 0.002-6000 mg/kg, from about 0.002-0.01 mg/kg, about 0.01-1 mg/kg, about 1-100 mg/kg, about 100-1000 mg/kg or about 1000-6000 mg/kg according to subject's age, subject's species, composition's effectiveness, the active agent and the mode of administration. Each possibility is a separate embodiment of the invention.

According to other embodiments, the average daily therapeutically effective amount of the active agent in the self-emulsifying pharmaceutical composition of this invention administered to a human subject is in a range selected from the group consisting of 0.0001-500 mg/kg, about 0.0001-0.001 mg/kg, about 0.001-0.01 mg/kg, about 0.01-1 mg/kg, about 1-100 mg/kg or about 100-500 mg/kg according to patient's age, composition's effectiveness, active agent and the mode of administration. Each possibility is a separate embodiment of the invention.

According to other embodiments, the average daily therapeutically effective amount of the active agent in the self-emulsifying pharmaceutical composition of this invention administered to a non-human subject is in a range selected from the group consisting of 0.0002-3000 mg/kg, from about 0.002-0.01 mg/kg, about 0.01-1 mg/kg, about 1-10 mg/kg, about 10-100 mg/kg, about 100-1000 mg/kg or about 1000-3000 mg/kg according to subject's age, subject's species, composition's effectiveness, active agent and the mode of administration. Each possibility is a separate embodiment of the invention.

In some embodiments, there is provided a method of treatment of a human or non-human subject in need thereof, wherein the subject has a mental, movement or behavioral disorder with a composition formulated as a capsule or an injection, for example but not limited to intramuscular injection. In some embodiments, the composition comprises an active agent in a range selected from the group consisting of 0.0001-0.01 mg, 0.01-0.1 mg, 0.1-10 mg, 10-100 mg, 100-200 mg, 200-300 mg, 300-400 mg, 500-600 mg, 600-700 mg, 700-800 mg or 800-1000 mg, 1000-1500 mg, 1000-2000 mg, 2000-5000 mg, 5000-10000 mg according to the patient's age, subject's age, subject's species, active agent and the mode of administration.

In some embodiments, there is provided a method of treatment of a human or non-human subject in need thereof having a mental, movement or behavioral disorder with a delayed-release composition (such as compositions for a slow-release, slow-acting form of medication prepared as a capsule or a depot injection given for example but not limited by intramuscular injection). In some embodiments, the delayed-release composition can be administrated every 1 week, every 2 weeks, every 3 weeks or once a month to up to every six months, wherein the average amount of a single administration of an active agent administered is in a range selected from the group consisting of 0.0001-0.01 mg, 0.01-0.1 mg, 0.1-10 mg, 10-100 mg, 100-200 mg, 200-300 mg, 300-400 mg, 500-600 mg, 600-700 mg, 700-800 mg or 800-1000 mg, 1000-1500 mg, 1000-2000 mg, 2000-5000 mg, 5000-10000 mg according to the patient's age, subject's age, subject's species, composition's effectiveness, the active agent and the mode of administration.

In some embodiments, there is provided a method of treatment of a mental, movement or behavioral disorder in a patient in need thereof with a delayed-release composition (such as compositions for a slow-release, slow-acting form of medication prepared as a capsule or a depot injection, given for example but not limited by intramuscular injection, which are administered every 1 week or once a month to up to every six months) of the present disclosure wherein the average amount of a single administration of said 4-0-methylhonokiol (MET) or raloxifene or HU-308 or BCP administered is in a range selected from the group consisting of 0.0001-0.01 mg, 0.01-0.1 mg, 0.1-10 mg, 10-100 mg, 100-200 mg, 200-300 mg, 300-400 mg, 500-600 mg, 600-700 mg, 700-800 mg or 800-1000 mg, 1000-1500 mg, 1000-2000 mg, 2000-5000 mg, 5000-10000 mg according to the patient's age, subject's age, subject's species, composition's effectiveness, active agent and the mode of administration. Each possibility is a separate embodiment of the invention. According to an embodiment, there is provided a method of treatment of a mental, movement or behavioral disorder in a patient in need thereof with a composition of the present disclosure.

According to additional embodiments, the pharmaceutical composition is administered once every 6 months, once every 3 months to about once a month, once a week to about 3 times per day, once per week, twice per week, 3 times per week, 4 times per week, 5 times per week, 6 times per week, once per day, twice per day, 3 times per day or 4 times per day to a patient in need thereof. Each possibility is a separate embodiment of the invention.

According to a further embodiment, the pharmaceutical composition comprising the mixed selective CB2 inverse agonist/SERM ligand is formulated in a form selected from the group consisting of a solution, suspension, emulsion, powder, tablet, caplet, capsule, a dragee, depot, granules, a syrup, transdermal patch, spray, gastroresistant oral dosage, gastroresistant softgel capsule, cream, nasal, sublingual and suppository. Each possibility is a separate embodiment of the invention.

According to additional embodiments, the pharmaceutical composition comprising the mixed selective CB2 inverse agonist/SERM ligand is administered by a route selected from the group consisting of oral, intravenous injection, intra-arterial injection, intramuscular injection, intradermal injection, intraperitoneal injection, intrathecal injection, depot injection, subcutaneous injection, inhalation, transdermal, vaginal, and rectal administration route. Each possibility is a separate embodiment of the invention.

According to additional embodiments, the average daily therapeutically effective amount of the active agent in the pharmaceutical composition administered to a human or non-human subject is in a range selected from the group consisting of about 0.0001-6000 mg/kg, from about 0.002-0.01 mg/kg, about 0.01-1 mg/kg, about 1-100 mg/kg, about 100-1000 mg/kg or about 1000-6000 mg/kg according to patient's age, subject's age, subject's species, composition's effectiveness, the active agent and the mode of administration. Each possibility is a separate embodiment of the invention.

In some embodiments, there is provided a method of treatment of ADHD (Attention-deficit hyperactivity disorder), Tourette syndrome (TS), a tic disorder, a vocal disorder, obsessive compulsive disorder (OCD), developmental coordination disorder, stereotypic movement disorder, autism spectrum disorders, bacterial-induced repetitive behavior, pediatric autoimmune neuropsychiatric disorders associated with streptococcal infections (PANDAS), chorea (Sydenham's chorea (SC), chorea minor, chorea gravidarum, drug-induced chorea), drug-induced repetitive behaviors, akathisia, dyskinesias, dystonias, cramps and spasms, tremors, restless leg syndrome, moving toes/fingers syndrome, involuntary movement, stereotypic movement disorder, extrapyramidal movement disorders, Wernicke-Korsakoff syndrome, Parkinson's disease, amyotrophic lateral sclerosis, Alzheimer's disease, Huntington's disease, multiple sclerosis and combinations thereof, wherein acute, transient or chronic, epilepsy, seizures, diabetes, insulin resistance, hypertension, pain, anesthesia, inflammation, convulsions, infertility, aging, schizophrenia, schizoaffective disorder, bipolar disorder I and II, unipolar disorder, multiple personality disorder, psychotic disorders, depression, psychotic depression, depressive disorders, major depressive disorder, epilepsy, anxiety disorders, autistic spectrum disorder, enuresis, addiction, withdrawal symptoms associated with addiction, Asperger syndrome, oppositional defiant disorder, behavioral disturbance, agitation, psychosis/agitation associated with Alzheimer's disease, psychosis associated with Parkinson's disease, psychosis associated with drug of abuse, psychosis associated with psychedelic drug abuse, LSD-induced psychosis, steroid-induced schizophrenia, steroid-induced psychosis, Capgras syndrome, Fregoli syndrome, Cotard, personality disorders, borderline personality disorder, avoidant personality disorder, mania, dementia, anorexia, anorexia nervosa, eating disorders, narcolepsy, anxiety, generalized anxiety disorder, social anxiety disorder, body dismographic disorder, paranoid disorder, nightmares, agitation, post-traumatic stress disorder (PTSD), severe mood dysregulation, developmental coordination disorder, neuroinflammatory diseases, neurodegenerative diseases, liver associated-diseases, hepatitis, alcohol-related liver disease, fibromyalgia, gastrointestinal diseases, inflammatory bowel disease, Crohn's disease, ulcerative colitis, cancer, depression or anxiety that leads to metabolic diseases, metabolic diseases, infertility, cardiovascular diseases, osteoporosis, traumatic brain injury, cerebral ischemia, depression associated with any of the above clinical conditions, anxiety associated with any of the above clinical conditions, hyperactivity associated with any of the above clinical conditions, inattention associated with any of the above clinical conditions, involuntary movements associated with any of the above clinical conditions, cognitive deficits associated with any of the above clinical conditions, and combinations thereof, wherein the disorder is acute, transient or chronic disease, in a patient in need thereof with a self-emulsifying composition, in any mode of administration, including but not limited to administration in a slow-release/long-active formulations given on a daily basis, of the present disclosure wherein the average daily amount of said 4-0-methylhonokiol (MH) or raloxifene or HU-308 or BCP administered is in a range selected from the group consisting of 0.0001-0.001 mg, 0.001-0.01 mg, 0.01-0.1 mg, 0.1-1 mg, 1-10 mg, 10-20 mg, 20-50 mg, 50-100 mg, 100-200 mg, 200-1000 mg, 1000-10000 mg according to the patient's age, subject's age, subject's species, composition's effectiveness, active agent and the mode of administration. Each possibility is a separate embodiment of the invention.

In some further embodiments, there is provided a method of treatment of ADHD (Attention-deficit hyperactivity disorder), Tourette syndrome (TS), tic disorder, vocal disorder, developmental coordination disorder, stereotypic movement disorder, autism spectrum disorders, obsessive-compulsive disorder (OCD), bacterial-induced repetitive behavior, pediatric autoimmune neuropsychiatric disorders associated with streptococcal infections (PANDAS), chorea (Sydenham's chorea (SC), chorea minor, chorea gravidarum, drug-induced chorea), drug-induced repetitive behaviors, akathisia, dyskinesias, dystonias, cramps and spasms, tremors, restless leg syndrome, moving toes/fingers syndrome, involuntary movement, stereotypic movement disorder, extrapyramidal movement disorders, Wernicke-Korsakoff syndrome and combinations thereof, wherein acute, transient or chronic, in a patient in need thereof with a composition in a patient in need thereof with delayed-release composition (such as compositions for a slow-release, slow-acting form of medication prepared as a capsule or a depot injection given for example but not limited by intramuscular injection, which are administrated every 1 week, every 2 weeks, every 3 weeks or once a month to up to every six months) of the present disclosure wherein the average amount of a single administration of 4-0-methylhonokiol (MH) or raloxifene or HU-308 or BCP administered is in a range selected from the group consisting of 0.0001-0.1 mg, 0.1-10 mg, 10-100 mg, 100-200 mg, 200-300 mg, 300-400 mg, 500-600 mg, 600-700 mg, 700-800 mg or 800-1000 mg, 1000-1500 mg, 1000-2000 mg, 2000-5000 mg, 5000-10000 mg, according to the patient's age, active agent and the mode of administration. Each possibility is a separate embodiment of the invention.

According to additional embodiments, the pharmaceutical composition is administered once every 6 months, once every 3 months to about once a month, once a week to about 3 times per day, for example once per week, twice per week, 3 times per week, 4 times per week, 5 times per week, 6 times per week, once per day, twice per day or 3 times per day or 4 times per day to a patient in need thereof. Each possibility is a separate embodiment of the invention.

According to a further embodiment, the present invention provides a pharmaceutical composition comprising a CB2 receptor inverse agonist of the general formula I:

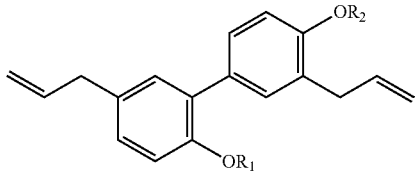

or a salt thereof and a pharmaceutically acceptable carrier, wherein $R_1$ and $R_2$ are each independently selected from the group consisting of hydrogen, $C_1$-$C_8$ alkyl, $C_3$-$C_8$ cycloalkyl, $C_1$-$C_8$ haloalkyl, or $C_3$-$C_8$ cyclohaloalkyl, and wherein $R_1$ and $R_2$ are not both hydrogen, for treatment of a disorder selected from the group consisting of developmental coordination disorder, stereotypic movement disorder, autism spectrum disorders, obsessive-compulsive disorder (OCD), bacterial-induced tic disorder, pediatric autoimmune neuropsychiatric disorders-associated with streptococcal infections (PANDAS), chorea (Sydenham's chorea (SC), chorea minor, chorea gravidarum, drug-induced chorea), drug-induced repetitive behaviors, akathisia, dyskinesias, Wernicke-Korsakoff syndrome, a tic disorder including but not limited to Tourette syndrome, and a combination thereof. Each possibility is a separate embodiment of the invention.

According to a certain embodiment, $R_1$ is hydrogen and $R_2$ is methyl, and the CB2 receptor inverse agonist is thus 4'-O-Methylhonokiol.

According to another aspect, the present invention provides a pharmaceutical composition comprising a mixed CB2 receptor inverse agonist/selective estrogen receptor modulator (SERM) of the general formula II:

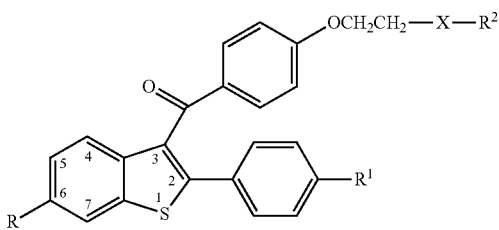

wherein
X is a bond, $CH_2$, or $CH_2CH_2$;
R and R', independently, are hydrogen, hydroxyl, $C_1$-$C_6$ alkoxy, $C_1$-$C_6$-acyloxy, $C_1$-$C_6$-alkoxy-$C_2$-$C_6$-acyloxy, $R_3$-substituted aryloxy, $R_3$-substituted aroyloxy, $R^4$-substituted carbonyloxy, chloro, or bromo;
$R^2$ is a heterocyclic ring selected from the group consisting of pyrrolidino, piperidino, or hexamethyleneimino;
$R^3$ is $C_1$-$C_3$-alkyl, C1-C3-alkoxy, hydrogen, or halo; and
$R^4$ is $C_1$-$C_6$-alkoxy or aryloxy; or a pharmaceutically acceptable salt thereof, wherein the mixed CB2/SERM ligand is selected from the group consisting of raloxifene, bazedoxifene, lasofoxifene, tamoxifen, afimoxifene, arzoxifene, ormeloxifene, toremifene, ospemifene, and a combination thereof, for use in the treatment of behavior disorders selected from the group consisting of developmental coordination disorder, stereotypic movement disorder, autism spectrum disorders, obsessive-compulsive disorder (OCD), bacterial-induced tic disorder, pediatric autoimmune neuropsychiatric disorders-associated with streptococcal infections (PANDAS), chorea (Sydenham's chorea (SC), chorea minor, chorea gravidarum, drug-induced chorea), drug-induced repetitive behaviors, akathisia, dyskinesias, Wernicke-Korsakoff syndrome, a tic disorder including but not limited to Tourette syndrome and a combination thereof.

According to a further embodiment, the present invention provides a pharmaceutical composition comprising a CB2 receptor inverse agonist of the CB2 receptor inverse agonist N-(benzo[1,3]dioxol-5-ylmethyl)-7-methoxy-2-oxo-8-pentyloxy-1,2-dihydroquinoline-3-carboxamide (JTE 907) or a salt thereof and a pharmaceutically acceptable carrier, for treatment of a disorder selected from the group consisting of developmental coordination disorder, stereotypic movement disorder, autism spectrum disorders, obsessive-compulsive disorder (OCD), bacterial-induced tic disorder, pediatric autoimmune neuropsychiatric disorders-associated with streptococcal infections (PANDAS), chorea (Sydenham's chorea (SC), chorea minor, chorea gravidarum, drug-induced chorea), drug-induced repetitive behaviors, akathisia, dyskinesias, Wernicke-Korsakoff syndrome, a tic disorder including but not limited to Tourette syndrome, and a combination thereof. Each possibility is a separate embodiment of the invention.

According to a further embodiment, the present invention provides a pharmaceutical composition comprising a CB2 receptor inverse agonist of the CB2 receptor inverse agonist the CB2 receptor inverse agonist 5-(4-Chloro-3-methylphenyl)-1-[(4-methylphenyl)methyl]-N-[(1S,2S,4R)-1,3,3-trimethylbicyclo[2.2.1]heptan-2-yl]-1H-pyrazole-3-carboxamide (SR 144528) or a salt thereof and a pharmaceutically acceptable carrier, for treatment of a disorder selected from the group consisting of developmental coordination disorder, stereotypic movement disorder, autism spectrum disorders, obsessive-compulsive disorder (OCD), bacterial-induced tic disorder, pediatric autoimmune neuropsychiatric disorders-associated with streptococcal infections (PANDAS), chorea (Sydenham's chorea (SC), chorea minor, chorea gravidarum, drug-induced chorea), drug-induced repetitive behaviors, akathisia, dyskinesias, Wernicke-Korsakoff syndrome, a tic disorder including but not limited to Tourette syndrome, and a combination thereof. Each possibility is a separate embodiment of the invention.

According to a further embodiment, the present invention provides a pharmaceutical composition comprising any combination of CB2 receptor inverse agonist of formula I, a mixed CB2/SERM of formula II, JTE-907, SR144528 or a salt thereof and a pharmaceutically acceptable carrier, for treatment of a disorder selected from the group consisting of developmental coordination disorder, stereotypic movement disorder, autism spectrum disorders, obsessive-compulsive disorder (OCD), bacterial-induced tic disorder, pediatric autoimmune neuropsychiatric disorders-associated with streptococcal infections (PANDAS), chorea (Sydenham's chorea (SC), chorea minor, chorea gravidarum, drug-induced chorea), drug-induced repetitive behaviors, akathisia, dyskinesias, Wernicke-Korsakoff syndrome, a tic disorder including but not limited to Tourette syndrome, and a combination thereof. Each possibility is a separate embodiment of the invention.

In addition, the new results disclosed here support the therapeutic effects of combinations of a first therapeutic agent of formula I (e.g. 4'-O-methylhonokiol) and a second therapeutic agent selected from the group consisting of a therapeutic agent of formula II of formula II (e.g. raloxifene), cannabidiol (CBD) and its analogues cannabidivarin (CBDV), cannabiodiolic acid (CBDA), cannabigerol (CBG) and its analogues CBGA and CBGV, $\Delta^9$-tetrahydrocannabinol ($\Delta^9$-THC) and its analogue THCV, cannabinol (CBN), palmitoylethanolamide (PEA) and other N-acylethanolamines, omega-3 fatty acids, phosphatidylserine, rosmarinic acid, guanfacine, noradrenaline agonists e.g. clonidine, antipsychotic drugs e.g. HU-308, BCP, cannabidiol (CBD), pimozide, haloperidol, aripiprazole, dopamine-depleting agent e.g. tetrabenazine, acetylcholine release blockers e.g. botulinum toxin, benzodiazepines, stimulants and dopamine/norepinephrine reuptake inhibitors e.g. methylphenidate, amphetamine and its analogues, lisdexamfetamine, atomoxetine, SSRIs such as fluoxetine, sertraline, citalopram, escitalopram, fluvoxamine and paroxetine and combinations thereof, for treatment of a disorder selected from the group consisting of developmental coordination disorder, stereotypic movement disorder, autism spectrum disorders, obsessive-compulsive disorder (OCD), bacterial-induced tic disorder, pediatric autoimmune neuropsychiatric disorders-associated with streptococcal infections (PANDAS), chorea (Sydenham's chorea (SC), chorea minor, chorea gravidarum, drug-induced chorea), drug-induced repetitive behaviors, akathisia, dyskinesias, Wernicke-Korsakoff syndrome, a tic disorder including but not limited to Tourette syndrome, and a combination thereof. Each possibility is a separate embodiment of the invention.

In addition, the new results disclosed herein support the therapeutic effects of combinations of a first therapeutic agent of HU-308 and a second therapeutic agent BCP, cannabidiol (CBD) and its analogues cannabidivarin (CBDV), cannabiodiolic acid (CBDA), cannabigerol (CBG) and its analogues CBGA and CBGV, $\Delta^9$-tetrahydrocannabinol ($\Delta^9$-THC) and its analogue THCV, cannabinol (CBN), palmitoylethanolamide (PEA) and other N-acylethanolamines, omega-3 fatty acids, phosphatidylserine, rosmarinic acid, guanfacine, noradrenaline agonists e.g. clonidine, antipsychotic drugs e.g. cannabidiol (CBD), pimozide, haloperidol, aripiprazole, dopamine-depleting agent e.g. tetrabenazine, acetylcholine release blockers e.g. botulinum toxin, benzodiazepines, stimulants and dopamine/norepinephrine reuptake inhibitors e.g. methylphenidate, amphetamine and its analogues, lisdexamfetamine, atomoxetine, SSRIs such as fluoxetine, sertraline, citalopram, escitalopram, fluvoxamine and paroxetine and combinations thereof, for treatment of a disorder selected from the group consisting of developmental coordination disorder, stereotypic movement disorder, autism spectrum disorders, obsessive-compulsive disorder (OCD), bacterial-induced tic disorder, pediatric autoimmune neuropsychiatric disorders-associated with streptococcal infections (PANDAS), chorea (Sydenham's chorea (SC), chorea minor, chorea gravidarum, drug-induced chorea), drug-induced repetitive behaviors, akathisia, dyskinesias, Wernicke-Korsakoff syndrome, a tic disorder including but not limited to Tourette syndrome, and a combination thereof. Each possibility is a separate embodiment of the invention.

According to other embodiments, the average daily therapeutically effective amount of the active agent in the pharmaceutical composition administered to a human or non-human subject is in a range selected from the group consisting of about 0.0001-6000 mg/kg, from about 0.0001-0.01 mg/kg about 0.01-1 mg/kg, about 1-100 mg/kg, about 100-1000 mg/kg or about 1000-6000 mg/kg according to patient's age, subject's age, subject's species, composition's effectiveness, the active agent and the mode of administration, wherein said at least one selected active agent selected from 0.0001-6000 mg/kg is co-administered in a single dosage form together with said CB2 receptor modulator 0.0001-6000 mg/kg. Each possibility is a separate embodiment of the invention.

In some embodiments, there is provided a method of treatment of a mental, movement or behavioral disorder in a human or non-human subject in need thereof with a composition, in any mode of administration, including but not limited to administration in a slow-release/long-active formulations given on a daily basis, of the present disclosure wherein the average daily amount of said 4-0-methylhonokiol (MH) or raloxifene or HU-308 or BCP administered to a human or non-human subject is in a range selected from the group consisting of 0.0001-0.01 mg, 0.01-0.1 mg, 0.1-1 mg, 1-10 mg, 10-mg, 20-50 mg, 50-100 mg, 100-200 mg, 200-1000 mg, 1000-5000 mg or 5000-10000 mg according patient's age, subject's age, subject's species, composition's effectiveness, active agent and the mode of administration, wherein said at least one selected active agent 0.0001-10000 mg is co-administered in a single dosage form together with said CB2 receptor modulator 0.0001-10000 mg according to the patient's age, subject's age, subject's species, composition's effectiveness, active agent and the mode of administration. Each possibility is a separate embodiment of the invention.

In some embodiments, there is provided a method of treatment of a mental, movement or behavioral disorder in human or non-human subject in need thereof with a delayed-release composition (such as compositions for a slow-release, slow-acting form of medication prepared as a capsule or a depot injection given for example but not limited by intramuscular injection, which are administrated every 1 week or once a month to up to every six months) of the present disclosure wherein the average amount of a single administration of said 4-0-methylhonokiol (MH) or raloxifene or HU-308 or BCP administered is in a range selected from the group consisting of 0.0001-0.001 mg, 0.001-0.01 mg, 0.01-0.1 mg, 0.1-10 mg, 10-100 mg, 100-200 mg, 200-300 mg, 300-400 mg, 500-600 mg, 600-700 mg, 700-800 mg or 800-1000 mg, 1000-1500 mg, 1000-2000 mg, 2000-5000 mg, 5000-10000 mg according to the patient's age, subject's age, subject's species, composition's effectiveness, active agent and the mode of administration. Each possibility is a separate embodiment of the invention.

According to an embodiment, there is provided a method of treatment of a mental, movement or behavioral disorder in a human or non-human subject in need thereof with a composition of the present disclosure, wherein said at least one selected active agent 0.001-10000 mg is co-administered in a single dosage form together with said CB2 receptor modulator 0.001-10000 mg according to the patient's age, subject's age, subject's species, composition's effectiveness, active agent and the mode of administration. Each possibility is a separate embodiment of the invention.

CB2 Receptor Inverse Agonists

Aspects of present invention disclose previously unknown indications of the compounds of formula I and formula II.

The present invention extends and provides additional methods for the treatment of the above disorders. The present invention provides methods for the treatment comprising administering to a subject in need of such treatment a pharmaceutical composition comprising a therapeutically effective amount of a CB2 inverse agonist or a CB2 inverse agonist/selective estrogen receptor modulator (SERM) ligand.

The inventors have discovered and disclosed in the co-pending U.S. Patent Application 2016/0089349 that a pharmaceutical composition comprising MH is effective in tic disorder, TS and/or Attention-deficit hyperactive disorder (ADHD) in murine models.

4'-O-Methylhonokiol (2-(4-Methoxy-3-prop-2-enylphenyl)-4-prop-2-enylphenol; CAS number 68592-15-4, designated herein M1 or MH) is a CB2 receptor mixed-type agonist/inverse agonist, naturally found in the flowers of *Magnolia grandiflora* and *Magnolia virginiana*.

The inventors have also discovered and disclosed in U.S. Pat. No. 9,486,419 that a pharmaceutical composition comprising a CB2 inverse agonist/selective estrogen receptor modulator (SERM) ligand is effective in treating ADHD/ADD, hyperactivity and/or obsessive/compulsive disorder (OCD) in murine models.

The present invention provides a method for the treatment of a behavior disorders, comprising administering to a subject in need of such treatment a pharmaceutical composition comprising a therapeutically effective amount of a CB2 receptor inverse agonist of general formula I:

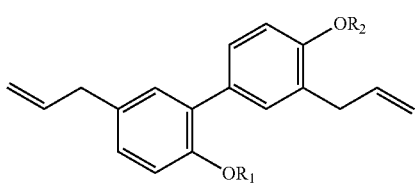

I or a salt thereof and a pharmaceutically acceptable carrier, wherein $R_1$ and $R_2$ are each independently selected from the group consisting of hydrogen, $C_1$-$C_8$ alkyl, $C_3$-$C_8$ cycloalkyl, $C_1$-$C_8$ haloalkyl, or $C_3$-$C_8$ cyclohaloalkyl, and wherein $R_1$ and $R_2$ are not both hydrogen, wherein the psychiatric disorder is selected from the group consisting of developmental coordination disorder, stereotypic movement disorder, autism spectrum disorders, obsessive-compulsive disorder (OCD), bacterial-induced tic disorder, pediatric autoimmune neuropsychiatric disorders-associated with streptococcal infections (PANDAS), chorea (Sydenham's chorea (SC), chorea minor, chorea gravidarum, drug-induced chorea), drug-induced repetitive behaviors, akathisia, dyskinesias, Wernicke-Korsakoff syndrome and a combination thereof. Each possibility is a separate embodiment of the invention.

The compounds represented by the general formula I may have various pharmaceutically acceptable salts due to the hydroxyl group, if present. Unless specified otherwise, the pharmaceutically acceptable salt includes all possible hydroxyl salts, including alkali metal salts such as sodium, potassium, and lithium, and alkaline earth metal salts such as calcium and magnesium salts. According to some embodiments, the pharmaceutically acceptable salt of the compound of general formula I includes sodium, potassium, or calcium. These salts may be prepared according to the methods known in the art.

According to a certain embodiment, the CB2 receptor inverse agonist is 4'-O-methylhonokiol (MH) of the formula I or formula III:

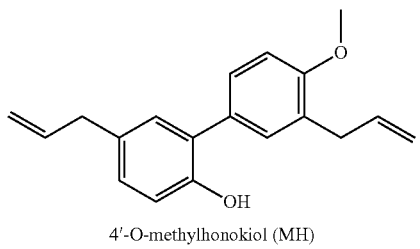 [SMILES: C=CCc1ccc(O)c(-c2ccc(OC)c(CC=C)c2)c1]

4'-O-methylhonokiol (MH)

While the present invention is exemplified by 4'-O-methylhonokiol as a CB2 receptor mixed-type agonist/inverse agonist, other CB2 receptor ligands, which exerts a similar pharmacological profile and inverse agonistic effect on CB2 receptors at the level of cAMP production as determined in assays well known in the art (see herein above), can be effective in treating mental, movement and behavioral disorders in accordance with the teachings of the present invention and a tic disorder, such as TS, and/or ADHD in accordance with teachings disclosed in U.S. Pat. No. 9,486,419.

Thus, according to another aspect, the present invention provides a composition and a method for the treatment of mental, movement and behavioral disorders, the method comprising administering to a subject in need of such treatment a pharmaceutical composition comprising a therapeutically effective amount of a CB2 receptor inverse agonist, wherein the CB2 receptor inverse agonist is a mixed selective CB2 inverse agonist/SERM ligand, and wherein the behavior disorders are selected from developmental coordination disorder, stereotypic movement disorder, autism spectrum disorders, obsessive-compulsive disorder (OCD), bacterial-induced tic disorder, pediatric autoimmune neuropsychiatric disorders-associated with streptococcal infections (PANDAS), chorea (Sydenham's chorea (SC), chorea minor, chorea gravidarum, drug-induced chorea), drug-induced repetitive behaviors, akathisia, dyskinesias, Wernicke-Korsakoff syndrome, a tic disorder including but not limited to Tourette syndrome and a combination thereof.

According to some embodiments, the mixed selective CB2 inverse agonist/SERM ligand is selected from the group consisting of raloxifene, bazedoxifene, lasofoxifene, tamoxifen, afimoxifene, arzoxifene, ormeloxifene, toremifene, ospemifene, analogues, derivatives or a combination thereof.

According to further embodiments, the mixed selective CB2 inverse agonist/SERM ligand is selected from the group consisting of raloxifene, bazedoxifene, lasofoxifene and tamoxifen.

In some embodiments, the CB2 receptor inverse agonist used to implement the teachings of the present invention is a mixed selective CB2 inverse agonist/SERM ligand such as, but not limited to, raloxifene.

According to some embodiments, the efficacy of the mixed selective CB2 inverse agonist/SERM ligand to treat disorders does not involve modulation of plasma LH, FSH and/or LHRH levels.

According to other embodiments, the efficacy of the mixed selective CB2 inverse agonist/SERM ligand to treat tic/repetitive disorders does not require binding to estrogen receptors.

In another embodiment, the present invention provides a method for treating behavior disorders comprising administering to a subject in need of such treatment a pharmaceutical composition comprising a therapeutically effective amount of a mixed selective CB2 receptor inverse agonist/ SERM ligand of general formula II:

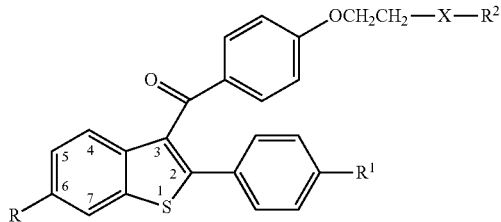

wherein

X is a bond, CH$_2$, or CH$_2$CH$_2$;

R and R$^1$, independently, are selected from the group consisting of hydrogen, hydroxyl, C$_1$-C$_6$ alkoxy, C$_1$-C$_6$-acyloxy, C1-C$_6$-alkoxy-C$_2$-C$_6$-acyloxy, R$_3$-substituted aryloxy, R$_3$-substituted aroyloxy, R$^4$-substituted carbonyloxy, chloro, and bromo;

R$^2$ is a heterocyclic ring selected from the group consisting of pyrrolidino, piperidino, or hexamethyleneimino;

R$^3$ is C$_1$-C$_3$-alkyl, C1-C3-alkoxy, hydrogen, or halo; and

R$^4$ is C$_1$-C$_6$-alkoxy or aryloxy; or a pharmaceutically acceptable salt thereof.

In an additional embodiment, the CB2 receptor inverse agonist is N-(benzo[1,3]dioxol-5-ylmethyl)-7-methoxy-2-oxo-8-pentyloxy-1,2-dihydroquinoline-3-carboxamide known as JTE 907 (CAS No. 282089-49-0) or its analogs or derivatives.

In a further embodiment, the CB2 receptor inverse agonist is the CB2 receptor inverse agonist is N-(benzo[1,3]dioxol-5-ylmethyl)-7-methoxy-2-oxo-8-pentyloxy-1,2-dihydroquinoline-3-carboxamide (JTE 907), (SR 144528, CAS number 192703-06-3) or its analogs or derivatives. JTE 907 at a dose of 0.2 mg/kg reversed the effect of DOI on head twitch frequency and reduced compulsive behavior in mice (FIG. 8A-B). These results point that the therapeutic effect of highly selective CB2 receptor inverse agonist in a human or non-human subject can be from about 0.016 mg/kg.

In an embodiment, there is provided a method of treatment of a vocal and/or motor disorder, wherein the disorder is selected from the group consisting of developmental coordination disorder, stereotypic movement disorder, autism spectrum disorders, obsessive-compulsive disorder (OCD), bacterial-induced tic disorder, pediatric autoimmune neuropsychiatric disorders associated with streptococcal infections (PANDAS), chorea (Sydenham's chorea (SC), chorea minor, chorea gravidarum, drug-induced chorea), drug-induced repetitive behaviors, akathisia, dyskinesias, Wernicke-Korsakoff syndrome, ADHD, a tic disorder including but not limited to Tourette syndrome, and combinations thereof, wherein acute, transient or chronic, by administration to a subject in need thereof of a composition comprising a therapeutically effective dose of JTE 907 (CAS number 282089-49-0) in a pharmaceutically acceptable carrier in the range of 0.0001 mg/kg to 6000 mg/kg in human or non-human subjects, according to patient's age, subject's age, subject's species, composition's effectiveness, active agent and the mode of administration.

In another embodiment, there is provided a method of treatment of a disorder, wherein the disorder is selected from the group consisting of developmental coordination disorder, stereotypic movement disorder, autism spectrum disorders, obsessive-compulsive disorder (OCD), bacterial-induced tic disorder, pediatric autoimmune neuropsychiatric disorders associated with streptococcal infections (PANDAS), chorea (Sydenham's chorea (SC), chorea minor, chorea gravidarum, drug-induced chorea), drug-induced repetitive behaviors, akathisia, dyskinesias, Wernicke-Korsakoff syndrome, ADHD, a tic disorder including but not limited to Tourette syndrome, and combinations thereof, wherein acute, transient or chronic by administration to a subject in need thereof of a composition comprising a therapeutically effective dose of SR 144528 in a pharmaceutically acceptable carrier in the range of 0.0001 mg/kg to 6000 mg/kg in human or non-human subjects.

In an embodiment, there is provided a method for treating mental, movement and behavioral disorders comprising administering to a subject in need of such treatment a pharmaceutical composition comprising a CB2 receptor inverse agonist and/or a CB2 receptor negative allosteric modulators that possibly, but not necessarily, act as mixed-type agonists or mixed-type CB2 receptor inverse agonists/ selective estrogen receptor modulators (mixed CB2/SERM ligands) for the treatment of a disorder, wherein the disorder is selected from the group consisting of developmental coordination disorder, stereotypic movement disorder, autism spectrum disorders, obsessive-compulsive disorder (OCD), bacterial-induced tic disorder, pediatric autoimmune neuropsychiatric disorders associated with streptococcal infections (PANDAS), chorea (Sydenham's chorea (SC), chorea minor, chorea gravidarum, drug-induced chorea), drug-induced repetitive behaviors, akathisia, dyskinesias, Wernicke-Korsakoff syndrome, a tic disorder including but not limited to Tourette syndrome, ADHD and combinations thereof, wherein acute, transient or chronic.

In another embodiment, there is provided a method for treating mental, movement and behavioral disorders comprising administering to a subject in need of such treatment a pharmaceutical composition comprising a fixed drug combination comprising therapeutically effective amounts of at least two therapeutic agents selected from the group consisting of an agent according to formula I, an agent according to formula II, phytocannabinoids, cannabidiol (CBD) and its analogues cannabidivarin (CBDV), cannabidiolic acid (CBDA), cannabigerol (CBG) and its analogues CBGA and CBGV, Δ$^9$-tetrahydrocannabinol (Δ$^9$-THC) and its analogue THCV, cannabinol (CBN), N-acylethanolamines such as but not limited to palmitoylethanolamide (PEA), guanfacine, noradrenaline agonists e.g. clonidine, antipsychotic drugs e.g. HU-308, BCP, CBD, pimozide, haloperidol, aripiprazole, dopamine-depleting agent e.g. tetrabenazine, acetylcholine release blockers e.g. botulinum toxin, benzodiazepines, stimulants and dopamine/norepinephrine reuptake inhibitors e.g. methylphenidate, amphetamine and its analogous, lisdexamfetamine, atomoxetine, SSRIs such as fluoxetine, sertraline, citalopram, escitalopram, fluvoxamine and paroxetine and combinations thereof.

In general, a particular ligand which binds to a particular receptor is said to have affinity for that receptor.

A measure of affinity is often determined using a binding assay, for example, a competition or displacement assay, in which a candidate ligand competes with, or displaces, a known (or reference) ligand with a known (or reference) affinity. Such assays yield an inhibition constant (Ki) for the candidate ligand. The Ki value is inversely proportional to the affinity of the candidate ligand for the receptor. Thus, a low Ki value signifies a high affinity. In general, a Ki value of 10 μM or less is considered to be a pharmaceutically meaningful affinity for the receptor, and indicates that the candidate compounds is in fact a ligand for that receptor.

Assays for determining cannabinoid receptor affinity are well known. For example, radio-ligand displacement assays using tissues that contain the CB2 receptor (spleen, CB2 transfected cell lines) are common. An example of suitable radio-labeled known ligand is tritium-labeled CP55940 (a CB1/CB2 receptor agonist).

According to some embodiments of the present invention, the CB2 inverse agonist has a CB2 receptor inhibition constant (Ki) of 10 µM or less. According to additional embodiments, the Ki is 1 µM or less; 500 nM or less; 100 nM or less; 50 nM or less; 25 nM or less; 10 nM or less; 5 nM or less; 2 nM or less; or 1 nM or less. Each possibility is a separate embodiment of the present invention.

According to other embodiments, the range of Ki is: from 0.01 nM to 10 µM; from 0.1 nM to 1 µM; from 0.1 nM to 500 nM; from 0.1 nM to 100 nM; from 1 nM to 100 nM; from 1 nM to 50 nM. Each possibility is a separate embodiment of the present invention.

According to the principles of the present invention, the CB2 receptor inverse agonists of the present invention show higher affinity/selectivity to CB2 receptors than to CB1 receptors. It should be appreciated that the Ki value of a CB2 receptor inverse agonist of some embodiments of the present invention towards CB2 receptors as compared to CB1 receptors is at least 10 times lower, at least 20 times lower, at least 25 times lower, at least 30 times lower, at least 40 times lower, at least 50 times lower, at least 100 times lower, at least 500 times lower or at least 1000 times lower. Each possibility is a separate embodiment of the present invention.

Pharmaceutical Compositions

The pharmaceutical compositions disclosed herein are administered and dosed in accordance with good medical practice, taking into account the clinical condition of the individual patient, the disease to be treated, the site and method of administration, scheduling of administration, patient age, sex, body weight, treatment with drugs and other factors known to medical practitioners.

The therapeutically effective dose can be determined by a person having ordinary skill in the art upon perusal of the disclosure according to known considerations. The dose is typically effective to achieve therapeutic improvement according to an appropriate measure by a person having ordinary skill in the art, and in some embodiments includes, but is not limited to, improvement of the subject functioning and/or improvement or elimination of symptoms and other indicators.

The therapeutically effective dose of the CB2 receptor inverse agonist, a mixed CB2/SERM agent, a CB2 receptor agonist can range from about group consisting of about 0.0001-6000 mg/kg, about 0.0001-0.001 mg/kg, about 0.001-0.01 mg/kg, about 0.01-1 mg/kg, from about 1-100, about 100-1000 mg/kg or about 1000-6000 mg/kg according to patient's age, subject's age, subject's species, composition's effectiveness, active agent and the mode of administration. Each possibility is a separate embodiment of the invention.

In an embodiment, there is provided a method of treatment of a mental, movement or behavioral disorder in a patient in need thereof with a composition, in any mode of administration, including but not limited to administration in a slow-release/long-active formulations given on a daily basis, of the present disclosure wherein the average daily amount of said 4-0-methylhonokiol (MH) or raloxifene or HU-308 or BCP administered is in a range selected from the group consisting of 0.0001-0.001 mg, 0.001-0.01 mg, 0.01-0.1 mg, 0.1-1 mg, 1-10 mg, 10-20 mg, 20-50 mg, 50-100 mg, 100-200 mg, 200-1000 mg, 1000-10000 mg according to the patient's age, subject's age, subject's species, composition's effectiveness, active agent and the mode of administration.

In an embodiment, there is provided a method of treatment of a mental, movement or behavioral disorder in a patient in need thereof with a delayed-release composition (such as compositions for a slow-release, slow-acting form of medication prepared as a capsule or a depot injection given for example but not limited by intramuscular injection, which are administrated every 1 week, every 2 weeks, every 3 weeks, or once a month to up to every six months) of the present disclosure wherein the average amount of a single administration of said 4-0-methylhonokiol (MH) or raloxifene or HU-308 or BCP administered is in a range selected from the group consisting of 0.0001-0.001 mg, 0.001-0.01 mg, 0.01-0.1 mg, 0.1-1 mg, 1-10 mg, 10-20 mg, 20-50 mg, 50-100 mg, 100-200 mg, 200-1000 mg, 1000-10000 mg according to the patient's age, subject's age, subject's species, composition's effectiveness, active agent and the mode of administration.

The average daily dose of the CB2 receptor inverse agonist, a mixed CB2/SERM agent, or CB2 receptor agonist for a human subject (such as a human child, weighing between about 10 kg and about 40 kg or a human adult, weighing between about 40 kg and about 120 kg) can be about, 0.001 mg, 0.01 mg, about 0.05 mg, about 0.1 mg, about 0.5 mg, about 1 mg, about 2 mg, about 5 mg, about 10 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 200 mg, about 300 mg, about 400 mg, about 500 mg, about 1000 mg, about 3000 mg, about 6000 mg or about 10000 mg.

In some embodiments, the daily dose of the CB2 receptor inverse agonist, a mixed CB2/SERM agent or CB2 receptor agonist for a human subject (such as a human child, weighing between about 10 kg and about 40 kg or a human adult, weighing between about 40 kg and about 120 kg) can be between 0.0001 and 10000 mg, 0.0001 and 100 mg, 0.0001 and 80 mg, 0.0001 and 50 mg, 0.0001 and 30 mg, 0.0001 and 20 mg, 0.0001 and 10 mg, 0.0001 and 5 mg, 0.0001 and 1 mg, 0.0001 and 0.1 mg, 0.0001 and 0.01 mg, 0.0001 and 0.001 mg, between 0.001 and 500 mg, 0.001 and 100 mg, 0.001 and 50 mg, 0.001 and 30 mg, 0.001 and 20 mg, 0.001 and 10 mg, 0.001 and 5 mg, 0.001 and 1 mg, 0.001 and 0.1 mg, between 0.01 and 1000 mg, 0.01 and 500 mg, 0.01 and 100 mg, 0.01 and 50 mg, 0.01 and 30 mg, 0.01 and 20 mg, 0.01 and 10 mg, 0.01 and 5 mg, 0.01 and 1 mg, 0.01 and 0.1 mg, 0.01 and 0.5 mg, 0.01 and 0.05 mg, 0.1 and 500 mg, 0.1 and 100 mg, 0.1 and 50 mg, 0.1 and 30 mg, 0.1 and 20 mg, 0.1 and 15 mg, 00.1 and 10 mg, 0.1 and 5 mg, 0.1 and 3 mg, 0.1 and 2 mg, 0.1 and 1 mg, 0.1 and 0.5 mg, 0.1 and 1 mg, 1 and 500 mg, 1 and 400 mg, 1 and 300 mg, 1 and 200 mg, 1 and 100 mg, 1 and 95 mg, 1 and 90 mg, 1 and 85 mg, 1 and 80 mg, 1 and 75 mg, 1 and 70 mg, 1 and 65 mg, 1 and 60 mg, 1 and 55 mg, 1 and 50 mg, 1 and 45 mg, 1 and 40 mg, 1 and 35 mg, 1 and 30 mg, 1 and 25 mg, 1 and 20 mg, 1 and 15 mg, 1 and 10 mg, 1 and 5 mg, 1 and 2 mg, 5 and 500 mg, 5 and 400 mg, 5 and 300 mg, 5 and 200 mg, 5 and 100 mg, 5 and 95 mg, 5 and 90 mg, 5 and 85 mg, 5 and 80 mg, 5 and 75 mg, 5 and 70 mg, 5 and 65 mg, 5 and 60 mg, 5 and 55 mg, 5 and 50 mg, 5 and 45 mg, 5 and 40 mg, 5 and 35 mg, 5 and 30 mg, 5 and 25 mg, 5 and 20 mg, 5 and 15 mg, 5 and 10 mg, 10 and 1000 mg, 10 and 500 mg, 10 and 400 mg, 10 and 300 mg, 10 and 200 mg, 10 and 100 mg, 10 and 95 mg, 10 and 90 mg, 10 and 85 mg, 10 and 80 mg, 10 and 75 mg, 10 and 70 mg, 10 and 65 mg, 10 and 60 mg, 10 and 55 mg, 10 and 50 mg, 10 and 45 mg, 10 and 40 mg, 10 and 35 mg, 10 and 30 mg, 10 and 25 mg, 10 and 20 mg, 10 and 15 mg, 15 and 1000 mg, 15 and 500 mg, 15 and 400 mg, 15 and 300 mg, 15 and 200 mg, 15 and 100 mg, 15 and 95 mg, 15 and 90 mg, 15 and 85 mg, 15 and 80 mg, 15 and 75 mg, 15 and 70 mg, 15 and 65 mg, 15 and 60 mg, 15 and 55 mg, 15 and 50 mg, 15 and 45 mg, 15 and 40 mg, 15 and 35 mg, 15 and 30 mg, 15 and 25 mg, 15 and 20 mg, 20 and 1000 mg, 20 and 500 mg, 20 and 400 mg, 20 and 300 mg, 20 and 200 mg, 20 and 100 mg, 20 and 95 mg, 20 and 90 mg, 20 and 85 mg, 20 and 80 mg, 20 and 75 mg, 20 and 70 mg, 20 and 65 mg, 20 and 60 mg, 20 and 55 mg, 20 and 50 mg, 20 and 45 mg, 20 and 40 mg, 20 and 35 mg, 20 and 30 mg, 20 and 25 mg, 25 and 100 mg, 25 and 95 mg, 25 and 90 mg, 25 and 85 mg, 25 and 80 mg, 25 and 75 mg, 25 and 70 mg, 25 and 65 mg, 25 and 60 mg, 25 and 55 mg, 25 and 50 mg, 25 and 45 mg, 25 and 40 mg, 25 and 35 mg, 25 and 30 mg, 30 and 1000 mg, 30 and 500 mg, 30 and 400 mg, 30 and 300 mg, 30 and 200 mg, 30 and 100 mg, 30 and 95 mg, 30 and 90 mg, 30 and 85 mg, 30 and 80 mg, 30 and 75 mg, 30 and 70 mg, 30 and 65 mg, 30 and 60 mg, 30 and 55 mg, 30 and 50 mg, 30 and 45 mg, 30 and 40 mg, 30 and 35 mg, 35 and 1000 mg, 35 and 500 mg, 35 and 400 mg, 35 and 300 mg, 35 and 200 mg, 35 and 100 mg, 35 and 95 mg, 35 and 90 mg, 35 and 85 mg, 35 and 80 mg, 35 and 75 mg, 35 and 70 mg, 35 and 65 mg, 35 and 60 mg, 35 and 55 mg, 35 and 50 mg, 35 and 45 mg, 35 and 40 mg, 40 and 1000 mg, 40 and 500 mg, 40 and 400 mg, 40 and 300 mg, 40 and 200 mg, 40 and 100 mg, 40 and 95 mg, 40 and 90 mg, 40 and 85 mg, 40 and 80 mg, 40 and 75 mg, 40 and 70 mg, 40 and 65 mg, 40 and 60 mg, 40 and 55 mg, 40 and 50 mg, 40 and 45 mg, 50 and 1000 mg, 50 and 500 mg, 50 and 400 mg, 50 and 300 mg, 50 and 200 mg, 50 and 100 mg, 50 and 95 mg, 50 and 90 mg, 50 and 85 mg, 50 and 80 mg, 50 and 75 mg, 50 and 70 mg, 50 and 65 mg, 50 and 60 mg, 50 and 55 mg, 60 and 1000 mg, 60 and 500 mg, 60 and 400 mg, 60 and 300 mg, 60 and 200 mg, 60 and 100 mg, 60 and 95 mg, 60 and 90 mg, 60 and 85 mg, 60 and 80 mg, 60 and 75 mg, 60 and 70 mg, 60 and 65 mg, 65 and 1000 mg, 65 and 500 mg, 65 and 400 mg, 60 and 300 mg, 60 and 200 mg, 65 and 100 mg, 65 and 95 mg, 65 and 90 mg, 65 and 85 mg, 65 and 80 mg, 65 and 75 mg, 65 and 70 mg, 70 and 1000 mg, 70 and 500 mg, 70 and 400 mg, 70 and 300 mg, 70 and 200 mg, 70 and 100 mg, 70 and 95 mg, 70 and 90 mg, 70 and 85 mg, 70 and 80 mg, 70 and 75 mg, 75 and 1000 mg, 75 and 500 mg, 75 and 400 mg, 75 and 300 mg, 75 and 200 mg, 75 and 100 mg, 75 and 95 mg, 75 and 90 mg, 75 and 85 mg, 75 and 80 mg, 80 and 1000 mg, 80 and 500 mg, 80 and 400 mg, 80 and 300 mg, 80 and 200 mg, 80 and 100 mg, 80 and 95 mg, 80 and 90 mg, 80 and 85 mg, 85 and 1000 mg, 85 and 500 mg, 85 and 400 mg, 85 and 300 mg, 85 and 200 mg, 85 and 100 mg, 85 and 95 mg, 85 and 90 mg, 90 and 1000 mg, 90 and 500 mg, 90 and 400 mg, 90 and 300 mg, 90 and 200 mg, 90 and 100 mg, 90 and 95 mg, 95 and 1000 mg, 95 and 500 mg, 95 and 400 mg, 95 and 300 mg, 95 and 200 mg, 95 and 100 mg, 100 and 1000 mg, 100 and 500 mg, 100 and 400 mg, 100 and 300 mg, 100 and 200 mg, 200 and 1000 mg, 200 and 500 mg, 200 and 400 mg, 200 and 300 mg, 300 and 1000 mg, 300 and 500 mg, 300 and 400 mg, 400 to 1000 mg, 400 to 500 mg, 500 to 1000, 1000 and 100000 mg, 1000 and 800 mg, 1000 and 2000 mg, 1000 and 3000 mg, 1000 and 4000 mg, 1000 and 5000 mg, 1000 and 6000 mg, 1000 and 7000 mg, 1000 and 8000 mg, 1000 and 9000 mg, 1000 and 1500 mg, 1500 and 2000 mg, 1500 and 3500 mg, 3500 and 4500 mg, 4500 and 5500 mg, 5000 and 6000 mg, 5500 and 6500 mg, 6000 and 7500 mg, 7000 and 8500 mg, 8000 and 9500 mg, 9000 and 10000 mg. Each possibility is a different embodiment of the invention. Each possibility is a separate embodiment of the invention.

The CB2 receptor inverse agonist can be administered to a human or non-human subject once every 6 months, once every 3 months to about once a month, once a week to about 3 times per day, for example once per week, twice per week, 3 times per week, 4 times per week, 5 times per week, 6 times per week, once per day, twice per day or 3 times per day or 4 times per day to a patient in need thereof. Each possibility is a separate embodiment of the invention.

The therapeutically effective dose of the active agent that is not a CB2 ligand can range from about group consisting of about 0.0001-10000 mg/kg, about 0.0001-0.001 mg/kg, about 0.001-0.01 mg/kg, about 0.01-1 mg/kg, from about 1-100, about 100-1000 mg/kg, about 1000-6000 mg/kg or about 6000-10000 mg/kg, according to patient's age, subject's age, subject's species, composition's effectiveness, active agent and the mode of administration. Each possibility is a separate embodiment of the invention.

The average daily dose of the active agent that is not a CB2 ligand for a human subject (such as a human child, weighing between about 10 kg and about 40 kg or a human adult, weighing between about 40 kg and about 120 kg) can be about, 0.001 mg, 0.01 mg, about 0.05 mg, about 0.1 mg, about 0.5 mg, about 1 mg, about 2 mg, about 5 mg, about 10 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 200 mg, about 300 mg, about 400 mg, about 500 mg, about 1000 mg, about 3000 mg, about 6000 mg, about 10000 mg, about 15000 mg, about 20000 mg.

In some embodiments, the daily dose of the active agent that is not a CB2 ligand for a human subject (such as a human child, weighing between about 10 kg and about 40 kg or a human adult, weighing between about 40 kg and about 120 kg) can be between 0.0001 and 20000 mg, 0.0001 and 100 mg, 0.0001 and 80 mg, 0.0001 and 50 mg, 0.0001 and 30 mg, 0.0001 and 20 mg, 0.0001 and 10 mg, 0.0001 and 5 mg, 0.0001 and 1 mg, 0.0001 and 0.1 mg, 0.0001 and 0.01 mg, 0.0001 and 0.001 mg, between 0.001 and 500 mg, 0.001 and 100 mg, 0.001 and 50 mg, 0.001 and 30 mg, 0.001 and 20 mg, 0.001 and 10 mg, 0.001 and 5 mg, 0.001 and 1 mg, 0.001 and 0.1 mg, between 0.01 and 1000 mg, 0.01 and 500 mg, 0.01 and 100 mg, 0.01 and 50 mg, 0.01 and 30 mg, 0.01 and 20 mg, 0.01 and 10 mg, 0.01 and 5 mg, 0.01 and 1 mg, 0.01 and 0.1 mg, 0.01 and 0.5 mg, 0.01 and 0.05 mg, 0.1 and 500 mg, 0.1 and 100 mg, 0.1 and 50 mg, 0.1 and 30 mg, 0.1 and 20 mg, 0.1 and 15 mg, 00.1 and 10 mg, 0.1 and 5 mg, 0.1 and 3 mg, 0.1 and 2 mg, 0.1 and 1 mg, 0.1 and 0.5 mg, 0.1 and 1 mg, 1 and 500 mg, 1 and 400 mg, 1 and 300 mg, 1 and 200 mg, 1 and 100 mg, 1 and 95 mg, 1 and 90 mg, 1 and 85 mg, 1 and 80 mg, 1 and 75 mg, 1 and 70 mg, 1 and 65 mg, 1 and 60 mg, 1 and 55 mg, 1 and 50 mg, 1 and 45 mg, 1 and 40 mg, 1 and 35 mg, 1 and 30 mg, 1 and 25 mg, 1 and 20 mg, 1 and 15 mg, 1 and 10 mg, 1 and 5 mg, 1 and 2 mg, 5 and 500 mg, 5 and 400 mg, 5 and 300 mg, 5 and 200 mg, 5 and 100 mg, 5 and 95 mg, 5 and 90 mg, 5 and 85 mg, 5 and 80 mg, 5 and 75 mg, 5 and 70 mg, 5 and 65 mg, 5 and 60 mg, 5 and 55 mg, 5 and 50 mg, 5 and 45 mg, 5 and 40 mg, 5 and 35 mg, 5 and 30 mg, 5 and 25 mg, 5 and 20 mg, 5 and 15 mg, 5 and 10 mg, 10 and 1000 mg, 10 and 500 mg, 10 and 400 mg, 10 and 300 mg, 10 and 200 mg, 10 and 100 mg, 10 and 95 mg, 10 and 90 mg, 10 and 85 mg, 10 and 80 mg, 10 and 75 mg, 10 and 70 mg, 10 and 65 mg, 10 and 60 mg, 10 and 55 mg, 10 and 50 mg, 10 and 45 mg, 10 and 40 mg, 10 and 35 mg, 10 and 30 mg, 10 and 25 mg, 10 and 20 mg, 10 and 15 mg, 15 and 1000 mg, 15 and 500 mg, 15 and 400 mg, 15 and 300 mg, 15 and 200 mg, 15 and 100 mg, 15 and 95 mg, 15 and 90 mg, 15 and 85 mg, 15 and 80 mg, 15 and 75 mg, 15 and 70 mg, 15 and 65 mg, 15 and 60 mg, 15 and 55 mg, 15 and 50 mg, 15 and 45 mg, 15 and 40 mg, 15 and 35 mg, 15 and 30 mg, 15 and 25 mg, 15 and 20 mg, 20 and 1000 mg, 20 and 500 mg, 20 and 400 mg, 20 and 300 mg, 20 and 200 mg, 20 and 100 mg, 20 and 95 mg, 20 and 90 mg, 20 and 85 mg, 20 and 80 mg, 20 and 75 mg, 20 and 70 mg, 20 and 65 mg, 20 and 60 mg, 20 and 55 mg, 20 and 50 mg, 20 and 45 mg, 20 and 40 mg, 20 and 35 mg, 20 and 30 mg, 20 and 25 mg, 25 and 100 mg, 25 and 95 mg, 25 and 90 mg, 25 and 85 mg, 25 and 80 mg, 25 and 75 mg, 25 and 70 mg, 25 and 65 mg, 25 and 60 mg, 25 and 55 mg, 25 and 50 mg, 25 and 45 mg, 25 and 40 mg, 25 and 35 mg, 25 and 30 mg, 30 and 1000 mg, 30 and 500 mg, 30 and 400 mg, 30 and 300 mg, 30 and 200 mg, 30 and 100 mg, 30 and 95 mg, 30 and 90 mg, 30 and 85 mg, 30 and 80 mg, 30 and 75 mg, 30 and 70 mg, 30 and 65 mg, 30 and 60 mg, 30 and 55 mg, 30 and 50 mg, 30 and 45 mg, 30 and 40 mg, 30 and 35 mg, 35 and 1000 mg, 35 and 500 mg, 35 and 400 mg, 35 and 300 mg, 35 and 200 mg, 35 and 100 mg, 35 and 95 mg, 35 and 90 mg, 35 and 85 mg, 35 and 80 mg, 35 and 75 mg, 35 and 70 mg, 35 and 65 mg, 35 and 60 mg, 35 and 55 mg, 35 and 50 mg, 35 and 45 mg, 35 and 40 mg, 40 and 1000 mg, 40 and 500 mg, 40 and 400 mg, 40 and 300 mg, 40 and 200 mg, 40 and 100 mg, 40 and 95 mg, 40 and 90 mg, 40 and 85 mg, 40 and 80 mg, 40 and 75 mg, 40 and 70 mg, 40 and 65 mg, 40 and 60 mg, 40 and 55 mg, 40 and 50 mg, 40 and 45 mg, 50 and 1000 mg, 50 and 500 mg, 50 and 400 mg, 50 and 300 mg, 50 and 200 mg, 50 and 100 mg, 50 and 95 mg, 50 and 90 mg, 50 and 85 mg, 50 and 80 mg, 50 and 75 mg, 50 and 70 mg, 50 and 65 mg, 50 and 60 mg, 50 and 55 mg, 60 and 1000 mg, 60 and 500 mg, 60 and 400 mg, 60 and 300 mg, 60 and 200 mg, 60 and 100 mg, 60 and 95 mg, 60 and 90 mg, 60 and 85 mg, 60 and 80 mg, 60 and 75 mg, 60 and 70 mg, 60 and 65 mg, 65 and 1000 mg, 65 and 500 mg, 65 and 400 mg, 60 and 300 mg, 60 and 200 mg, 65 and 100 mg, 65 and 95 mg, 65 and 90 mg, 65 and 85 mg, 65 and 80 mg, 65 and 75 mg, 65 and 70 mg, 70 and 1000 mg, 70 and 500 mg, 70 and 400 mg, 70 and 300 mg, 70 and 200 mg, 70 and 100 mg, 70 and 95 mg, 70 and 90 mg, 70 and 85 mg, 70 and 80 mg, 70 and 75 mg, 75 and 1000 mg, 75 and 500 mg, 75 and 400 mg, 75 and 300 mg, 75 and 200 mg, 75 and 100 mg, 75 and 95 mg, 75 and 90 mg, 75 and 85 mg, 75 and 80 mg, 80 and 1000 mg, 80 and 500 mg, 80 and 400 mg, 80 and 300 mg, 80 and 200 mg, 80 and 100 mg, 80 and 95 mg, 80 and 90 mg, 80 and 85 mg, 85 and 1000 mg, 85 and 500 mg, 85 and 400 mg, 85 and 300 mg, 85 and 200 mg, 85 and 100 mg, 85 and 95 mg, 85 and 90 mg, 90 and 1000 mg, 90 and 500 mg, 90 and 400 mg, 90 and 300 mg, 90 and 200 mg, 90 and 100 mg, 90 and 95 mg, 95 and 1000 mg, 95 and 500 mg, 95 and 400 mg, 95 and 300 mg, 95 and 200 mg, 95 and 100 mg, 100 and 1000 mg, 100 and 500 mg, 100 and 400 mg, 100 and 300 mg, 100 and 200 mg, 200 and 1000 mg, 200 and 500 mg, 200 and 400 mg, 200 and 300 mg, 300 and 1000 mg, 300 and 500 mg, 300 and 400 mg, 400 to 1000 mg, 400 to 500 mg, 500 to 1000, 1000 and 100000 mg, 1000 and 800 mg, 1000 and 2000 mg, 1000 and 3000 mg, 1000 and 4000 mg, 1000 and 5000 mg, 1000 and 6000 mg, 1000 and 7000 mg, 1000 and 8000 mg, 1000 and 9000 mg, 1000 and 1500 mg, 1500 and 2000 mg, 1500 and 3500 mg, 3500 and 4500 mg, 4500 and 5500 mg, 5000 and 6000 mg, 5500 and 6500 mg, 6000 and 7500 mg, 7000 and 8500 mg, 8000 and 9500 mg, 9000 and 10000 mg, 10000 and 15000 mg, 15000 and 20000 mg. Each possibility is a different embodiment of the invention. Each possibility is a separate embodiment of the invention.

In some embodiments, the subject is a human. In some embodiments, the human subject is a human child. In some embodiments, the human subject is a human teenager. In some embodiments, the human subject is a human adult. In other embodiments, the subject is an animal.

The pharmaceutical compositions of the present invention can be administered through any suitable route, such as orally or parenterally including intravenously, intraarterially, intramuscularly, intraperitoneally, subcutaneously, intranasally, vaginally or rectally.

The pharmaceutical compositions of the present invention can be manufactured by any suitable method or combination of methods as known in the art with which a person having ordinary skill in the art is familiar and include conventional mixing, dissolving, granulating, dragee-making, levigating, emulsifying, encapsulating, entrapping or lyophilizing. The pharmaceutical compositions typically include a pharmaceutically acceptable carrier optionally comprising diluents, excipients or auxiliaries. Proper formulation can be done by a person having ordinary skill in the art with reference to standard procedures as disclosed, for example, in "Remington's Pharmaceutical Sciences," Mack Publishing Co., Easton, Pa., latest edition, which is incorporated herein by reference as if fully set forth herein.

For topical administration, the pharmaceutical compositions of the present invention can be formulated as solutions, gels, ointments, creams, suspensions, sprays, and the like as are well-known in the art.

In an embodiment, the oral compositions of the present invention are stable self-emulsifying compositions, comprising a therapeutically effective amount of at least one CB2 receptor modulator or a SERM and a self-emulsifying vehicle, wherein the active agents are substantially solubilized. Examples of such stable self-emulsifying compositions are presented in the co-pending PCT application WO2017149392 which is included in its entirety by reference. For example, the compositions can be formulated as a stable self-emulsifying drug delivery system (SEDDS) comprising at least one CB2 receptor modulator, optionally at least one antipsychotic agent and a self-emulsifying vehicle comprising at least one oil, at least one surfactant with HLB<9, at least one surfactant with HLB>13, at least one co-surfactant and at least one antioxidant and/or free-radical scavenger. The antioxidant and/or free-radical scavenger can be selected from vitamin E, d-alpha-tocopherol (1-10% w/w), dl-alpha-tocopherol (2-15% w/w), dl-alpha-tocopheryl acetate (2-15% w/w), mixed tocopherols (alpha, beta, gamma—1-10% w/w), d-alpha-tocopheryl acetate (2-15% w/w), butylated hydroxyanisole (BHA, 0.01-0.5% w/w), tocophersolan (TPGS, tocopherol PEG ester succinate) (2-10% w/w), vitamin C, beta-carotene, butylated hydroxy toluene, butylated hydroxyanisole or other FDA-approved antioxidant listed in the FDA's Inactive Ingredients Database (IID) or Ph. Eur. and combinations thereof.

Systemic compositions include those designed for administration by injection, e.g., subcutaneous, intravenous, intramuscular, intrathecal or intraperitoneal injection, as well as those designed for transdermal, transmucosal, inhalation, gastroresistant, oral or pulmonary administration.

For injection, the pharmaceutical compositions of the present invention can be formulated in aqueous solutions, preferably in physiologically compatible buffers such as Hanks's solution, Ringer's solution, or physiological saline buffer. The solution may contain inactive ingredients such as suspending, stabilizing and/or dispersing agents.

Alternatively, the pharmaceutical composition can be in powder form for reconstitution with a suitable vehicle, e.g., sterile pyrogen-free water, before use.

For transmucosal administration, penetrants appropriate to the barrier to be permeated can be used in the composition. Such penetrants are generally known in the art.

For oral administration, the pharmaceutical compositions of the present invention can be readily formulated by combining a selected CB2 receptor inverse agonist with one of the pharmaceutically acceptable carriers well known in the art. Such carriers enable the composition to be formulated as tablets, pills, dragees, capsules, liquids, gels, syrups, slurries, suspensions, sprays, and the like, for oral ingestion by a patient to be treated. For oral solid formulations such as, for example, powders, capsules and tablets, suitable excipients include fillers such as sugars, e.g. lactose, sucrose, mannitol and sorbitol; cellulose preparations such as maize starch, wheat starch, rice starch, potato starch, gelatin, gum tragacanth, methyl cellulose, hydroxypropyl-methylcellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms can be sugar-coated or enteric-coated using standard techniques.

For oral liquid compositions such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the composition can take the form of tablets, lozenges, sprays, and the like, formulated in conventional manner.

For administration by inhalation, the pharmaceutical compositions of the present invention can be delivered in the form of an aerosol spray from pressurized packs or a nebulizer, with the use of a suitable propellant, e.g., dichlorodifluoromethane, trichlorofluoromethane, dichloro-tetrafluoro-ethane or carbon dioxide. In the case of a pressurized aerosol, the dosage unit may be determined by providing a valve to deliver a metered amount. Capsules and cartridges of gelatin for use in an inhaler or insufflator may be formulated containing a powder mix of the composition and a suitable powder base such as lactose or starch.

The pharmaceutical compositions of the present invention can be formulated for rectal or vaginal administration such as suppositories or retention enemas, e.g., containing conventional suppository bases such as cocoa butter or other glycerides.

The pharmaceutical compositions of the present invention can be formulated as long-acting depot formulations. Such long acting compositions may be administered by implantation (for example subcutaneously or intramuscularly) or by intramuscular injection. Thus, for example, the composition may be formulated as a depot preparation with suitable polymeric or hydrophobic materials (for example as an emulsion in an acceptable oil) or ion exchange resins, or as sparingly soluble derivatives, for example, as a sparingly soluble salt. For example, a composition may comprise a sustained-release system, such as semipermeable matrices of solid polymers containing the CB2 inverse agonist. Various sustained-release materials have been established and are well known by those skilled in the art. Sustained-release capsules may, depending on their chemical nature, release the composition for a few weeks up to over 100 days. Newly sustained-release capsules may release the composition up to over 6 months.

Due to their hydrophobic nature, the compounds of the present invention are readily dissolved in lipids. In some embodiments, other pharmaceutical delivery systems, such as compositions including liposomes, can be employed for implementing the teaching of the present invention.

In some embodiments, the CB2 receptor inverse agonist such as MH or SERM can be co-administered with an additional active pharmaceutical ingredient, for example an additional active pharmaceutical ingredient for the treatment of a psychiatric disorder, either via a single dosage form (making up the same composition) or by separate administration of each active pharmaceutical ingredient, wherein the separate administration is sequential or concurrent.

In some embodiments, there is provided a method of treatment of a disorder selected from the group consisting of developmental coordination disorder, stereotypic movement disorder, autism spectrum disorders, obsessive-compulsive disorder (OCD), bacterial-induced repetitive behavior, NMDA antibody-related encephalitis, autoimmune antibody-mediated mental disorder, autoimmune antibody-mediated psychosis, pediatric autoimmune neuropsychiatric disorders associated with streptococcal infections (PANDAS), chorea (Sydenham's chorea (SC), chorea minor, chorea gravidarum, drug-induced chorea), drug-induced repetitive behaviors, akathisia, dyskinesias, dystonias, cramps and spasms, tremors, restless leg syndrome, moving toes/fingers syndrome, involuntary movement, extrapyramidal movement disorders, Wernicke-Korsakoff syndrome and combinations thereof, wherein acute, transient or chronic, the method comprising administering to a human or non-human subject in need thereof a therapeutically effective dose of a pharmaceutical composition comprising at least one active agent selected from the group of CB2 receptor inverse agonists and mixed CB2/SERM ligands consisting of (i) a CB2 receptor inverse agonist of formula I:

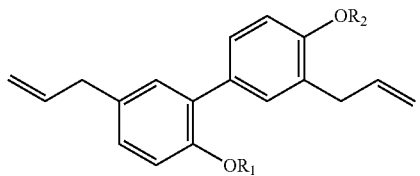

or a salt thereof and a pharmaceutically acceptable carrier, wherein R1 and R2 are each independently selected from the group consisting of hydrogen, C1-C8 alkyl, C3-C8 cycloalkyl, C1-C8 haloalkyl, or C3-C8 cyclohaloalkyl, wherein R1 and R2 are not both hydrogen (ii) a mixed CB2/SERM ligand of formula II

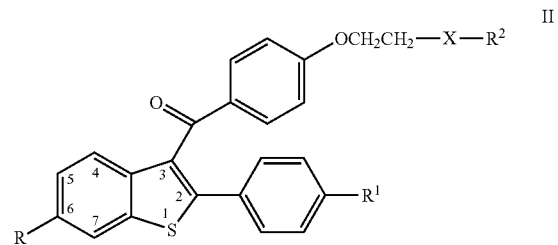

wherein

X is a bond, $CH_2$, or $CH_2CH_2$;

R and $R^1$, independently, are hydrogen, hydroxyl, $C_1$-$C_6$ alkoxy, $C_1$-$C_6$-acyloxy, $C_1$-$C_6$-alkoxy-$C_2$-$C_6$-acyloxy, $R_3$-substituted aryloxy, $R^3$-substituted aroyloxy, $R^4$-substituted carbonyloxy, chloro, or bromo;

$R^2$ is a heterocyclic ring selected from the group consisting of pyrrolidino, piperidino, or hexamethyleneimino;

$R^3$ is $C_1$-$C_3$-alkyl, C1-C3-alkoxy, hydrogen, or halo; and $R^4$ is $C_1$-$C_6$-alkoxy or aryloxy; or a pharmaceutically acceptable salt thereof.

(iii) the CB2 receptor inverse agonist N-(benzo[1,3]dioxol-5-ylmethyl)-7-methoxy-2-oxo-8-pentyloxy-1,2-dihydroquinoline-3-carboxamide (JTE 907), (iv) the CB2 receptor inverse agonist 5-(4-Chloro-3-methylphenyl)-1-[(4-methylphenyl)methyl]-N-[(1S,2S,4R)-1,3,3-trimethylbicyclo[2.2.1]heptan-2-yl]-1H-pyrazole-3-carboxamide (SR 144528) or (v) any combinations of (i)-(iv);

wherein active agents (i)-(v) are formulated in a pharmaceutically effective carrier.

In some other embodiments, there is provided the above composition and method, wherein in formula I R1 is hydrogen and R2 is methyl, and the CB2 receptor inverse agonist is 4'-O-Methylhonokiol.

In some embodiments, there is provided the above composition and method of treatment of a disorder, wherein the disorder is selected from pediatric autoimmune neuropsychiatric disorders associated with streptococcal infections (PANDAS), NMDA antibody-related encephalitis, autoimmune antibody-mediated mental disorder, autoimmune antibody-mediated psychosis, chorea and combinations thereof.

In some alternative embodiments, the disorder is an autism spectrum disorder.

In some other alternative embodiments, the disorder is selected from akathisia, dyskinesias and combinations thereof.

In some embodiments, there is provided a method of treatment of a disorder selected from the group consisting of Tourette syndrome, developmental coordination disorder, stereotypic movement disorder, autism spectrum disorders, bacterial-induced repetitive behavior, NMDA antibody-related encephalitis, autoimmune antibody-mediated mental disorder, autoimmune antibody-mediated psychosis, pediatric autoimmune neuropsychiatric disorders-associated with streptococcal infections (PANDAS), chorea (Sydenham's chorea (SC), chorea minor, chorea gravidarum, drug-induced chorea), drug-induced repetitive behaviors, akathisia, dyskinesias, dystonias, cramps and spasms, tremors, restless leg syndrome, moving toes/fingers syndrome, involuntary movement, stereotypic movement disorder, extrapyramidal movement disorders, Wernicke-Korsakoff syndrome and a combination thereof wherein acute, transient or chronic, comprising administering to a subject in need thereof a pharmaceutical composition comprising a therapeutically effective amount of a mixed CB2/SERM ligand in a pharmaceutically acceptable carrier, wherein the mixed CB2/SERM ligand has formula II:

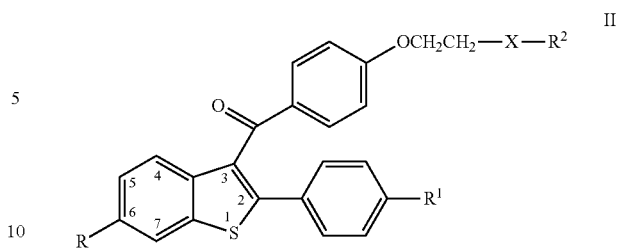

wherein

X is a bond, $CH_2$, or $CH_2CH_2$;

R and $R^1$, independently, are hydrogen, hydroxyl, $C_1$-$C_6$ alkoxy, $C_1$-$C_6$-acyloxy, $C_1$-$C_6$-alkoxy-$C_2$-$C_6$-acyloxy, $R_3$-substituted aryloxy, $R_3$-substituted aroyloxy, $R^4$-substituted carbonyloxy, chloro, or bromo;

$R^2$ is a heterocyclic ring selected from the group consisting of pyrrolidino, piperidino, or hexamethyleneimino;

$R^3$ is $C_1$-$C_3$-alkyl, C1-C3-alkoxy, hydrogen, or halo; and $R^4$ is $C_1$-$C_6$-alkoxy or aryloxy; or a pharmaceutically acceptable salt thereof.

In some embodiments, there is provided the above composition and method of treatment of a disorder, wherein the said mixed CB2/SERM ligand is selected from the group consisting of raloxifene, bazedoxifene, lasofoxifene, tamoxifen, afimoxifene, arzoxifene, ormeloxifene, toremifene, ospemifene, and a combination thereof.

In some alternative embodiments, there is provided the above composition and method of treatment of a disorder, wherein the said mixed CB2/SERM ligand is raloxifene.

In some embodiments, there is provided a method of treatment of a disorder, wherein the disorder is selected from the group consisting of ADHD (Attention-deficit hyperactivity disorder), Tourette syndrome (TS), tic disorder, vocal disorder, developmental coordination disorder, stereotypic movement disorder, autism spectrum disorders, obsessive-compulsive disorder (OCD), bacterial-induced repetitive behavior, NMDA antibody-related encephalitis, autoimmune antibody-mediated mental disorder, autoimmune antibody-mediated psychosis, pediatric autoimmune neuropsychiatric disorders associated with streptococcal infections (PANDAS), chorea (Sydenham's chorea (SC), chorea minor, chorea gravidarum, drug-induced chorea), drug-induced repetitive behaviors, akathisia, dyskinesias, dystonias, cramps and spasms, tremors, restless leg syndrome, moving toes/fingers syndrome, involuntary movement, stereotypic movement disorder, extrapyramidal movement disorders, Wernicke-Korsakoff syndrome and combinations thereof, wherein acute, transient or chronic, comprising administering to a subject in need thereof a fixed drug combination composition comprising therapeutically effective amounts of at least two therapeutic agents selected from the group consisting of an agent according to formula I, an agent according to formula II, phytocannabinoids, cannabidiol (CBD) and its analogues cannabidivarin (CBDV), cannabiodiolic acid (CBDA), cannabigerol (CBG) and its analogues CBGA and CBGV, Δ9-tetrahydrocannabinol ($Δ^9$-THC) and its analogue THCV, cannabinol (CBN), N-acylethanolamines, palmitoylethanolamide (PEA), omega-3 fatty acids, phosphatidylserine, rosmarinic acid, guanfacine, a noradrenaline agonist, clonidine, antipsychotic drugs, HU-308, BCP, pimozide, haloperidol, aripiprazole, a dopamine-depleting agent tetrabenazine, an acetylcholine release blocker, botulinum toxin, a benzodiazepine, a stimulant and a dopamine/norepinephrine reuptake inhibitor, methylphenidate, amphetamine and its analogues, lisdexamfetamine, atomoxetine, an SSRI, wherein the SSRI is selected from the group consisting of fluoxetine, sertraline, citalopram, escitalopram, fluvoxamine and paroxetine and combinations thereof.

In some embodiments, there is provided the above composition and method of treatment of a disorder, wherein said fixed drug combination comprises a therapeutically effective amount of an agent according to formula I, combined with a therapeutically effective amount of at least one additional active agent according to formula II or combinations thereof.

In some alternative embodiments, there is provided the above composition and method of treatment of a disorder, wherein in said fixed drug combination the agent of formula I is 4'-O-methylhonokiol and the agent of formula II is raloxifene.

In some other alternative embodiments, there is provided the above composition and method of treatment of a disorder, wherein in said fixed drug combination the agent of formula I is 4'-O-methylhonokiol and the at least one additional active agent is rosmarinic acid.

In some other alternative embodiments, there is provided the above composition and method of treatment of a disorder, wherein in said fixed drug combination the agent of formula II is raloxifene and the at least one additional active agent is rosmarinic acid.

In some other alternative embodiments, there is provided the above composition and method of treatment of a disorder, wherein in said fixed drug combination the active agent of formula I is 4'-O-methylhonokiol and the at least one additional active agent is an omega-3 fatty acid.

In some other alternative embodiments, there is provided the above composition and method of treatment of a disorder, wherein in said fixed drug combination the active agent of formula II is raloxifene and the at least one additional active agent is an omega-3 fatty acid.

In some other alternative embodiments, there is provided the above composition and method of treatment of a disorder, wherein in said fixed drug combination the agent of formula I is 4'-O-methylhonokiol and the at least one additional active agent is a stimulant drug.

In some embodiments, there is provided the above composition and method of treatment of a disorder, wherein the stimulant drug is selected from the group consisting of dopamine/norepinephrine reuptake inhibitor, methylphenidate, amphetamine and its analogues, lisdexamfetamine, atomoxetine and combinations thereof.

In some other alternative embodiments, there is provided the above composition and method of treatment of a disorder, wherein the active agent of formula I in the fixed drug combination is 4'-O-methylhonokiol and the at least one additional active agent is selected from Δ9-tetrahydrocannabinol ($\Delta^9$-THC) and its analogue THCV.

In some other alternative embodiments, there is provided the above composition and method of treatment of a disorder, wherein in said fixed drug combination the agent of formula I is 4'-O-methylhonokiol and the at least one additional active agent is a combination of Δ9-tetrahydrocannabinol ($\Delta^9$-THC) and palmitoylethanolamide (PEA).

In some other alternative embodiments, there is provided the above composition and method of treatment of a disorder, wherein in said fixed drug combination the agent of formula I is 4'-O-methylhonokiol and the at least one additional agent is cannabidiol (CBD) or its analogue CBDV.

In some other alternative embodiments, there is provided the above composition and method of treatment of a disorder, wherein the agent of formula I is 4'-O-methylhonokiol and the at least one additional active agent is selected from CBD and $\Delta^9$-tetrahydrocannabinol ($\Delta^9$-THC) or mixtures thereof.

In some embodiments, there is provided a method of treatment of any one of the above disorders, wherein acute, transient or chronic, according to any one of the methods detailed above, the method comprising administering to a human or non-human subject in need thereof a therapeutically effective dose of a pharmaceutical composition comprising at least one active agent selected from the group of CB2 receptor selective agonists wherein the CB2 receptor in a subject is absolutely dysfunctional.

In some embodiments, there is provided a composition and method of treatment according to any one of the methods detailed above, wherein the active agent is a CB2 receptor selective agonist selected from the group consisting of HU-308, BCP and mixtures thereof.

In some embodiments, there is provided a composition and method of treatment according to any one of the methods detailed above, wherein in combination compositions the at least one active agent exhibits at least one improved therapeutic effect selected from an enhanced therapeutic effect and a reduced psychoactive effect in a subject or, in the fixed drug combination compositions, an enhanced therapeutic effect in a subject compared to that of a single active agent.

In some embodiments, there is provided a method of treatment, comprising administering a composition, wherein the composition comprises two or more active agents, wherein administration of the two or more active agents to a subject in need thereof exhibits at least one improved therapeutic effect as compared to the effect obtained by a single active agent administered at the same concentration, wherein the improved effect is selected from an enhanced therapeutic effect, a reduced psychoactive effect, an enhanced therapeutic effect and a reduced psychoactive effect in the subject. In some embodiments, there is provided a method of treatment according to any one of the methods detailed above, wherein the therapeutically effective dose of the least one active agent is formulated in a pharmaceutically acceptable carrier.

In some embodiments, there is provided a method of treatment according to any one of the methods detailed above, wherein the therapeutically effective dose of at the least one active agent is formulated in a pharmaceutically acceptable carrier.

In some embodiments, there is provided a composition comprising at least one active agent selected from formula I, formula II, JTE 907, SR 144528, HU-308, BCP and combinations thereof, wherein formulated in a self-emulsifying carrier. In some embodiments, the active agent of Formula I is 4'-O-methylhonokiol. In some embodiments, the active agent of Formula II is raloxifene.

In some embodiments, there is provided the above composition, wherein the said self-emulsifying carrier is selected from Table I.

In some embodiments, there is provided the above composition wherein the composition is formulated as a stable self-emulsifying drug delivery system and wherein the composition comprises at least one oil, at least one surfactant HLB<9, at least one surfactant HLB>13, at least one co-surfactant, at least one antioxidant or free-radical scavenger.

In some embodiments, there is provided the above composition wherein the composition is formulated as a stable self-emulsifying drug delivery system and wherein the composition comprises:

from 10% w/w to 50% w/w of an oil selected from the group consisting of medium chain triglycerides, propylene glycol dicaprilate/dicaprate, medium chain mono- and diglycerides, acetylated mono- and diglycerides, sesame oil and olive oil and combinations thereof, from 20% w/w to 50% w/w of a surfactant HLB<9 selected from the group consisting of oleoyl polyoxyl-6 glycerides, linoleyl polyoxyl-6 glycerides (20-40%), Polysorbate 85 (Tween-85) polyoxyethylene (20-40% w/w), sorbitan trioleate (5-15% w/w), Span-80 (sorbitan monooleate) (5-25% w/w), polyglyceryl-3 dioleate (15-35% w/w) and glycerin monolinoleate (10-35% w/w), Polysorbate 80 (Tween-80) polyoxyethylene (20-40% w/w), Polysorbate 60 (Tween-60) polyoxyethylene (20-40% w/w), and combinations thereof, from 5% w/w to 50 w/w of a surfactant HLB>13 selected from the group consisting of polyoxylated castor oil (5-40% w/w), PEG 40 hydrogenated castor oil, PEG-15 hydroxystearate (5-25% w/w), caprylocaproyl polyoxyl-8 glycerides (10-20% w/w) and combinations thereof, from 5% w/w to 25% w/w of a surfactant HLB>13 selected from the group consisting of PEG-20 sorbitan monostearate, PEG-20 sorbitan monooleate (5-25%), PEG 40 stearate (5-25% w/w) and combinations thereof, from 0.5% w/w to 15 w/w of a co-surfactant selected from the group consisting of any lecithin (2-15% w/w), soy lecithin (>75% w/w phosphatidylcholine in oil, 1-10% w/w), soy lecithin PC content >50% (2-15% w/w), egg lecithin E-60 (1-5% w/w), egg lecithin E-80 (1-5% w/w), distearoylphosphatidylcholine (0.5-3% w/w) and combinations thereof, from 0.1% w/w to 5 w/w of an antioxidant or free radical scavenger selected from the group consisting of d-alpha-tocopherol (1-10% w/w), dl-alphatocopherol (2-15% w/w), dl-alpha-tocopheryl acetate (2-15% w/w), mixed tocopherols (alpha, beta, gamma—1-10% w/w), d-alpha-tocopheryl acetate (2-15% w/w), butylated hydroxyanisole (BHA, 0.01-0.5% w/w), tocophersolan (TPGS, tocopherol PEG ester succinate) (2-10% w/w) and combinations thereof, from about 1% w/w to about 10% w/w of ethyl alcohol, and from 1% w/w to 20% w/w of at least one active agent.

In some embodiments, there is provided the above composition, wherein the composition is formulated as a stable self-emulsifying drug delivery system and wherein the composition comprises:

from 30% w/w to 50% w/w capric/caprylic triglycerides,
from 30% w/w to 50% w/w oleoyl polyoxyl-6 glycerides,
from 5% w/w to 35% w/w polyoxylated castor oil,
from 7% w/w to 15% w/w PEG-20 sorbitan monostearate,
from 2% w/w to 10% w/w soy lecithin (75% phosphatidylcholine in oil),
from 1% w/w to 15% w/w d-alpha tocopherol and/or tocopherol acetate,
from 1% w/w to 20% w/w of at least one active agent.

In some embodiments, there is provided the above composition, wherein the composition is formulated in a dosage form selected from the group consisting of a solution, suspension, emulsion, powder, tablet, caplet, capsule, dragee, depot, granules, syrup, transdermal patch, spray, gastroresistant oral dosage, gastroresistant softgel capsule, cream, nasal dosage, sublingual dosage and suppository.

In some embodiments, there is provided the above composition, wherein the composition is formulated for oral, inhalation, transdermal, vaginal and/or rectal administration routes.

In some embodiments, there is provided a method of treatment of a disease or a disorder selected from ADHD (Attention-deficit hyperactivity disorder), Tourette syndrome (TS), a tic disorder, a vocal disorder, obsessive-compulsive disorder (OCD), developmental coordination disorder, stereotypic movement disorder, autism spectrum disorders, bacterial-induced repetitive behavior, NMDA antibody-related encephalitis, autoimmune antibody-mediated mental disorder, autoimmune antibody-mediated psychosis, pediatric autoimmune neuropsychiatric disorders associated with streptococcal infections (PANDAS), chorea (Sydenham's chorea (SC), chorea minor, chorea gravidarum, drug-induced chorea), drug-induced repetitive behaviors, akathisia, dyskinesias, dystonias, cramps and spasms, tremors, restless leg syndrome, moving toes/fingers syndrome, involuntary movement, stereotypic movement disorder, extrapyramidal movement disorders, Wernicke-Korsakoff syndrome, Parkinson's disease, amyotrophic lateral sclerosis, Alzheimer's disease, Huntington's disease, multiple sclerosis and combinations thereof, wherein acute, transient or chronic, epilepsy, seizures, diabetes, insulin resistance, hypertension, pain, anesthesia, inflammation, convulsions, infertility, aging, schizophrenia, schizoaffective disorder, bipolar disorder I and II, unipolar disorder, multiple personality disorder, psychotic disorders, depression, psychotic depression, depressive disorders, major depressive disorder, epilepsy, anxiety disorders, autistic spectrum disorder, enuresis, addiction, withdrawal symptoms associated with addiction, Asperger syndrome, oppositional defiant disorder, behavioral disturbance, agitation, psychosis/agitation associated with Alzheimer's disease, psychosis associated with Parkinson's disease, psychosis associated with drug of abuse, psychosis associated with psychedelic drug abuse, LSD-induced psychosis, steroid-induced schizophrenia, steroid-induced psychosis, Capgras syndrome; Fregoli syndrome; Cotard, personality disorders, borderline personality disorder, avoidant personality disorder, mania, dementia, anorexia, anorexia nervosa, eating disorders, narcolepsy, anxiety, generalized anxiety disorder, social anxiety disorder, body dismographic disorder, paranoid disorder, nightmares, agitation, post-traumatic stress disorder (PTSD), severe mood dysregulation, developmental coordination disorder, neuroinflammatory diseases, neurodegenerative diseases, liver associated-diseases, hepatitis, alcohol-related liver disease, fibromyalgia, gastrointestinal diseases, inflammatory bowel disease, Crohn's disease, ulcerative colitis, cancer, depression or anxiety that leads to metabolic diseases, metabolic diseases, infertility, cardiovascular diseases, osteoporosis, traumatic brain injury, cerebral ischemia, depression associated with any of the above clinical conditions, anxiety associated with any of the above clinical conditions, hyperactivity associated with any of the above clinical conditions, inattention associated with any of the above clinical conditions, involuntary movements associated with any of the above clinical conditions, cognitive deficits associated with any of the above clinical conditions, and combinations thereof, wherein the disorder is acute, transient or chronic disease, wherein comprising administering a therapeutically effective amount of the above self-emulsifying composition to a subject in need thereof, comprising at least one active agent selected from formula I, formula II and combinations thereof.

In some embodiments, there is provided a method of treatment of the above diseases or disorders, wherein the at least one active agent is selected from the group consisting of, HU-308, BCP and combinations thereof, and wherein the subject has absolute dysfunctional CB2 receptors.

In some embodiments, there is provided the above composition, wherein the composition comprises a self-emulsifying carrier.

In some embodiments, there is provided the above composition, wherein the composition is formulated in a dosage form selected from the group consisting of a solution, suspension, emulsion, powder, tablet, caplet, capsule, dragee, depot, granules, syrup, transdermal patch, spray, gastroresistant oral dosage, gastroresistant softgel capsule, cream, nasal dosage, sublingual dosage and suppository.

In some embodiments, there is provided the above composition, wherein the composition is formulated for oral, inhalation, transdermal, vaginal and/or rectal administration routes.

In some embodiments, there is provided the above method of treatment of a disease or a disorder, wherein the said composition is formulated as an injectable solution and wherein administered as intravenous injection, intra-arterial injection, intramuscular injection, intradermal injection, intraperitoneal injection, intrathecal injection, depot injection or subcutaneous injection.

In some embodiments, there is provided a method of treatment of the above disease or disorder, wherein the therapeutically effective amount of the at least one active agent in the composition administered to a human or non-human subject in need thereof is in a range selected from about 0.0001-0.005 mg/kg, 0.005-0.01 mg/kg, about 0.01-0.1 mg/kg, 0.1-2 mg/kg, about 2-5 mg/kg, about 5-10 mg/kg, about 10-30 mg/kg, about 30-100 mg/kg, about 100-1000 mg/kg and about 1000-6000 mg/kg according to the patient's age, subject's age, subject's species, composition's effectiveness, active agent and the mode of administration.

In some embodiments, there is provided a method of treatment of the above disease or disorder, wherein a composition comprising the therapeutically effective dose of at least one active agent in a pharmaceutically effective carrier is administered to a human or non-human subject in need thereof once every 6 months, once every 3 months to about once a month, once a week, about 3 times per day, once per week, twice per week, 3 times per week, 4 times per week, 5 times per week, 6 times per week, once per day, twice per day or 3 times per day or 4 times per day.

In some embodiments, there is provided a method of treatment of a disease or a disorder with a composition of this invention, wherein the subject in need thereof is an adult patient, a teenage patient or pediatric patient.

In some embodiments, there is provided a method of screening for a candidate active agent for the treatment of a mental disease treated by the methods and compositions of this invention, comprising operatively linking a reporter gene which expresses a detectable protein to a regulatory sequence for a gene selected from the group consisting of genes encoding CB1 receptor, CB2 receptor, GPR55, GPR18, GPR119, GABAA receptors, GABAB receptors, cyclooxygenase (COX) enzyme, COX-1, COX-2, COX-3 enzymes and combinations thereof, to produce a reporter construct;

transfecting a cell with the reporter construct;

exposing the transfected cell to a candidate active agent;

comparing the level of expression or function of the receptor before vs. after exposure to the candidate active agent, wherein an alteration in the level of expression after exposure is indicative of the candidate active agent being useful for the treatment of a mental disease.

In some embodiments, there is provided a kit comprising a custom array selected from a gene array, a probe array, a protein array, an array comprising a therapeutic agent, an array comprising a nucleic acid molecule which selectively hybridizes to a nucleic acid molecule, an array comprising a radioligand agent, an array comprising a cell or a kit component which expresses a patient's mutation, to at least one of the genes selected from genes encoding CB1 receptor, CB2 receptor, GPR55, GPR18, GPR119, GABAA receptors, GABAB receptors, cyclooxygenase (COX) enzyme, COX-1, COX-2, COX-3 enzymes and combination thereof, and instructions for use it in a combination with other genes, proteins or combination thereof.

In some embodiments, there is provided a kit comprising a pharmaceutical composition of this invention and instructions for use and optionally comprising a subject sample harvested from a body fluid selected from cerebrospinal fluid (CSF), blood, saliva, lymphatic fluid, urine or feces, or from a body organ selected from epithelial cells, spleen, skin, hair, spinal cord and brain.

EXAMPLES

Materials

The inverse agonist CB2 receptor ligand 4-O-methylhonokiol designated herein below M1 or MH was provided by Prof Gertsch, University of Bern, Switzerland (Schuehly et al., Chem. & Biol. 18:1053-64, 2011) or purified by Angene International Limited, at least 95% purified. Raloxifene, clomiphene citrate and DOI (($-$)-1-(2,5-dimethoxy-4-iodophenyl)-2-aminopropane hydrochloride or ($-$)-2,5-dimethoxy-4-iodoamphetamine hydrochloride), Cremophor EL and chemicals were purchased from Sigma-Aldrich, Israel. JTE-907 and SR141716A were obtained from Dr Iain Grieg, University of Aberdeen. HU-308 was purchased from Tocris, UK. BCP was provided by Prof Gertsch, University of Bern, Switzerland.

The solution of 4-O-methylhonokiol (M1 or MH), JTE-907, HU-308, BCP, raloxifene, clomiphene citrate was prepared in Cremophor EL/ethanol/saline (1:0.6:18) or in Cremophor EL/DMSO/saline (1:0.6:18).

The solution of DOI was prepared in saline.

Mice Models

1. CB2 receptor selective ligands or CB2/SERM ligands were injected intraperitoneally or orally at doses of 0.001 to 100 mg/kg one to two hours before the injection of DOI. In order to test the effect of DOI on head twitch responses, ear scratch and grooming responses, DOI was intraperitoneally injected at a dose of 1 mg/kg.

For the control group, mice pups were injected intraperitoneally or orally with an equivalent amount of the vehicle of Cremophor EL/ethanol/saline (1:0.6:18) or Cremophor EL/DMSO/saline (1:0.6:18) or an equivalent amount of VMHK formulation (according to Table 1) and saline according to the above schedule.

2. SR141716A at 1 to 20 mg/kg was subcutaneously injected on postnatal day 1 to 5. The tested drug, specifically MH or raloxifene, were injected on subcutaneously or intraperitoneally on postnatal days 5 to 14. For the control group, mice pups were injected intraperitoneally or orally with an equivalent amount of the vehicle Cremophor EL/ethanol/saline (1:0.6:18) or EL/DMSO/saline (1:0.6:18) or an equivalent amount of VMHK formulation (according to Table 1) and saline, according to the above schedule.

Assessment of Ultrasonic Vocals

Mice were recorded at the age of 5-7, 12-15, 20-25, 35-45 days with an ultrasonic voice recorder (AviSoft) from 20 to 100 kHz. A single mouse was recorded in a cage for 5 to 10 min (according to sex and type of treatment). The number and duration of events were analyzed.

Assessment of Head Twitch Response (HTR) Behavior:

After DOI or saline injection, mice were placed in a transparent glass cage 30×40×31 cm divided into squares of 7.5×7.5 cm. Head twitch responses (HTRs) were manually counted by an observer. The HTR in mice is a distinctive behavior that cannot be misplaced with other head movements. After 5 min habitation to the cage the HTR were counted every 3 min for 15 min (a total of 20 min in the cage).

Assessment of Ear Scratch Response (ESR) Behavior:

ESR behavior is a measure for urge-like behavior and often preceded HTRs. The ESR is a rapid scratching movement of the head, neck, ears, or other body surfaces by either hindlimbs. The number of ESRs was manually counted. Every ESR was also counted as a grooming. In some experiments, each ESR was considered as a separate episode if the animal moved. In some experiments, each ESR was considered as a separate episode for every ESR.

Assessment of Grooming Behavior:

Grooming behavior is a measure for anxiety. Grooming behavior in mice is characterized by licking its fur, groom with the forepaws, or scratch with any limb. Often the mouse will mix all of these grooming behaviors. The number of grooms was manually counted. In some experiments, each grooming behavior was considered as a separate episode if the animal moved its hindlimbs. In some experiments, each grooming behavior was considered as a separate episode for every grooming behavior.

Marble Burying Test (MBT)

Assessment of Marble Burying Frequency

Mice were habituated to the test room for 1 h. A mouse was injected with DOI as above and then placed in the experimental cage (white plastic 36×24.5×14.5 cm) filled with 5 cm sawdust for 5 min, in the absence of marbles. The mouse was taken out and twenty black glass were arranged 4 by 5 with 7 cm apart and 1 cm apart from the wells of the cage. Each mouse was tested for its marble burying activity for 30 min. Activity was videotaped with EthoVision and buried marbles were counted manually at the end of the experiment (after 30 min). A marble considered as buried when it was sawdust-covered by two third of its volume. Marbles that were moved were also counted.

Open-Field Test (Distance Moving and Center)

The activity in the MBT cage was analyzed with EthoVision. The total distance that each mouse travelled in the cage, the frequency and time it spend in the center area of the cage (center was defined as the area around six marbles in the center of the 4 by 5 arrangement) were graphed. The frequency and time in the center is a measure for the level of anxiety. A decrease in the total distance reflects a reduction in locomotor activity.

Example 1

In order to study the effect of the raloxifene compositions on repetitive behavior, C57BL/6JOlaHsd mice were intraperitoneally injected at age 3 weeks or 6 weeks with a single dose of raloxifene at 0.2-50 mg/kg or equivalent vehicle. One hour later mice were intraperitoneally injected a single dose of 1 mg/kg DOI or saline. HTR responses and ESR responses in mice were recorded.

Group 1: control mice were treated once with vehicle and once with saline;

Group 2: model mice were treated once with vehicle and once with DOI;

Group 3: drug tested mice were treated once with 10 mg/kg raloxifene and once with DOI;

The effects of raloxifene on repetitive behavior are shown in FIG. 1. At age 3 weeks, the model mice showed increased HTR frequency in the presence of DOI vs. the control mice. One hour after a single injection, raloxifene at 10 mg/kg reduced DOI-induced HTR frequency. These results show that mixed a CB2/SERM ligand reduces repetitive behavior.

Example 2

In order to further study the effect of the MH compositions on repetitive behavior, C57BL/6JOlaHsd mice were intraperitoneally injected at age 3 weeks or 6 weeks with a single dose of MH at 0.2-50 mg/kg or equivalent vehicle. One hour later mice were intraperitoneally injected a single dose of 1 mg/kg DOI or saline. HTR responses and ESR responses in mice were recorded.

Figure 2:
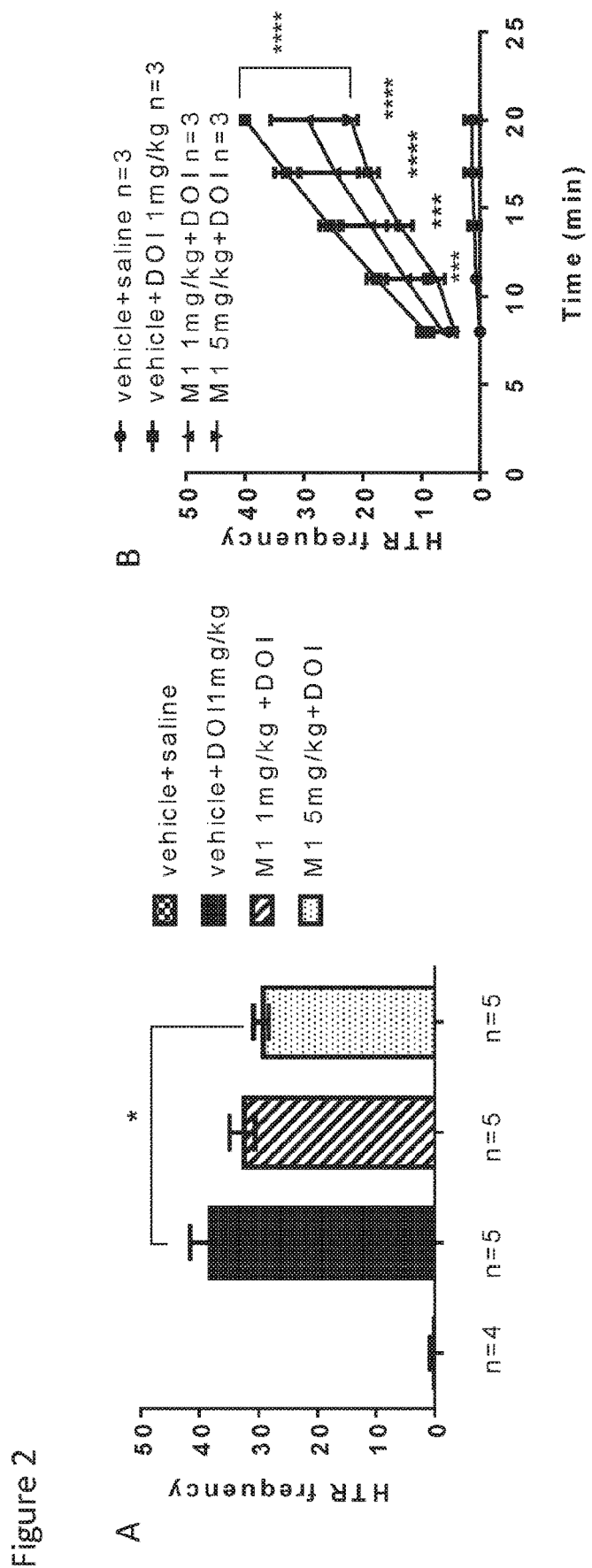
FIG. 2A-B shows that MH reversed the effect of DOI on the frequency of head twitch response (HTR) in 6 weeks old mice (FIG. 2A). Compared with the results in 6 weeks old mice (FIG. 2A), MH reversed the effect of DOI on head twitch response (HTR) frequency in 3 weeks old mice to a greater extent (FIG. 2B).

Group 1: control mice were treated once with vehicle and once with saline;

Group 2: model mice were treated once with vehicle and once with DOI;

Group 3: drug tested mice were treated once with 1 mg/kg MH and once with DOI;

Group 4: drug tested mice were treated once with 5 mg/kg MH and once with DOI;

The effects of MH on repetitive behavior are shown in FIG. 2 and FIG. 3A. In FIG. 2A, at age 6 weeks, the model mice showed increased HTR frequency in the presence of DOI vs. the control mice. Doses of 1 and 5 mg/kg MH reduced DOI-induced HTRs.

In FIG. 2B, at age 3 weeks, the model mice showed increased HTR frequency in the presence of DOI vs. the control mice. Doses of 1 and 5 mg/kg MH reduced DOI-induced HTRs. The results in FIG. 2B after 20 min from DOI injection show that the effect of MH to reverse DOI-induced HTR is higher at age 3 weeks than 6 weeks.

In FIG. 3A, DOI increased the ESR frequency vs. control mice. MH reduced the frequency of DOI-induced ESR behavior. These results show that MH reduces urge-like behavior.

Example 3

With a view to further study the effect of the MH compositions on repetitive behavior, C57BL/6JOlaHsd mice were intraperitoneally injected at age 3 weeks or 6 weeks with a single dose of MH at 0.2-50 mg/kg or equivalent vehicle. Optionally, one hour later mice received a single injection of saline (i.e. in the absence of DOI to test the effect of MH alone). HTR responses, ESR and grooming responses in mice were recorded.

Figure 4:
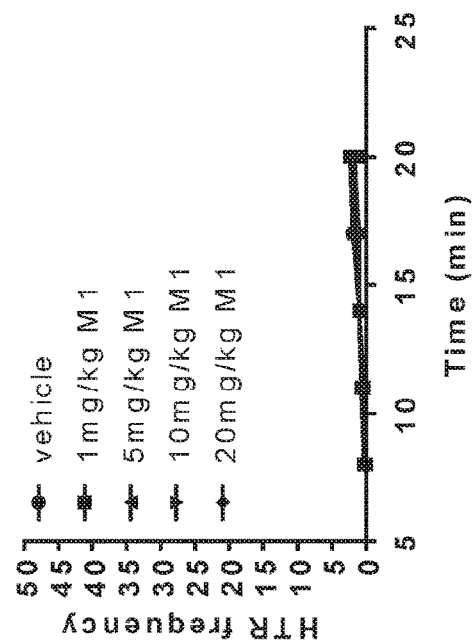
FIG. 4A-B are line graphs showing no effect of MH on DOI-induced head twitches in CB2 receptor knockout mice (n=3 in each group.
Figure 4:
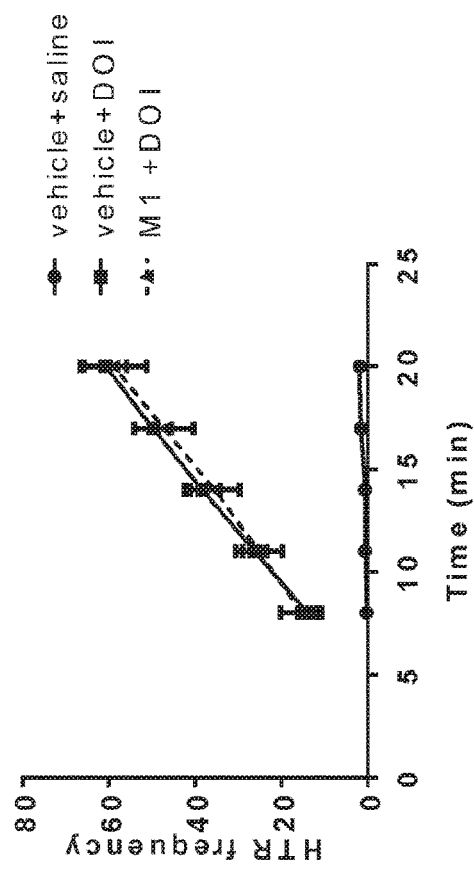

Group 1: control mice were treated once with vehicle (n=3);

Group 2-5: mice were treated once with M1 at doses 1-20 mg/kg (in each group n=3);

The effects of MH on repetitive behavior are shown in FIG. 3B and FIG. 4B. The results in FIG. 3B show that at age 6 weeks MH did not induce urge-like response at any dose. The results in FIG. 4B show that at age 6 weeks MH did not induce HTR at any dose.

Example 4

With a view to further study the effect of the MH compositions on repetitive behavior, CB2 receptor knockout mice (The Jackson Laboratory) were intraperitoneally injected at age 3 weeks or 6 weeks with a single dose of MH at 0.2-50 mg/kg or equivalent vehicle. One hour later mice were intraperitoneally injected a single dose of 1 mg/kg DOI or saline. HTR responses, grooming and ESR responses in mice were recorded.

Group 1: control mice were treated once with vehicle and once with saline (n=3);

Group 2: model mice were treated once with vehicle and once with DOI (n=5);

Group 3: drug tested mice were treated once with 5 mg/kg MH and once with DOI (n=4);

The effects of M1 on repetitive behavior in CB2 receptor knockout mice are shown in FIG. 4A. At age 6 weeks, DOI-increased HTR frequency in 6 weeks old CB2 receptor knockout mice. MH at 5 mg/kg MH did not reduce the DOI-induced HTR frequency. These results show that the effect of MH on HTR is through the CB2 receptors. Collectively with the results in FIG. 2, the results show that MH is acting through the CB2 receptors in the brain, but not exclusively, to control repetitive behavior.

Example 5

Figure 5:
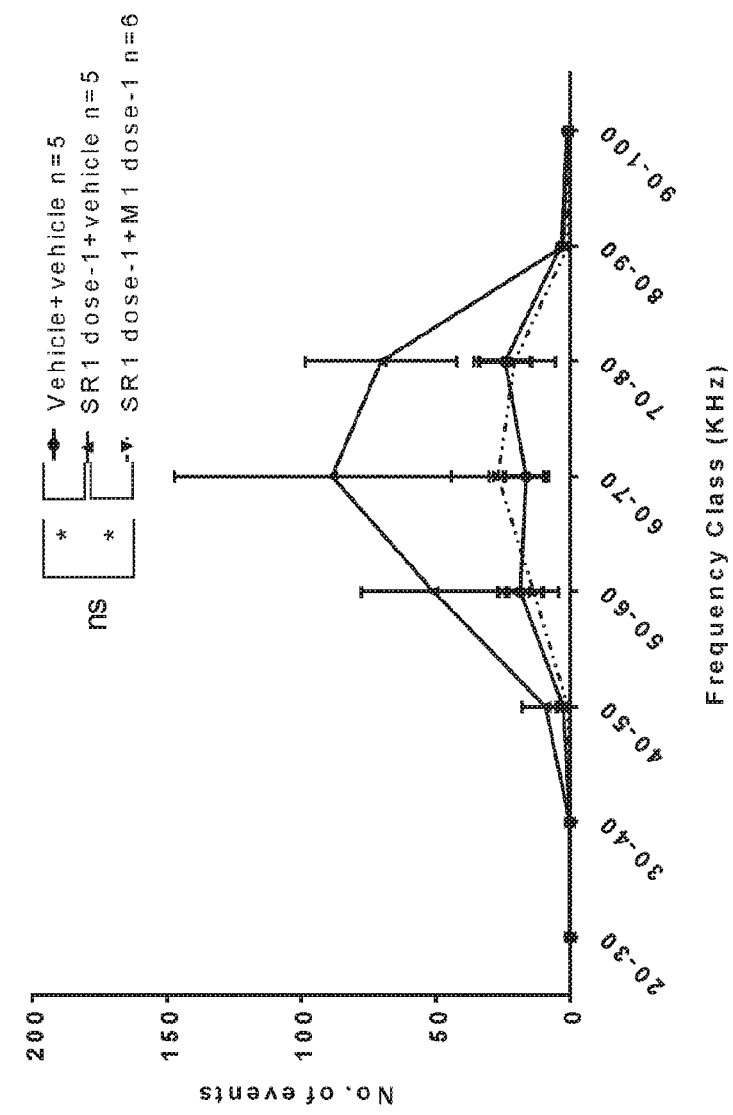
FIG. 5 shows the effect of SR141716A (SR1; dose-1 is 5 mg/kg) on vocal-like tics. Treatment with MH (dose-1 is 5 mg/kg) on postnatal age 13 days reversed the effect of SR17161A on vocals.

With a view to study the effect of the MH compositions on vocal tic-like behavior, Sabra mice were subcutaneously injected on postnatal day 1-3 with a single dose of 5 mg/kg SR141716A or equivalent vehicle. At age 13 days, mice The effect of MH on vocal tic-like behavior is shown in FIG. 5. These results show that MH significantly reduces vocal tic-like behavior.

Example 6

Prophetical

With a view to study the effect of the raloxifene compositions on vocal tics-like behavior, inject subcutaneously Sabra mice on postnatal day 1-3 with a single dose of 5 mg/kg SR141716A or equivalent vehicle. At age 5-7 days, subcutaneously inject a single dose of 0.2-50 raloxifene one hour before mice are recorded with an ultrasonic voice recorder (AviSoft) from 20 to 100 kHz. A single mouse is recorded in a cage for 10 min. The number of events is analyzed.

Group 1: treat once control mice with vehicle on postnatal day 1-3 and again with vehicle on day 5-7.

Group 2: treat model mice once with SR141716A on postnatal day 1-3 and once with vehicle on day 5-7.

Group 3: treat model mice once with SR141716A on postnatal day 1-3 and once with 15 5, 10, 20 or 50 mg/kg raloxifene on day 5-7.

Example 7

Oral formulations of 4-O-methylhonokiol (MH) were prepared by dissolving MH in one of the self-emulsifying carriers detailed in Table 1 below (0.005-100 mg/kg) according to the teachings of the co-pending PCT application WO2017149392.

TABLE 1

Self-emulsifying carriers for the oral compositions of this invention

| Component | Supplier | Cat. No. | VMHK-01 mg | VMHK-01 % | VMHK-02 mg | VMHK-02 % | VMHK-03 mg | VMHK-03 % |
|---|---|---|---|---|---|---|---|---|
| Medium chain triglycerides (MCT oil) | Lipoid | 940028/909 | 45,000 | 40.90% | 45,000 | 39.81% | 40,000 | 34.12% |
| DL-alpha-Tocopherol acetate USP | Sigma | T3376 | 10,000 | 9.09% | 10,000 | 5.85% | 9,000 | 7.68% |
| DL-alpha tocopherol USP | Sigma | T3251 | 5,000 | 4.54% | 5,000 | 4.42% | 4,500 | 3.84% |
| Butylated hydroxytoluene | Sigma | 37450 | 25 | 0.023% | 25 | 0.022% | 25 | 0.021% |
| Polyoxyl 35 castor oil NF (Kolliphor ELP) | Sigma | 30906 | 35,000 | 31.81% | | | | |
| Tween-60 (Polysorbate 60 NF) | Sigma | 95754 | | | 36,000 | 31.85% | | |
| Tween-80 (Polysorbate 80 NF) | Sigma | 59924 | | | | | 35,000 | 29.86% |
| Span 80 (Sorbitan monooleate) NF | Sigma | 85548 | 10,000 | 9.09% | 12,000 | 10.62% | 6,200 | 5.29% |
| Tocophersolan (TPGS, Tocopherol PEG ester succinate) | Sigma | 57668 | | | | | 8,500 | 7.25% |
| Labrafil M1944 CS | Gattefosse | 3063 | | | | | 14,000 | 11.94% |
| Lecithin (Phospholipon 80) | ALC | 228197 | 5,000 | 4.54% | 5,000 | 4.42% | | |
| Ethyl alcohol anhydrous | Commercial alcohols | N/A | 5,000 | 4.54% | 5,000 | 4.42% | | |
| Total, mg | | | 110,025 | 100.00% | 118,025 | 100.00% | 117,225 | 100.00% | were injected subcutaneously a single dose of 0.2-50 MH one hour before mice were recorded with an ultrasonic voice recorder (AviSoft) from 20 to 100 kHz. A single mouse is recorded in a cage for 5 to 10 min. The number of events was analyzed.

Group 1: control mice were treated once with vehicle on postnatal day 1-3 and again treated once with vehicle on day 13 (n=5);

Group 2: model mice were treated once with SR141716A on postnatal day 1-3 and treated once with vehicle on day 13 (n=5);

Group 3: model mice were treated once with SR141716A on postnatal day 1-3 and treated once with MH on day 13 (n=6);

4-O-methylhonokiol (MH) dissolved in any of the self-emulsifying carriers of Table 1.

Example 8

With a view to study the effect of the Clomiphene citrate compositions on repetitive behavior, C57BL/6JOlaHsd mice were intraperitoneally injected at age 3 weeks with a single dose of Clomiphene citrate at 0.2-50 mg/kg or equivalent vehicle. HTR responses and ESR responses in mice were recorded.

Figure 7:
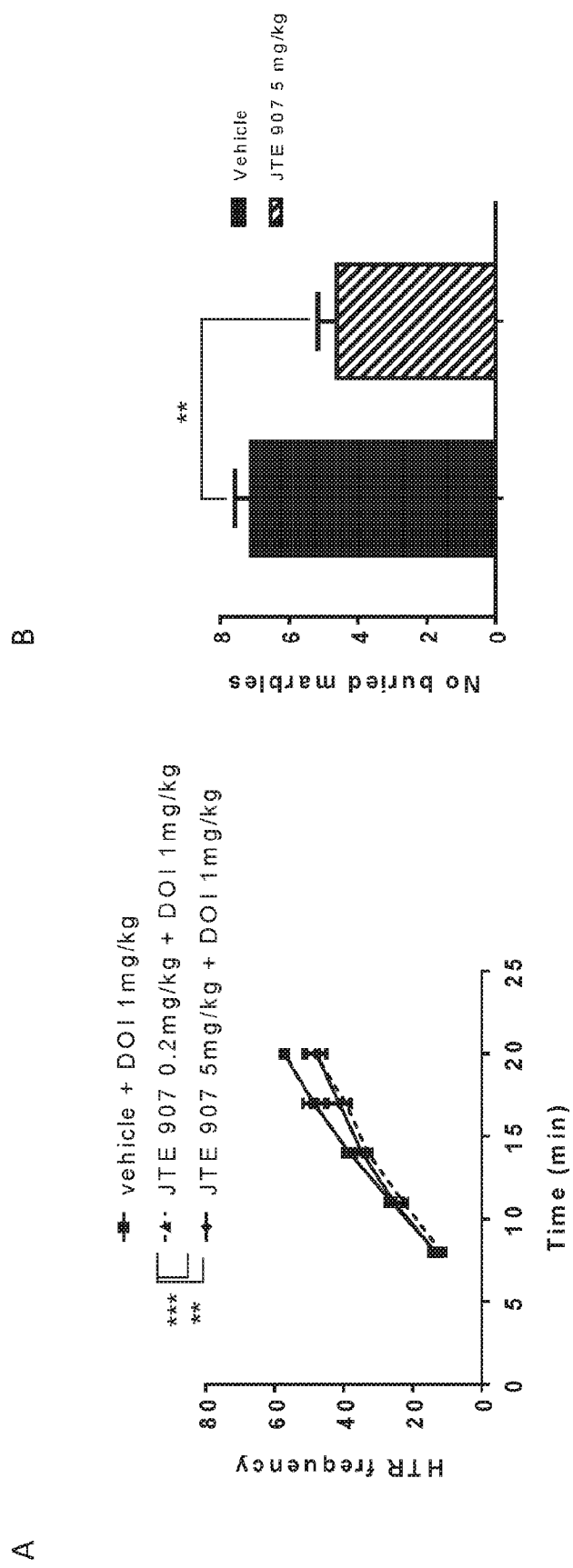
FIG. 7A-B are charts showing that JTE 907 reversed the effect of DOI on head twitch frequency (n=3 in each group.

Group 1: model mice were treated once with vehicle and once with saline (n=5);

Group 2: model mice were treated once with vehicle and once with DOI (n=5);

Group 3-4: drug tested mice were treated once with clomiphene citrate at 10 mg/kg and once with DOI (n=5);

The results for clomiphene citrate on repetitive behavior are shown in FIG. 7. At age 3 weeks, the model mice showed increased HTR frequency in the presence of DOI. One hour after a single injection, clomiphene citrate at 10 mg/kg did not significantly reverse the effect of DOI-induced HTR frequency. These results show that clomiphene citrate, a SERM ligand does not efficiently prevent repetitive behavior.

Example 9

With a view to study the effect of the JTE-907 compositions on repetitive behavior, C57BL/6J01aHsd mice were intraperitoneally injected at age 3 weeks with a single dose of JTE-907 at 0.2-50 mg/kg or equivalent vehicle. HTR responses and ESR responses in mice were recorded.

Group 1: model mice were treated once with vehicle and once with DOI (n=3);

Group 2-3: drug tested mice were treated once with JTE-907 at 0.2 mg/kg or 5 mg/kg (in each group n=3) and once with DOI;

The effects of JTE-907 on repetitive behavior are shown in FIG. 8A. At age 3 weeks, the model mice showed increased HTR frequency in the presence of DOI. One hour after a single injection, JTE-907 at 0.2 and 5 mg/kg reduced DOI-induced HTR frequency. These results show that JTE-907, a CB2 receptor selective inverse-agonist, reduces repetitive behavior in the presence of DOI.

Example 10

With a view to study the effect of the JTE-907 and M1 compositions on repetitive behavior, C57BL/6JOlaHsd mice were intraperitoneally injected at age 6 weeks with a single dose of JTE-907 at 0.2-50 mg/kg, M1 at 0.2-50 mg/kg or equivalent vehicle. The number of buried marbles in the burying marble test by each mouse was recorded.

Group 1: model mice were treated once with vehicle (n=6);

Group 2: drug tested mice were treated once with JTE-907 at 5 mg/kg or M1 10 mg/kg (in each group n=6);

The effects of JTE-907 on compulsive behavior is shown in FIG. 8B. The effects of M1 on compulsive behavior is shown in FIG. 9B. At age 6 weeks, the vehicle-treated mice showed increased compulsive behavior in the marble burying test. One hour after a single injection, JTE-907 at 5 mg/kg or MH at 10 mg/kg reduced the number of buried marbles. These results show that JTE-907 and MH, CB2 receptor selective inverse-agonists, reduce compulsive behavior.

Example 11

C57BL/6JOlaHsd mice at age 3 weeks were injected with a single dose of MH at 0.2-50 mg/kg or an equivalent oral formulation, with a view to study the effect of the MH compositions in oral formulations on repetitive behavior. Two hours later mice were intraperitoneally injected a single dose of 1 mg/kg DOI or saline. HTR responses and ESR responses in mice are recorded.

Group 1: model mice were orally (gavage) treated once with oral formulation and once intraperitoneally with DOI (n=8);

Groups 2-3: drug tested mice were orally (gavage) treated once with 1 mg/kg or 5 mg/kg M1 in an oral formulation and once intraperitoneally with DOI (n=8 in each group).

The effects of oral treatment of MH in oral formulation on repetitive behavior are shown in FIG. 9A. At age 3 weeks, the model mice showed increased HTR frequency in the presence of DOI vs. the control mice. Two hours after a single oral treatment, MH at 1 mg/kg and 5 mg/kg significantly reduced DOI-induced HTR frequency. The effect of MH at 1 mg/kg was greater than this of 5 mg/kg.

These results show that:
1. MH in oral formulation significantly reduces repetitive behavior.
2. A lower dose is required for effective treatment when using a formulation based on a stable self-microemulsifying vehicle.

Example 12

With a view to study the effect of the HU-308 compositions on repetitive behavior, C57BL/6JOlaHsd male mice were intraperitoneally injected at age 3 weeks with a single dose of HU-308 at 0.2-50 mg/kg or vehicle. HTR responses and ESR responses in mice were recorded.

Group 1: model mice were treated once with vehicle and once with DOI (n=8);

Group 2-3: drug tested mice were treated once with HU-308 at a dose of 0.2 mg/kg or 5 mg/kg and once with DOI (in each group n=8);

The effects of HU-308 on repetitive behavior are shown in FIG. 9A. At age 3 weeks, the model mice showed increased HTR frequency in the presence of DOI. One hour after a single injection, HU-308 at 0.2 and 5 mg/kg reduced DOI-induced HTR frequency. These results show that HU-308, a CB2 receptor selective agonist, reduces repetitive behavior in the presence of DOI.

Example 13

With a view to further study the effect of the HU-308 compositions on repetitive behavior, C57BL/6JOlaHsd mice were intraperitoneally injected at age 3 weeks with a single dose of HU-308 at 0.2-50 mg/kg or equivalent vehicle one hour later mice received a single injection of saline (i.e. in the absence of DOI to test the effect of HU-308 alone). HTR responses and ESR responses in mice were recorded.

Group 1: control mice were treated once with vehicle and once with saline (n=7);

Group 2: mice were treated once with HU-308 at a dose 0.2 mg/kg and once with saline (n=6);

The effects of HU-308 on repetitive behavior are shown in FIG. 9B. These results show that HU-308, a CB2 receptor selective agonist, significantly increased repetitive behavior.

Example 14

With a view to further study the effect of the HU-308 compositions on repetitive behavior, CB2 receptor knockout mice (The Jackson Laboratory) were intraperitoneally injected at age 3 weeks or 6-21 weeks with a single dose of HU-308 at 0.2-50 mg/kg or equivalent vehicle. One hour later mice were intraperitoneally injected a single dose of 1 mg/kg DOI or saline. HTR responses and ESR responses in mice were recorded.

Group 1: model mice were treated once with vehicle and once with DOI (n=3);

Group 2: drug tested mice were treated once with 5 mg/kg HU-308 and once with DOI (n=4);

The effects of HU-308 on repetitive behavior in CB2 receptor knockout mice are shown in FIG. 9C. At age 6-21 weeks, DOI-increased HTR frequency in male CB2 receptor knockout mice. HU-308 at 5 mg/kg significantly reduces the DOI-induced HTR frequency. Collectively with the results shown in FIGS. 9A-B, these results show that HU-308, a CB2 receptor selective agonist, is a candidate for the treatment of tic disorders and other repetitive 5 behavior disorders in a selected population with dysfunctional CB2 receptor.

The invention claimed is:

1. A method for programmable logic controller (PLC) program randomization, the method comprising:
   receiving, by an engineering system computer, source code corresponding to a PLC program;
   compiling, by the engineering system computer, the source code into a plurality of functionally equivalent intermediate representations of the PLC program, wherein program structure of the PLC program is randomized during compilation such that each intermediate representation is unique among the plurality of intermediate representations; and
   transmitting, by the engineering system computer, the plurality of intermediate representations to one or more PLCs;
wherein the PLC program comprises a plurality of function blocks, each identified by a triple comprising a numerical identifier and the program structure of the PLC program is randomized by:
   assigning a random value to each numerical identifier, and
   sorting the plurality of function blocks by numerical identifier.

2. The method of claim 1, further comprising:
   receiving, by the PLC, a first intermediate representation of the PLC program;
   compiling, by the PLC, the first intermediate representation into a PLC assembly code, wherein program structure of the first intermediate representation is randomized during compilation; and
   executing, by the PLC, the PLC assembly code.

3. The method of claim 2, further comprising:
   following failover of the PLC, re-compiling the first intermediate representation into a new PLC assembly code, wherein program structure of the first intermediate representation is randomized during re-compilation; and
   executing, by the PLC, the new PLC assembly code.

4. The method of claim 1, wherein the program structure of the PLC program is randomized during compilation by randomizing a memory layout of a plurality of data blocks used by the PLC program.

5. The method of claim 4, wherein the memory layout of plurality of data blocks is randomized by assigning a unique memory address to each data block.

6. The method claim 5, further comprising:
   sorting the plurality of data blocks by type during compilation to optimize memory access in the memory layout.

7. The method of claim 1, wherein the program structure of the PLC program is randomized during compilation by randomizing usage of a plurality of function blocks used by the PLC program.

8. The method of claim 7, wherein randomization of usage of the plurality of function blocks used by the PLC program comprises:
   randomizing ordering of parameters used in calling each function block.

9. The method of claim 7, wherein randomization of usage of the plurality of function blocks used by the PLC program comprises:
   randomizing ordering of cyclic variables used by each function block.

10. The method of claim 7, wherein randomization of usage of the plurality of function blocks used by the PLC program comprises randomizing control flow of each function block by:
    constructing a control flow graph where conditional statements are transformed into equivalent control flow constructs; and
    randomizing ordering of the control flow constructs.

11. The method of claim 7, wherein randomization of usage of the plurality of function blocks used by the PLC program comprises randomizing data flow of each function block by:
    constructing a data flow graph where conditional statements are transformed into equivalent data flow expressions; and
    randomizing ordering of the data flow expressions.

12. The method of claim 7, wherein randomization of usage of the plurality of function blocks used by the PLC program comprises inserting one or more non-functional function blocks into the plurality of function blocks.

13. The method of claim 1, wherein program structure of the PLC program is randomized during compilation by reordering one or more organization blocks in the PLC program.

14. A method for programmable logic controller (PLC) program randomization, the method comprising:
    receiving, by a PLC, an intermediate representation of a PLC program;
    compiling, by the PLC, the intermediate representation into PLC assembly code, wherein program structure of the intermediate representation is randomized during compilation with respect to usage of one or more program blocks; and
    executing, by the PLC, the PLC assembly code;
wherein the PLC program comprises a plurality of function blocks, each identified by a triple comprising a numerical identifier and the program structure of the PLC program is randomized by:
    assigning a random value to each numerical identifier, and
    sorting the plurality of function blocks by numerical identifier.

15. The method of claim 14, further comprising:
    following failover of the PLC, re-compiling the intermediate representation into a new PLC assembly code, wherein program structure of the intermediate representation is randomized during re-compilation; and
    executing, by the PLC, the new PLC assembly code.

16. The method of claim 14, wherein program structure of the intermediate representation is randomized during compilation by randomizing address values for one or more data blocks used by the PLC program.

17. The method of claim 14, wherein program structure of the intermediate representation is randomized during compilation by randomizing control flow of function blocks and functions used by the PLC program.

18. The method of claim 14, wherein program structure of the intermediate representation is randomized during compilation by randomizing data flow of function blocks and functions used by the PLC program.

19. The method of claim 14, wherein program structure of the intermediate representation is randomized during compilation by reordering one or more organization blocks used by the PLC program in the intermediate representation.

20. A system for programmable logic controller (PLC) program randomization, the system comprising:
- a computer readable storage medium storing source code corresponding to a PLC program;
- an engineering system configured to compile the source code into a plurality of functionally equivalent intermediate representations of the PLC program, wherein program structure of the PLC program is randomized during compilation such that each intermediate representation is unique among the plurality of intermediate representations; and
- a plurality of programmable logic controllers, each programmable logic controller configured to:
  - receive an intermediate representation of the PLC program from the engineering system;
  - compile the intermediate representation into PLC assembly code, wherein program structure of the intermediate representation is randomized during compilation with respect to usage of one or more program blocks, wherein the PLC program comprises a plurality of function blocks, each identified by a triple comprising a numerical identifier and the program structure of the PLC program is randomized by:
- assigning a random value to each numerical identifier, and
- sorting the plurality of function blocks by numerical identifier.

* * * * *